(12) United States Patent
Peer et al.

(10) Patent No.: US 11,851,389 B2
(45) Date of Patent: Dec. 26, 2023

(54) CATIONIC LIPIDS FOR NUCLEIC ACID DELIVERY AND PREPARATION THEREOF

(71) Applicant: RAMOT AT TEL-AVIV UNIVERSITY LTD., Tel Aviv (IL)

(72) Inventors: Dan Peer, Kiryat Ono (IL); Srinivas Ramishetti, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 741 days.

(21) Appl. No.: 16/347,995

(22) PCT Filed: Nov. 7, 2017

(86) PCT No.: PCT/IL2017/051212
§ 371 (c)(1),
(2) Date: May 7, 2019

(87) PCT Pub. No.: WO2018/087753
PCT Pub. Date: May 17, 2018

(65) Prior Publication Data
US 2019/0292130 A1  Sep. 26, 2019

Related U.S. Application Data

(60) Provisional application No. 62/507,829, filed on May 18, 2017, provisional application No. 62/418,844, filed on Nov. 8, 2016.

(51) Int. Cl.
| | | |
|---|---|---|
| C07C 211/22 | (2006.01) | |
| A61K 47/18 | (2017.01) | |
| C07C 215/08 | (2006.01) | |
| C07C 229/12 | (2006.01) | |
| C07C 243/00 | (2006.01) | |
| C07C 243/16 | (2006.01) | |
| C07C 243/28 | (2006.01) | |
| C07D 295/15 | (2006.01) | |
| C12N 15/113 | (2010.01) | |
| A61K 48/00 | (2006.01) | |
| C07C 243/04 | (2006.01) | |
| C07C 59/01 | (2006.01) | |
| C07C 333/10 | (2006.01) | |
| C07C 219/04 | (2006.01) | |
| C07D 233/64 | (2006.01) | |
| C07C 229/02 | (2006.01) | |
| A61P 29/00 | (2006.01) | |
| C07D 295/13 | (2006.01) | |
| C07C 243/26 | (2006.01) | |
| C07C 233/00 | (2006.01) | |
| C07C 243/14 | (2006.01) | |
| C07C 279/04 | (2006.01) | |
| A61P 35/00 | (2006.01) | |
| C07C 229/10 | (2006.01) | |
| C07C 243/10 | (2006.01) | |

(52) U.S. Cl.
CPC .......... *C07C 211/22* (2013.01); *A61K 47/18* (2013.01); *A61K 48/00* (2013.01); *A61P 29/00* (2018.01); *A61P 35/00* (2018.01); *C07C 59/01* (2013.01); *C07C 215/08* (2013.01); *C07C 219/04* (2013.01); *C07C 229/02* (2013.01); *C07C 229/10* (2013.01); *C07C 229/12* (2013.01); *C07C 233/00* (2013.01); *C07C 243/00* (2013.01); *C07C 243/10* (2013.01); *C07C 243/14* (2013.01); *C07C 243/16* (2013.01); *C07C 243/26* (2013.01); *C07C 243/28* (2013.01); *C07C 279/04* (2013.01); *C07C 333/10* (2013.01); *C07D 233/64* (2013.01); *C07D 295/13* (2013.01); *C07D 295/15* (2013.01); *C12N 15/113* (2013.01); *C12N 2310/14* (2013.01)

(58) Field of Classification Search
None
See application file for complete search history.

(56) References Cited

U.S. PATENT DOCUMENTS 3,703,554 A * 11/1972 Bordenca .............. C07C 323/25
564/457
2012/0095075 A1  4/2012 Manoharan

FOREIGN PATENT DOCUMENTS

| CH | 238948 | * 12/1945 | |
|---|---|---|---|
| EP | 2871178 A1 | 5/2015 | |
| JP | 09290563 A | * 11/1997 | ............. B41M 5/26 |
| JP | 2012508264 A | 4/2012 | |
| WO | 2006111982 A1 | 10/2006 | |
| WO | 2010054401 A1 | 5/2010 | |
| WO | 2011057020 A1 | 5/2011 | |
| WO | 2013016058 A1 | 1/2013 | |

(Continued)

OTHER PUBLICATIONS

CAS SciFinder abstract (database CAPLUS Acc. No. 1949:26417) of CH 238948 (Dec. 3, 1945).*

(Continued)

*Primary Examiner* — Brian J Davis
(74) *Attorney, Agent, or Firm* — BROWDY AND NEIMARK, PLLC

(57) ABSTRACT

The present invention provides cationic lipids and lipid nanoparticle formulations comprising these lipids, alone or in combination with other lipids. These lipid nanoparticles may be formulated with nucleic acids to facilitate their intracellular delivery both in vitro and for therapeutic applications. The present invention also provides methods of chemical synthesis of these lipids, lipid nanoparticle preparation and formulation with nucleic acids.

24 Claims, 22 Drawing Sheets
Specification includes a Sequence Listing.

(56) References Cited

FOREIGN PATENT DOCUMENTS

| WO | 2014007398 A1 | 1/2014 |
| WO | 2015199952 A1 | 12/2015 |
| WO | 2016021673 A1 | 2/2016 |
| WO | 2016176330 A1 | 11/2016 |
| WO | 2017075531 A1 | 5/2017 |

OTHER PUBLICATIONS

Lida et al., SciFinder English language abstract (database CAPLUS AN: 1997:732298) of JP09290563 A (1997).*
Rice et al., Journal of the American Chemical Society (1953), 75, p. 1750.*
Bordenca, CAS SciFinder n abstract of U.S. Pat. No. 3,703,554 (database CAPLUS AN: 1973:93638), 1973, 2 pages.*
Anonymous, database CAS Registry, compound 38456-03-0, retrieved from CAS using CAS SciFiner on Feb. 13, 2023.*
Berge et al., (1977) Pharmaceutical salts. J Pharm Sci 66(1): 1-19.
Cohen et al., (2015) Localized RNAi Therapeutics of Chemoresistant Grade IV Glioma Using Hyaluronan-Grafted Lipid-Based Nanoparticles. ACS Nano 9(2): 1581-1591.
Jayaraman et al., (2012) Maximizing the potency of simna lipid nanoparticles for hepatic gene silencing in vivo. Angew Chem Int Ed 51: 8529-8533.
Sabnis et al., (2018) A Novel Amino Lipid Series for mRNA Delivery: Improved Endosomal Escape and Sustained Pharmacology and Safety in Non-human Primates. Mol Ther 26(6): 1509-1519.
Database Registry on STN. Entered Jun. 12, 2008, RN 1027464-32-9. 1 page.

\* cited by examiner

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: modified with 2'-OMe
<220> FEATURE:
```

```
<221> NAME/KEY: misc_feature
<222> LOCATION: (5)..(6)
<223> OTHER INFORMATION: modified with 2'-OMe
<220> FEATURE:
<221> NAME/KEY: misc_feature
<222> LOCATION: (10)..(13)
<223> OTHER INFORMATION: modified with 2'-OMe
<220> FEATURE:
<221> NAME/KEY: misc_feature
<222> LOCATION: (18)..(18)
<223> OTHER INFORMATION: modified with 2'-OMe
<220> FEATURE:
<221> NAME/KEY: misc_feature
<222> LOCATION: (20)..(21)
<223> OTHER INFORMATION: phosphorothioate linkage

<400> SEQUENCE: 1
cuggcugaau uucagagcat t                                     21

<210> SEQ ID NO 2
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (13)..(13)
<223> OTHER INFORMATION: modified with 2'-OMe
<220> FEATURE:
<221> NAME/KEY: misc_feature
<222> LOCATION: (17)..(17)
<223> OTHER INFORMATION: modified with 2'-OMe
<220> FEATURE:
<221> NAME/KEY: misc_feature
<222> LOCATION: (20)..(21)
<223> OTHER INFORMATION: phosphorothioate linkage

<400> SEQUENCE: 2
ugcucugaaa uucagccagt t                                     21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: modified with 2'-OMe
<220> FEATURE:
<221> NAME/KEY: misc_feature
<222> LOCATION: (5)..(5)
<223> OTHER INFORMATION: modified with 2'-OMe
<220> FEATURE:
<221> NAME/KEY: misc_feature
<222> LOCATION: (7)..(8)
<223> OTHER INFORMATION: modified with 2'-OMe
<220> FEATURE:
<221> NAME/KEY: misc_feature
<222> LOCATION: (12)..(12)
<223> OTHER INFORMATION: modified with 2'-OMe
<220> FEATURE:
<221> NAME/KEY: misc_feature
<222> LOCATION: (14)..(17)
<223> OTHER INFORMATION: modified with 2'-OMe
<220> FEATURE:
<221> NAME/KEY: misc_feature
<222> LOCATION: (20)..(21)
<223> OTHER INFORMATION: phosphorothioate linkage

<400> SEQUENCE: 3
cuuacgcuga guacuucgat t                                     21
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: modified with 2'-OMe
<220> FEATURE:
<221> NAME/KEY: misc_feature
<222> LOCATION: (11)..(11)
<223> OTHER INFORMATION: modified with 2'-OMe
<220> FEATURE:
<221> NAME/KEY: misc_feature
<222> LOCATION: (16)..(16)
<223> OTHER INFORMATION: modified with 2'-OMe
<220> FEATURE:
<221> NAME/KEY: misc_feature
<222> LOCATION: (20)..(21)
<223> OTHER INFORMATION: phosphorothioate linkage

<400> SEQUENCE: 4
ucgaaguacu cagcguaagt t                                             21

<210> SEQ ID NO 5
<211> LENGTH: 25
<212> TYPE: RNA
<213> ORGANISM: Artificial Sequence
<220> FEATURE:
<223> OTHER INFORMATION: Synthetic

<400> SEQUENCE: 5
cauauugcgc guauagucgc guuag                                         25

<210> SEQ ID NO 6
<211> LENGTH: 27
<212> TYPE: RNA
<213> ORGANISM: Artificial Sequence
<220> FEATURE:
<223> OTHER INFORMATION: Synthetic

<400> SEQUENCE: 6
ugguauaacg cgcauaucag cgcaauc                                       27

<210> SEQ ID NO 7
<211> LENGTH: 25
<212> TYPE: DNA
<213> ORGANISM: Artificial Sequence
<220> FEATURE:
<223> OTHER INFORMATION: Synthetic

<400> SEQUENCE: 7
gcuuaaugac gaguucuuua cuuct                                         25

<210> SEQ ID NO 8
<211> LENGTH: 27
<212> TYPE: RNA
<213> ORGANISM: Artificial Sequence
<220> FEATURE:
<223> OTHER INFORMATION: Synthetic

<400> SEQUENCE: 8
gacgaauuac ugcucaagaa augaaga                                       27

<210> SEQ ID NO 9
```

```
<211> LENGTH: 20
<212> TYPE: DNA
<213> ORGANISM: Artificial Sequence
<220> FEATURE:
<223> OTHER INFORMATION: Synthetic

<400> SEQUENCE: 9
accagcacgt cgtaggattc                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
caagcacaat ttgccgtagg                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
tcagggtttc acatttggca                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
gagcatggat cggaaaacca                                            20
```

CATIONIC LIPIDS FOR NUCLEIC ACID DELIVERY AND PREPARATION THEREOF

FIELD OF THE INVENTION

The present invention provides cationic lipids and lipid nanoparticle formulations comprising these lipids, alone or in combination with other lipids. These lipid nanoparticles may be formulated with nucleic acids to facilitate their intracellular delivery both in vitro and for in vivo therapeutic applications. The present invention also provides methods of chemical synthesis of these lipids, lipid nanoparticle preparation and formulation with nucleic acids.

BACKGROUND OF THE INVENTION

Therapeutic nucleic acids including small interfering RNA (siRNA), micro RNA (miRNA), antisense oligo nucleotides, messenger RNA (mRNA), ribozymes, pDNA and immune stimulating nucleic acids are act via a variety of mechanisms. Specific proteins can be downregulated by siRNA or miRNA through RNA interference (RNAi). Hematopoietic cells, such as leukocytes in general, and primary T lymphocytes and B-cells in particular, are notoriously hard to transfect with small interfering RNAs (siRNAs). Modulating immune cells function, such as T cells and B-cells, by downregulating specific genes using RNA interference (RNAi) holds tremendous potential in advancing targeted therapies in many immune related disorders including cancer, inflammation, autoimmunity and viral infections. The therapeutic applications of RNAi are extremely broad, since siRNA and miRNA constructs can be synthesized with any nucleotide sequence directed against a target protein. To date, siRNA constructs have shown the ability to specially silence target proteins in both in vitro and in vivo models. These are currently being evaluated in clinical studies.

Messenger RNA (mRNA) is the family of large RNA molecules which transport the genetic information from DNA to ribosome. Some nucleic acids, such as mRNA or plasmids, can be used to effect expression of specific cellular products. Such nucleic acids would be useful in the treatment of diseases related deficiency of a protein or enzyme. However many problems associated with nucleic acids in therapeutic contexts. One of the major problems with therapeutic nucleic acids is the stability of the phosphodiester inter nucleotide link and its susceptibility to nucleases. Apart from that these nucleic acids have limited ability to cross the cell membrane.

Cationic lipids have proved to be excellent carriers of nucleic acids to treat varies diseases in gene therapy applications. Lipid nanoparticles formed from cationic lipids and other co-lipids such as cholesterol, DSPC and PEGylated lipids encapsulated oligonucleotides which protect them from degradation and facilitate the cellular uptake. Nevertheless, there remains a need in the art for suitable and efficient delivery platforms for delivery of oligonucleotides.

SUMMARY OF THE INVENTION

The present invention relates to novel cationic lipids which can be used in lipid nanoparticle preparation. These lipid nanoparticles protect nucleic acids from degradation, clearance from circulation and intracellular release. In addition, the nucleic acid encapsulated lipid nanoparticles advantageously are well-tolerated and provide an adequate therapeutic index, such that patient treatment at an effective dose of the nucleic acid is not associated with unacceptable toxicity and/or risk to the patient. The present invention also provides the methods of chemical synthesis of these lipids, lipid nanoparticle preparation and formulations with nucleic acids.

In some embodiments, the present invention relates to novel cationic lipids, and formulations of such lipids with siRNA and pDNA. These lipid nanoparticles (LNPs) were further characterized by DLS and assessed for their in vitro activity in various cancer cell lines.

According to the principles of the present invention, the lipids structures are based on functional groups such as hydrazine, hydrazide or hydroxylamine linked, directly or through a linker to a fatty acid residue R—C(=O)—, R—C(=O)—O— or R— wherein RCOOH is the corresponding fatty acid which may be saturated or unsaturated. The lipids also contain a functional head group, for example an amine, an N-containing heterocycle or heteroaryl, or an amino acid side chain (e.g., histidine or arginine side chains), which is linked through a linker, e.g., an alkylene chain. In some embodiments, the lipids feature an asymmetrical structure and enhanced charge, hence it is hypothesized that such lipids will display improved binding and improve endosomal escape (i.e., enhanced stability) due to structural imbalance. Other lipids according to the invention have symmetrical structures as further described herein.

Thus, in one embodiment, the present invention relates to a cationic lipid comprising a functional group represented by the structure:

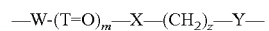

wherein
X and Y are each independently O, N or NH, wherein X and Y cannot both simultaneously be O;
W is a bond, O, NH or S;
T is C or S;
m is 0 or 1; and
z is 0 or 2;
wherein the functional group is linked to at least one saturated or unsaturated fatty acid residue.

In some embodiments, the cationic lipid comprises two fatty acid residues symmetrically or asymmetrically linked to the aforementioned functional group.

In one aspect of the present invention, the cationic lipid is represented by the structure of formula (I):

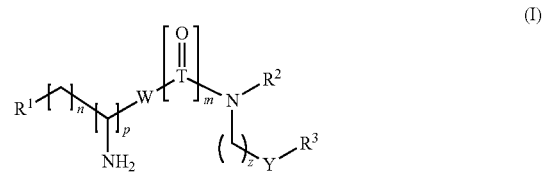

wherein
Y is O or NH;
T is C or S;
W is a bond, O, NH or S;
$R^1$ is selected from the group consisting of:
  (a) $NR^4R^5$ wherein $R^4$ and $R^5$ are each independently a $C_1$-$C_4$ alkyl; or $R^4$ and $R^5$ together with the nitrogen to which they are attached form a 5 or 6 membered heterocyclic or heteroaromatic ring, optionally containing one or more additional heteroatoms selected from the group consisting of O, N and S; or $NR^4R^5$ represent a guanidine group (—NHC(=NH)NH$_2$);

(b) the side chain of a natural or unnatural amino acid; and
(c) a 5 or 6 membered heterocyclic or heteroaromatic ring containing one or more heteroatoms selected from the group consisting of O, N and S;

$R^2$ and $R^3$ are selected from the group consisting of:
(a) $C_{10}$-$C_{22}$ alkyl;
(b) $C_{10}$-$C_{22}$ alkenyl;
(c) $C_{10}$-$C_{22}$ alkynyl;
(d) $C_4$-$C_{10}$ alkylene-Z—$C_4$-$C_{22}$ alkyl; and
(e) $C_4$-$C_{10}$ alkylene-Z—$C_4$-$C_{22}$ alkenyl;

Z is —O—C(=O)—, —C(=O)—O— or —O—;
n is 0, 1, 2, 3, 4, 5 or 6;
m is 0 or 1;
p is 0 or 1; and
z is 0 or 2;

including salts, hydrates, solvates, polymorphs, optical isomers, geometrical isomers, enantiomers, diastereomers, and mixtures thereof.

In some embodiments, the compound of formula (I) comprises a functional group selected from hydrazine, hydroxylamine, hydrazide, ethanolamine and ethylenediamine. Each possibility represents a separate embodiment of the present invention.

In some embodiments of formula (I), m is 0. In other embodiments of formula (I), m is 1. In other embodiments of formula (I), p is 0. In other embodiments of formula (I), p is 1. In other embodiments of formula (I), m is 0 and p is 0. In other embodiments of formula (I), m is 1 and p is 0. In other embodiments of formula (I), z is 0. In other embodiments of formula (I), z is 2. In other embodiments of formula (I), T C. In other embodiments of formula (I), W is a bond. In other embodiments of formula (I), $R^1$ is $NR^4R^5$.

In some representative embodiments of formula (I), p is 0, W is a bond and T is C, and the compound is represented by the structure of formula (Ia). In some representative embodiments of formula (Ia), $R^1$ is $NR^4R^5$, and the compound is represented by the structure of formula (Ia-1). The structures of formulae (Ia) and (Ia-1) are depicted in the detailed description hereinbelow.

In another aspect of the present invention, the cationic lipid is represented by the structure of formula (II):

(II)

wherein
A is

X' is O or NH;
Y' is O or NH;

provided that when A is

X' and Y' cannot both simultaneously be O;
T is C or S;
W is a bond, O, NH or S;
$R^1$ is selected from the group consisting of:
(a) $NR^4R^5$ wherein $R^4$ and $R^5$ are each independently a $C_1$-$C_4$ alkyl; or $R^4$ and $R^5$ together with the nitrogen to which they are attached form a 5 or 6 membered heterocyclic or heteroaromatic ring, optionally containing one or more additional heteroatoms selected from the group consisting of O, N and S; or $NR^4R^5$ represent a guanidine group (—NHC(=NH)NH$_2$);
(b) the side chain of a natural or unnatural amino acid; and
(c) a 5 or 6 membered heterocyclic or heteroaromatic ring containing one or more heteroatoms selected from the group consisting of O, N and S;

$R^2$ and $R^3$ are selected from the group consisting of:
(a) $C_{10}$-$C_{22}$ alkyl;
(b) $C_{10}$-$C_{22}$ alkenyl;
(c) $C_{10}$-$C_{22}$ alkynyl;
(d) $C_4$-$C_{10}$ alkylene-Z—$C_4$-$C_{22}$ alkyl; and
(e) $C_4$-$C_{10}$ alkylene-Z—$C_4$-$C_{22}$ alkenyl;

Z is —O—C(=O)—, —C(=O)—O— or —O—;
n is 0, 1, 2, 3, 4, 5 or 6;
m is 0 or 1;
p is 0 or 1; and
z is 0 or 2;

including salts, hydrates, solvates, polymorphs, optical isomers, geometrical isomers, enantiomers, diastereomers, and mixtures thereof.

In some embodiments, the compound of formula (II) comprises a functional group selected from hydrazine, hydroxylamine, hydrazide, ethanolamine and ethylenediamine. Each possibility represents a separate embodiment of the present invention.

In some embodiments of formula (II), m is 0. In other embodiments of formula (II), m is 1. In other embodiments of formula (II), m is 1. In other embodiments of formula (II), m is 1 and p is 0. In other embodiments of formula (II), z is 0. In other embodiments of formula (II), z is 2. In other embodiments of formula (II), T is C. In other embodiments of formula (II), W is a bond. In some embodiments of formula (II), m is 0 and W is O.

In some representative embodiments of formula (II), the cationic lipid is represented by the structure of formula (IIa). In some representative embodiments of formula (IIa), the cationic lipid is represented by the structure of formula (IIa-1). In other representative embodiments of formula (IIa), the cationic lipid is represented by the structure of formula (IIa-2). In other representative embodiments of formula (IIa), the cationic lipid is represented by the structure of formula (IIa-3). In other representative embodiments of formula (IIa), the cationic lipid is represented by the structure of formula (IIa-4). In other representative embodiments of formula (II), the cationic lipid is represented by the structure of formula (IIb). In some representative embodiments of formula (IIb), the cationic lipid is represented by the structure of formula (IIb-1).

The structures of formulae (IIa), (IIa-1), (IIa-2), (IIa-3), (IIa-4), (IIb) and (IIb-1) are depicted in the detailed description hereinbelow.

Specific examples of the compounds of formula (I), (Ia), (Ia-1), (II), (IIa), (IIa-1), (IIa-2), (IIa-3), (IIa-4), (IIb) and (IIb-1) are compounds 1-66, the structures of which are depicted in Table 1 in the Detailed Description. Each possibility represents a separate embodiment of the present invention.

An intermediate of formula (IIa-5), which can be used to prepare a compound of formula (IIa-4), represents a separate embodiment of the invention.

In another aspect, the cationic lipid of the present invention is represented by the structure of formula (III):

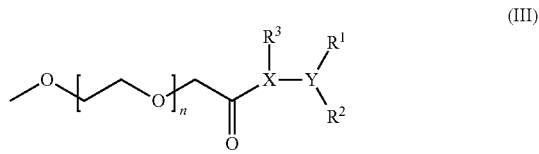

(III)

wherein
X and Y are each independently O, N or NH, wherein X and Y cannot both simultaneously be O;
each of $R^1$, $R^2$ and $R^3$ is independently absent or a $C_{10}$-$C_{22}$ alkyl, a $C_{10}$-$C_{22}$ alkenyl or a $C_{10}$-$C_{22}$ alkynyl; and
n is an integer between 1 and 30;
including salts, hydrates, solvates, polymorphs, optical isomers, geometrical isomers, enantiomers, diastereomers, and mixtures thereof.

In another aspect, the cationic lipid of the present invention is represented by the structure of formula (IIIA):

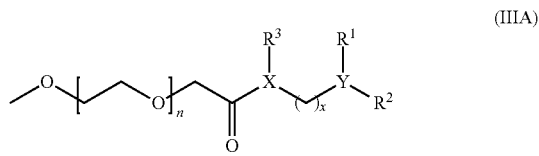

(IIIA)

wherein
X and Y are each independently O, N or NH, wherein X and Y cannot both simultaneously be O;
each of $R^1$, $R^2$ and $R^3$ is independently absent or a $C_{10}$-$C_{22}$ alkyl, a $C_{10}$-$C_{22}$ alkenyl or a $C_{10}$-$C_{22}$ alkynyl;
n is an integer between 1 and 30; and
x is 0 or 2;
including salts, hydrates, solvates, polymorphs, optical isomers, geometrical isomers, enantiomers, diastereomers, and mixtures thereof.

Specific examples of the compounds of formula (III) are compounds 67-70, the structures of which are depicted in Table 2 in the Detailed Description. Each possibility represents a separate embodiment of the present invention.

In another aspect, the present invention relates to a composition comprising the cationic lipid of any one of formulae (I), (Ia), (Ia-1), (II), (IIa), (IIa-1), (IIa-2), (IIa-3), (IIa-4), (IIb), (IIb-1) and (III), and further comprising at least one additional neutral or PEG-modified lipid. In some embodiments, the composition may further comprise a nucleic acid. Examples of nucleic acids include, but are not limited to, small interfering RNA (siRNA), micro RNA (miRNA), antisense oligo nucleotides, messenger RNA (mRNA), ribozymes, pDNA, CRISPR mRNA, gRNA and immune stimulating nucleic acids. Each possibility represents a separate embodiment of the present invention.

In another aspect, the present invention relates to a method of gene silencing, comprising the step of contacting a cell with a composition according to the present invention. In some embodiments, the cell is a cancer cell.

In other embodiments, the compositions of the present invention may be used as a delivery system to administer a therapeutic agent to its target location in the body. Thus, in some embodiments, the present invention relates to a method for administering a therapeutic agent, by preparing a composition comprising a cationic lipid as described herein and a therapeutic agent, and administering the combination to a subject in need thereof.

The cationic lipids of the present invention can be used alone or in combination with other lipid components such as neutral lipids, charged lipids, steroids (including, for example, sterols) and/or their analogs, and/or polymer conjugated lipids to form lipid nanoparticles for the delivery of therapeutic agents. In some instances the lipid nanoparticles are used to deliver nucleic acids for the treatment of various diseases or conditions, in particular leukocyte associated conditions such as inflammation and/or lack of sufficient protein.

Thus, in some embodiments, the present invention relates to a method of treating a leukocyte associated condition, the method comprising the step of administering to a subject in need thereof a composition according to the present invention. The leukocyte associated condition may be selected from the group consisting of cancer, infection, autoimmune diseases, neurodegenerative diseases and inflammation.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 10: Effect of PLK1 silencing on cell viability; Human B-cell lymphoma suspension cells (RPMI-8226) were incubated with LNPs comprising cationic lipids 38 or 55 and siPLK1 or ctl-siRNA at different concentrations for 48 hrs. Cell viability induced by PLK1 down regulation was measured by XTT assay.

FIG. 14A: Lipid 1. FIG. 14B: Lipid 10.

DETAILED DESCRIPTION OF THE PRESENT INVENTION

Figure 1A:
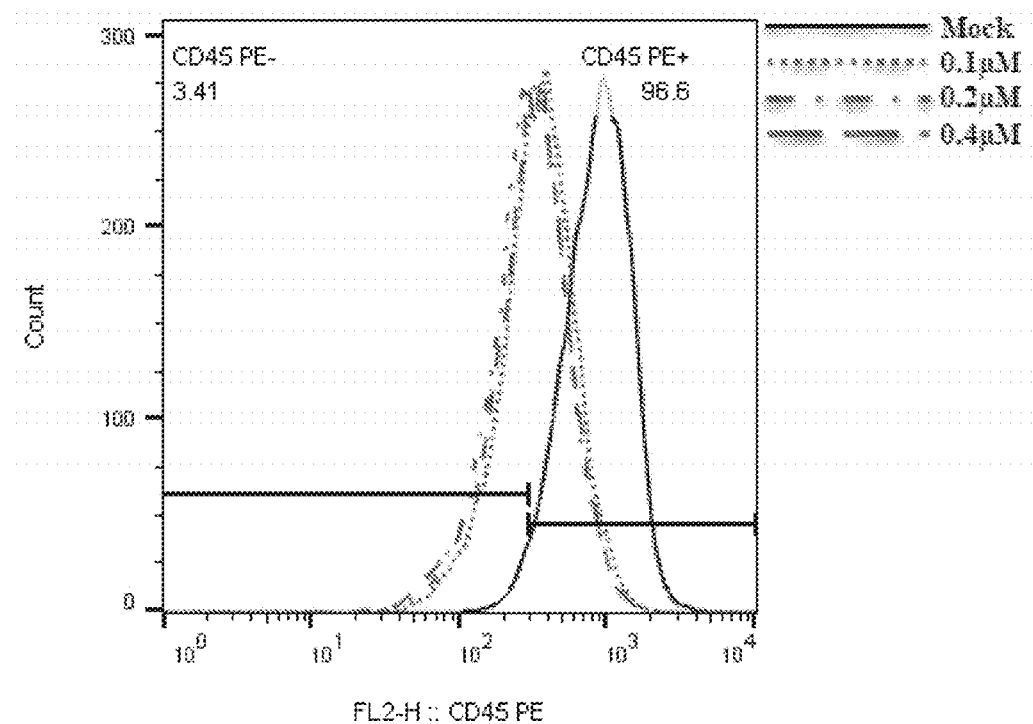
FIG. 1: In vitro gene silencing effect lipid 1: Human T cells SupT1 were treated with lipid nanoparticle (LNP) comprising of cationic lipid 1 encapsulated siCD45 for 48 hrs (A) or 72 hrs (B) at different siRNA doses (0.4 μM, 0.2 μM, 0.1 μM).

The present invention based on the discovery of cationic lipids useful in preparing lipid nanoparticles to deliver active agents in vitro and in vivo. The cationic lipids of the present invention are useful in delivery of nucleic acids such as siRNA, miRNA and mRNA etc.

Cationic Lipids

In some embodiment, the present invention relates to a cationic lipid comprising a hydrazine, hydrazine, hydroxylamine, ethanolamine or diethylene diamine moiety linked to at least one saturated or unsaturated fatty acid residue. In some embodiments, the cationic lipid comprises two fatty acid residues asymmetrically linked to the hydrazine, hydrazine, hydroxylamine, ethanolamine or diethylene diamine moiety.

As contemplated herein, the present invention relates to a cationic lipid comprising a functional group represented by the structure:

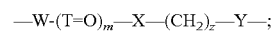

wherein
X and Y are each independently O, N or NH, wherein X and Y cannot both be O;
W is a bond, O, NH or S;
T is C or S;
m is 0 or 1; and
z is 0 or 2;
wherein the functional group is linked to at least one saturated or unsaturated fatty acid residue.

In some embodiments, X and Y are each independently O or N, wherein X and Y cannot both be O.

In some embodiments, the cationic lipid comprises two fatty acid residues symmetrically or asymmetrically linked to the aforementioned functional group.

In one aspect of the present invention, X is N, and the cationic lipid is represented by the structure of formula (I):

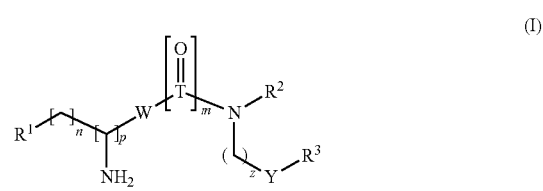

wherein
Y is O or NH;
T is C or S;
W is a bond, O, NH or S;

$R^1$ is selected from the group consisting of:
(a) $NR^4R^5$ wherein $R^4$ and $R^5$ are each independently a $C_1$-$C_4$ alkyl; or $R^4$ and $R^5$ together with the nitrogen to which they are attached form a 5 or 6 membered heterocyclic or heteroaromatic ring, optionally containing one or more additional heteroatoms selected from the group consisting of O, N and S; or $NR^4R^5$ represent a guanidine group (—NHC(=NH)NH$_2$);
(b) the side chain of a natural or unnatural amino acid; and
(c) a 5 or 6 membered heterocyclic or heteroaromatic ring containing one or more heteroatoms selected from the group consisting of O, N and S;

$R^2$ and $R^3$ are selected from the group consisting of:
(a) $C_{10}$-$C_{22}$ alkyl;
(b) $C_{10}$-$C_{22}$ alkenyl;
(c) $C_{10}$-$C_{22}$ alkynyl;
(d) $C_4$-$C_{10}$ alkylene-Z—$C_4$-$C_{22}$ alkyl; and
(e) $C_4$-$C_{10}$ alkylene-Z—$C_4$-$C_{22}$ alkenyl;

Z is —O—C(=O)—, —C(=O)—O— or —O—;
n is 0, 1, 2, 3, 4, 5 or 6;
m is 0 or 1;
p is 0 or 1; and
z is 0 or 2;
including salts, hydrates, solvates, polymorphs, optical isomers, geometrical isomers, enantiomers, diastereomers, and mixtures thereof.

In some embodiments of formula (I), $R^2$ and $R^3$ are selected from the group consisting of: (a) a $C_{10}$-$C_{22}$ alkyl, a $C_{10}$-$C_{22}$ alkenyl or a $C_{10}$-$C_{22}$ alkynyl; and (b) $C_4$-$C_{10}$ alkylene-Z—$C_4$-$C_{22}$ alkyl wherein Z is —O—C(=O)—, —C(=O)—O— or —O—. Each possibility represents a separate embodiment of the present invention.

In some embodiments of formula (I), $R^1$ is $NR^4R^5$. In some embodiments of formula (I), $R^1$ is the side chain of a natural or unnatural amino acid. In some embodiments of formula (I), $R^1$ is a 5 or 6 membered heterocyclic or heteroaromatic ring containing one or more heteroatoms selected from the group consisting of O, N and S.

In some embodiments, the compound of formula (I) comprises a functional group selected from the group consisting of hydrazine, hydroxylamine, hydrazide, ethanolamine and ethylenediamine. Each possibility represents a separate embodiment of the present invention.

In some embodiments of formula (I), m is 0. In other embodiments of formula (I), m is 1. In other embodiments of formula (I), p is 0. In other embodiments of formula (I), p is 1. In other embodiments of formula (I), m is 0 and p is 0. In other embodiments of formula (I), m is 1 and p is 0. In other embodiments of formula (I), z is 0. In other embodiments of formula (I), z is 2. In other embodiments of formula (I), T is C. In other embodiments of formula (I), W is a bond.

In some representative embodiments of formula (I), p is 0, W is a bond and T is C, and the compound is represented by the structure of formula (Ia):

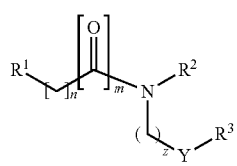

wherein $R^1$, $R^2$, $R^3$, Y, m, n and z are as defined in formula (I).

In some embodiments of formula (Ia), m is 0. In other embodiments of formula (Ia), m is 1. In other embodiments of formula (I), z is 0. In other embodiments of formula (Ia), $R^2$ and $R^3$ are each independently a $C_{14}$-$C_{20}$ alkyl or a $C_{14}$-$C_{20}$ alkenyl. In other embodiments of formula (Ia), $R^2$ and $R^3$ are each independently a $C_4$-$C_{10}$ alkylene-Z—$C_4$-$C_{22}$ alkyl wherein Z is —O—C(=O)—, —C(=O)—O— or —O—. In other embodiments, of formula (a), $R^2$ and $R^3$ are each independently a $C_4$-$C_{10}$ alkylene-Z—$C_4$-$C_{22}$ alkenyl wherein Z is —O—C(=O)—, —C(=O)—O— or —O—. In other embodiments of formula (Ia), Y is O. In other embodiments of formula (Ia), Y is NH.

In other representative embodiments of formula (I), $R^1$ is $NR^4R^5$, and the compound is represented by the structure of formula (Ia-1):

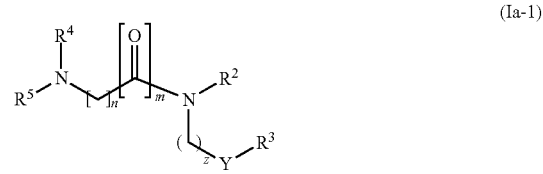

wherein $R^2$, $R^3$, $R^4$, $R^5$, Y, m, n and z are as defined in formula (I).

In some embodiments of formula (Ia-1), $R^4$ and $R^5$ are each $CH_3$. In other embodiments of formula (Ia-1), $R^4$ and $R^5$ together with the nitrogen to which they are attached form a heterocyclic ring selected from the group consisting of pyrrolidinyl piperidininyl and piperazinyl, each of which is optionally substituted with an alkyl. Each possibility represents a separate embodiment of the present invention.

In another aspect of the present invention, the cationic lipid is represented by the structure of formula (II):

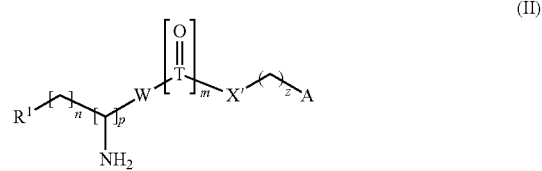

wherein
A is

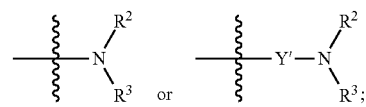

X' is O or NH;
Y' is O or NH;
provided that when A is

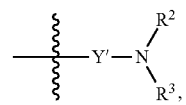

X' and Y' cannot both be O;

T is C or S;

W is a bond, O, NH or S;

$R^1$ is selected from the group consisting of:

(a) $NR^4R^5$ wherein $R^4$ and $R^5$ are each independently a $C_1$-$C_4$ alkyl; or $R^4$ and $R^5$ together with the nitrogen to which they are attached form a 5 or 6 membered heterocyclic or heteroaromatic ring, optionally containing one or more additional heteroatoms selected from the group consisting of O, N and S; or $NR^4R^5$ represent a guanidine group (—NHC(=NH)$NH_2$);

(b) the side chain of a natural or unnatural amino acid; and (c) a 5 or 6 membered heterocyclic or heteroaromatic ring containing one or more heteroatoms selected from the group consisting of O, N and S;

$R^2$ and $R^3$ are selected from the group consisting of:

(a) $C_{10}$-$C_{22}$ alkyl;

(b) $C_{10}$-$C_{22}$ alkenyl;

(c) $C_{10}$-$C_{22}$ alkynyl;

(d) $C_4$-$C_{10}$ alkylene-Z—$C_4$-$C_{22}$ alkyl; and (e) $C_4$-$C_{10}$ alkylene-Z—$C_4$-$C_{22}$ alkenyl;

Z is —O—C(=O)—, —C(=O)—O— or —O—;

n is 0, 1, 2, 3, 4, 5 or 6;

m is 0 or 1;

p is 0 or 1; and z is 0 or 2;

including salts, hydrates, solvates, polymorphs, optical isomers, geometrical isomers, enantiomers, diastereomers, and mixtures thereof.

In some embodiments of formula (II), $R^2$ and $R^3$ are selected from the group consisting of: (a) a $C_{10}$-$C_{22}$ alkyl, a $C_{10}$-$C_{22}$ alkenyl or a $C_{10}$-$C_{22}$ alkynyl; and (b) $C_4$-$C_{10}$ alkylene-Z—$C_4$-$C_{22}$ alkyl wherein Z is —O—C(=O)—, —C(=O)—O— or —O—. Each possibility represents a separate embodiment of the present invention.

In some embodiments of formula (II), m is 0. In other embodiments of formula (II), m is 1. In other embodiments of formula (II), m is 1. In other embodiments of formula (II), m is 1 and p is 0. In other embodiments of formula (II), z is 0. In other embodiments of formula (II), z is 2. In other embodiments of formula (II), T is C. In other embodiments of formula (II), W is a bond. In some embodiments of formula (II), m is 0 and W is O.

In some representative embodiments of formula (II), the cationic lipid is represented by the structure of formula (IIa):

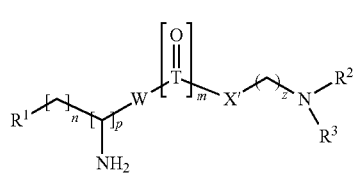

(IIa)

wherein $R^1$, $R^2$, $R^3$, X', T, W, n, m, p and z are as defined in formula (II).

In some embodiments of formula (IIa) p is 0, W is a bond and T is C, and the compound is represented by the structure of formula (IIa-1):

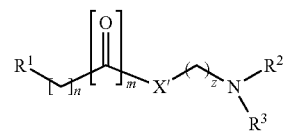

(IIa-1)

wherein $R^1$, $R^2$, $R^3$, X', n, m and z are as defined in formula (II).

In other embodiments of formula (IIa), $R^1$ is $NR^4R^5$, and the compound is represented by the structure of formula (IIa-2):

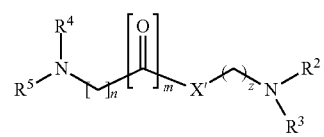

(IIa-2)

wherein $R^2$, $R^3$, $R^4$, $R^5$, X', n, m and z are as defined in formula (II).

In yet other embodiments of formula (IIa), p is 1, m is 1, W is a bond and T is C, and the compound is represented by the structure of formula (IIa-3):

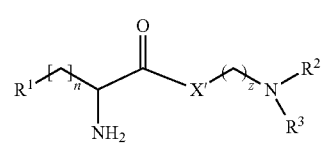

(IIa-3)

wherein $R^1$ is the side chain of a natural or unnatural amino acid; and $R^2$, $R^3$, X', n and z are as defined in formula (II).

In some embodiments of formula (IIa), p is 0, $R^1$ is $NR^4R^5$, W is a bond, m is 0, X' is O and the compound is represented by the structure of formula (IIa-4):

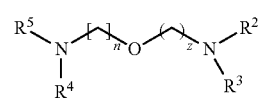

(IIa-4)

In some embodiments, compounds of formula (IIa-5) can be used as intermediates for preparing compounds of formula (IIa-4):

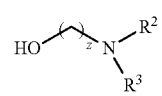

(IIa-5)

wherein $R^2$ and $R^3$ are as defined in formula (IIa-4).

In other representative embodiments of formula (II), the cationic lipid is represented by the structure of formula (IIb):

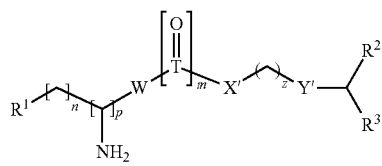
(IIb)

wherein R, $R^2$, $R^3$, T, W, X', Y' n, m, p and z are as defined in formula (II).

In some representative embodiments of formula (IIb), p is 0, W is a bond, T is C, and $R^1$ is $NR^4R^5$, and the compound is represented by the structure of formula (IIb-1):

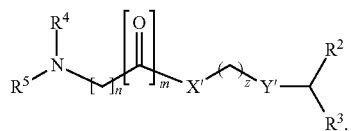
(IIb-1)

wherein $R^2$, $R^3$, $R^4$, $R^5$, X', Y', n, m and z are as defined in formula (II).

In some embodiments of the compounds of any of formulae (II), (IIa), (IIa-1), (IIa-2), (IIa-3), (IIa-4), (IIb) and (IIb-1), $R^2$ and $R^3$ are each independently a $C_{14}$-$C_{20}$ alkyl or a $C_{14}$-$C_{20}$ alkenyl.

In other embodiments of the compounds of any of formulae (II), (IIa), (IIa-1), (IIa-2), (IIa-3), (IIa-4), (IIb) and (IIb-1), $R^2$ and $R^3$ are each independently a $C_4$-$C_{10}$ alkylene-Z-$C_4$-$C_{22}$ alkyl wherein Z is —O—C(=O)—, —C(=O)—O— or —O—.

In other embodiments of the compounds of any of formulae (II), (IIa), (IIa-1), (IIa-2), (IIa-3), (IIa-4), (IIb) and (IIb-1), $R^2$ and $R^3$ are each independently a $C_4$-$C_{10}$ alkylene-Z-$C_4$-$C_{22}$ alkenyl wherein Z is —O—C(=O)—, —C(=O)—O— or —O—.

In other embodiments of the compounds of any of formulae (II), (IIa), (IIa-1), (IIa-2), (IIa-3), (IIa-4), (IIb) and (IIb-1), X' is O.

In other embodiments of the compounds of any of formulae (II), (IIa), (IIa-1), (IIa-2), (IIa-3), (IIa-4), (IIb) and (IIb-1), X' is NH.

In other embodiments of the compounds of any of formulae (II), (IIa), (IIa-1), (IIa-2), (IIa-3), (IIa-4), (IIb) and (IIb-1), Y' is NH.

In other embodiments of the compounds of any of formulae (II), (IIa), (IIa-1), (IIa-2), (IIa-3), (IIa-4), (IIb) and (IIb-1), $R^4$ and $R^5$ are each $CH_3$, or wherein $R^4$ and $R^5$ together with the nitrogen to which they are attached form a heterocyclic ring selected from the group consisting of pyrrolidinyl piperidinyl and piperazinyl, each of which is optionally substituted with an alkyl.

Specific examples of the compounds of formula (I), (Ia), (Ia-1), (II), (IIa), (IIa-1), (IIa-2), (IIa-3), (IIa-4), (IIa-5), (IIb) and (IIb-1) are compounds 1-66, the structures of which are depicted in Table 1 hereinbelow. Each possibility represents a separate embodiment of the present invention.

TABLE 1

| Compound No. | Chemical structure/Chemical name |
| --- | --- |
| 1 | 2-(1,2-di((9Z,12Z)-octadeca-9,12-dien-1-yl)hydrazinyl)-N,N-dimethylethan-1-amine |
| 2 | 4-(1,2-di((9Z,12Z)-octadeca-9,12-dien-1-yl)hydrazinyl)-N,N-dimethylbutan-1-amine |
| 3 | 1-(4-(1,2-di((9Z,12Z)-octadeca-9,12-dien-1-yl)hydrazinyl)butyl)pyrrolidine |

TABLE 1-continued

| Compound No. | Chemical structure/Chemical name |
|---|---|
| 4 | 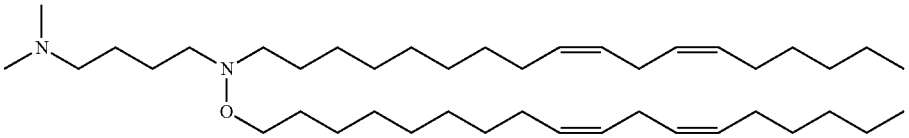<br>N,N-dimethyl-4-(((9Z,12Z)-octadeca-9,12-dien-1-yl)(((9Z,12Z)-octadeca-9,12-dien-1-yl)oxy)amino)butan-1-amine |
| 5 | 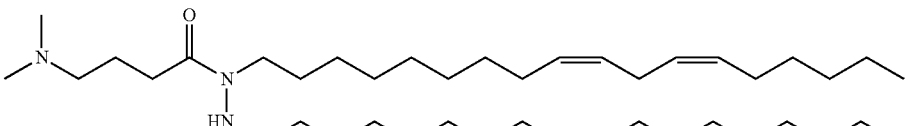<br>4-(dimethylamino)-N'-((Z)-octadec-9-en-1-yl)-N-((9Z,12Z)-octadeca-9,12-dien-1-yl)butanehydrazide |
| 6 | 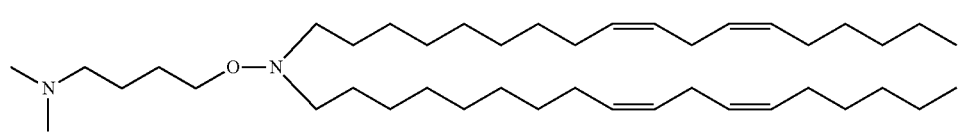<br>4-((di((9Z,12Z)-octadeca-9,12-dien-1-yl)amino)oxy)-N,N-dimethylbutan-1-amine |
| 7 | 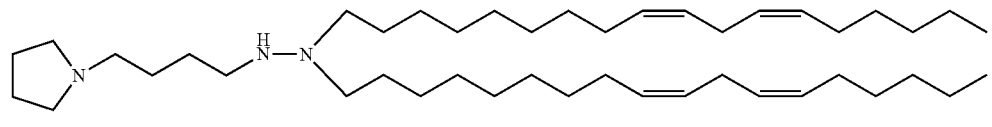<br>1-(4-(2,2-di((9Z,12Z)-octadeca-9,12-dien-1-yl)hydrazinyl)butyl)pyrrolidine |
| 8 | 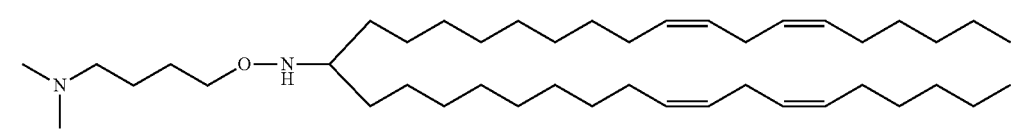<br>4-(((((6Z,9Z,28Z,31Z)-heptatriaconta-6,9,28,31-tetraen-19-yl)amino)oxy)-N,N-dimethylbutan-1-amine |
| 9 | 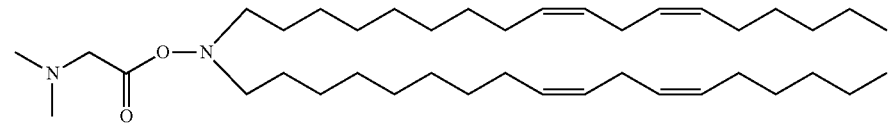<br>2-((di((9Z,12Z)-octadeca-9,12-dien-1-yl)amino)oxy)-N,N-dimethyl-2-oxoethan-1-amine |
| 10 | 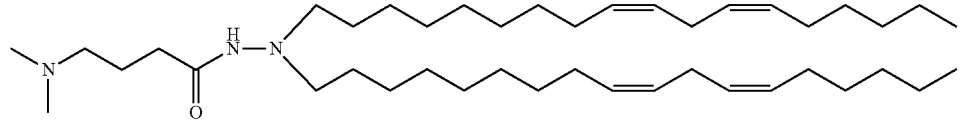<br>4-(dimethylamino)-N',N'-di((9Z,12Z)-octadeca-9,12-dien-1-yl)butanehydrazide |
| 11 | 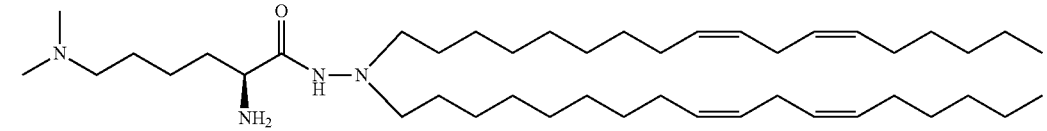<br>(S)-2-amino-6-(dimethylamino)-N',N'-di((9Z,12Z)-octadeca-9,12-dien-1-yl)hexanehydrazide |

TABLE 1-continued

| Compound No. | Chemical structure/Chemical name |
|---|---|
| 12 | 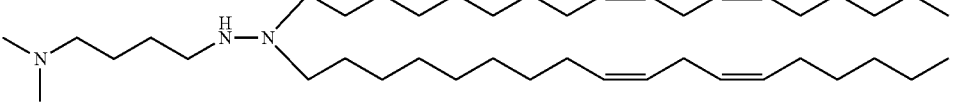<br>4-(2,2-di((9Z,12Z)-octadeca-9,12-dien-1-yl)hydrazinyl)-N,N-dimethylbutan-1-amine |
| 13 | 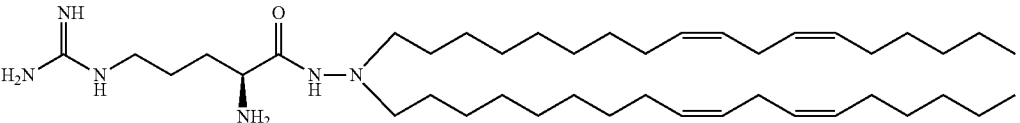<br>1-((S)-4-amino-5-(2,2-di((9Z,12Z)-octadeca-9,12-dien-1-yl)hydrazinyl)-5-oxopentyl)guanidine |
| 14 | 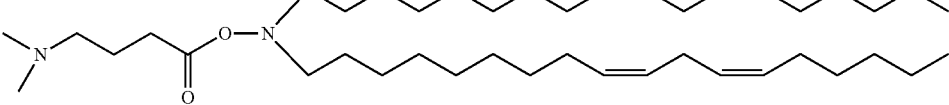<br>4-((di((9Z,12Z)-octadeca-9,12-dien-1-yl)amino)oxy)-N,N-dimethyl-4-oxobutan-1-amine |
| 15 | 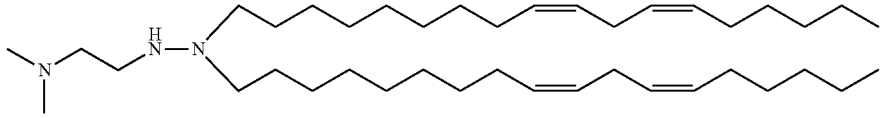<br>2-(2,2-di((9Z,12Z)-octadeca-9,12-dien-1-yl)hydrazinyl)-N,N-dimethylethan-1-amine |
| 16 | 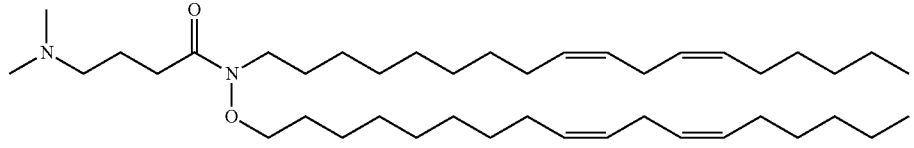<br>4-(dimethylamino)-N-((9Z,12Z)-octadeca-9,12-dien-1-yl)-N-(((9Z,12Z)-octadeca-9,12-dien-1-yl)oxy)butanamide |
| 17 | 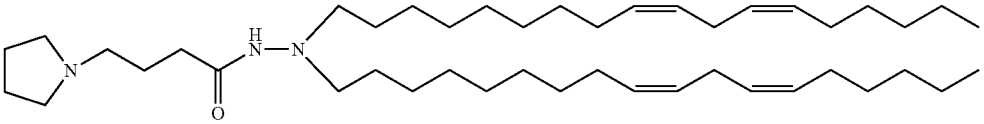<br>N',N'-di((9Z,12Z)-octadeca-9,12-dien-1-yl)-4-(pyrrolidin-1-yl)butanehydrazide |
| 18 | 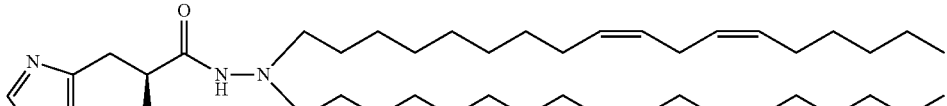<br>(S)-2-amino-3-(1H-imidazol-4-yl)-N',N'-di((9Z,12Z)-octadeca-9,12-dien-1-yl)propanehydrazide |

TABLE 1-continued

| Compound No. | Chemical structure/Chemical name |
|---|---|
| 19 | 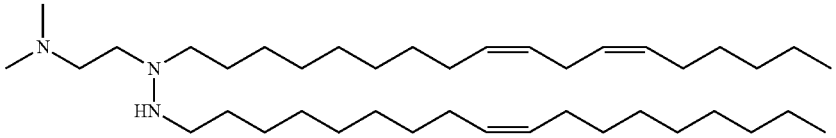
N,N-dimethyl-2-(2-((Z)-octadec-9-en-1-yl)-1-((9Z,12Z)-octadeca-9,12-dien-1-yl)hydrazinyl)ethan-1-amine |
| 20 | 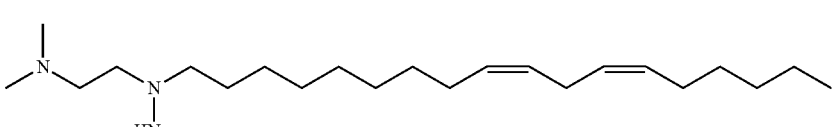
N,N-dimethyl-2-(1-((9Z,12Z)-octadeca-9,12-dien-1-yl)-2-octadecylhydrazinyl)ethan-1-amine |
| 21 | 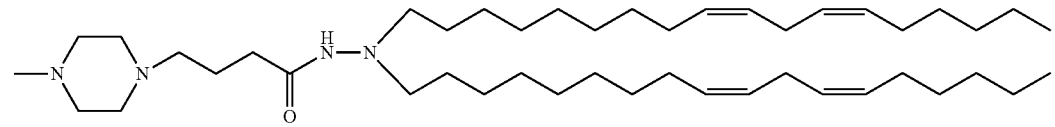
4-(4-methylpiperazin-1-yl)-N',N'-di((9Z,12Z)-octadeca-9,12-dien-1-yl)butanehydrazide |
| 22 | 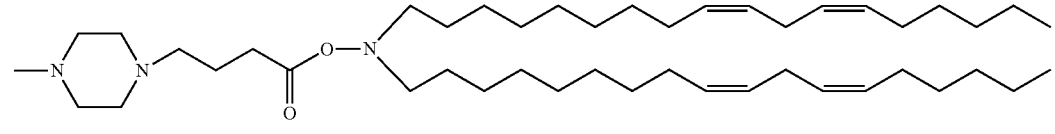
O-(4-(4-methylpiperazin-1-yl)butanoyl)-N,N-di((9Z,12Z)-octadeca-9,12-dien-1-yl)hydroxylamine |
| 23 | 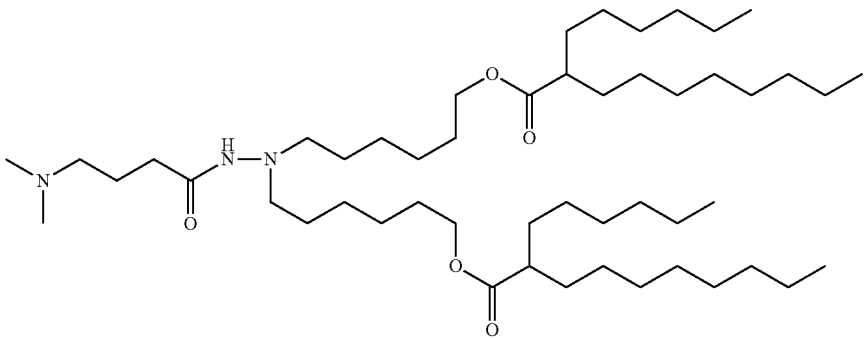
(2-(4-(dimethylamino)butanoyl)hydrazine-1,1-diyl)bis(hexane-6,1-diyl) bis(2-hexyldecanoate) |

TABLE 1-continued

| Compound No. | Chemical structure/Chemical name |
|---|---|
| 24 | 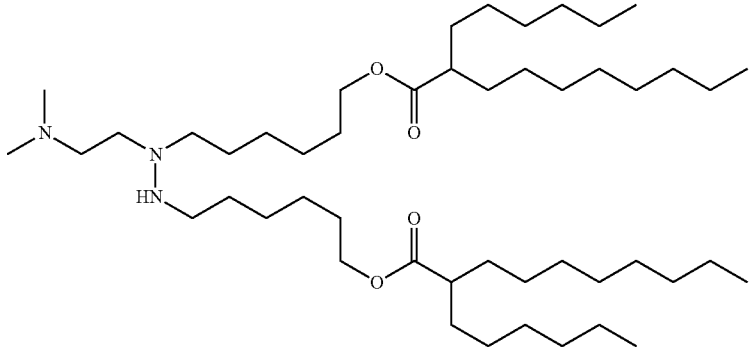<br>(1-(2-(dimethylamino)ethyl)hydrazine-1,2-diyl)bis(hexane-6,1-diyl) bis(2-hexyldecanoate) |
| 25 | 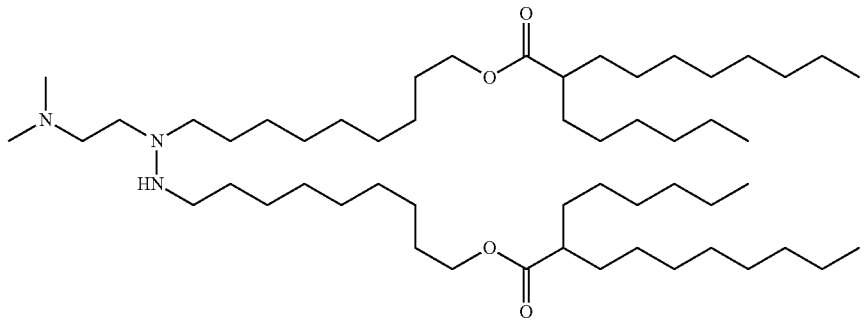<br>(1-(2-(dimethylamino)ethyl)hydrazine-1,2-diyl)bis(nonane-9,1-diyl) bis(2-hexyldecanoate) |
| 26 | 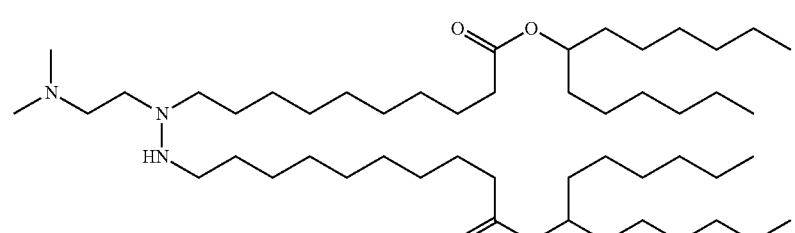<br>di(tridecan-7-yl) 10,10'-(1-(2-(dimethylamino)ethyl)hydrazine-1,2-diyl)bis(decanoate) |
| 27 | 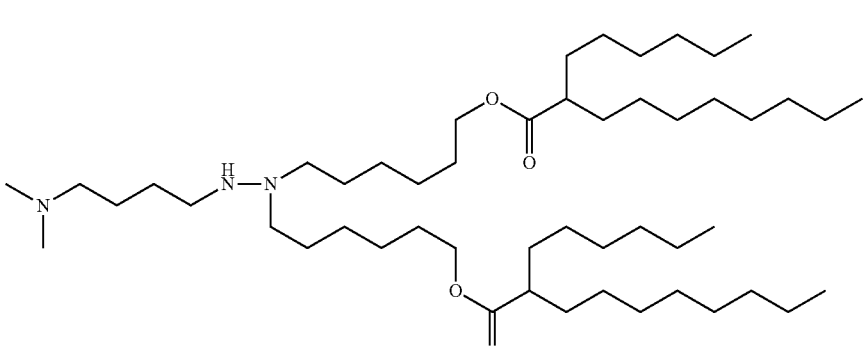<br>(2-(4-(dimethylamino)butyl)hydrazine-1,1-diyl)bis(hexane-6,1-diyl) bis(2-hexyldecanoate) |

TABLE 1-continued

| Compound No. | Chemical structure/Chemical name |
|---|---|
| 28 | (2-(4-(dimethylamino)butyl)hydrazine-1,1-diyl)bis(nonane-9,1-diyl) bis(2-hexyldecanoate |
| 29 | ((4-(dimethylamino)butoxy)azanediyl)bis(hexane-6,1-diyl) bis(2-hexyldecanoate) |
| 30 | ((4-(dimethylamino)butoxy)azanediyl)bis(nonane-9,1-diyl) bis(2-hexyldecanoate) |
| 31 | 2-(1H-imidazol-4-yl)-N',N'-di((9Z,12Z)-octadeca-9,12-dien-1-yl)acetohydrazide |
| 32 | 1-(2-(2,2-di((9Z,12Z)-octadeca-9,12-dien-1-yl)hydrazinyl)ethyl)guanidine |

TABLE 1-continued

| Compound No. | Chemical structure/Chemical name |
|---|---|
| 33 | 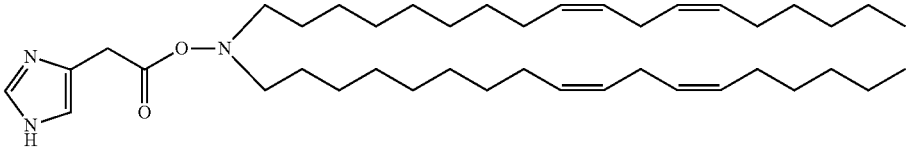<br>O-(2-(1H-imidazol-4-yl)acetyl)-N,N-di((9Z,12Z)-octadeca-9,12-dien-1-yl)hydroxylamine |
| 34 | 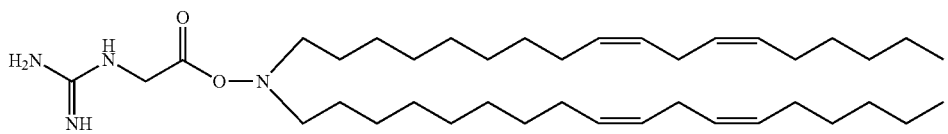<br>1-(2-((di((9Z,12Z)-octadeca-9,12-dien-1-yl)amino)oxy)-2-oxoethyl)guanidine |
| 35 | 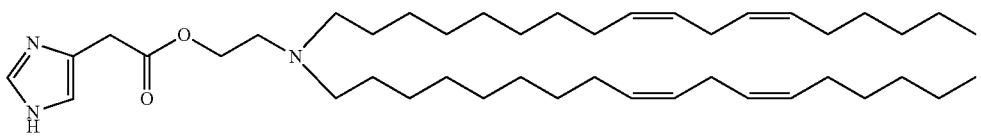<br>2-(di((9Z,12Z)-octadeca-9,12-dien-1-yl)amino)ethyl 2-(1H-imidazol-4-yl)acetate |
| 36 | 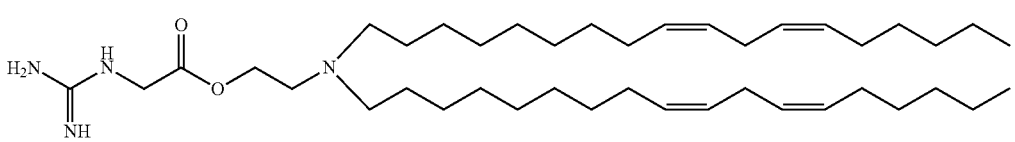<br>2-(di((9Z,12Z)-octadeca-9,12-dien-1-yl)amino)ethyl carbamimidoylglycinate |
| 37 | 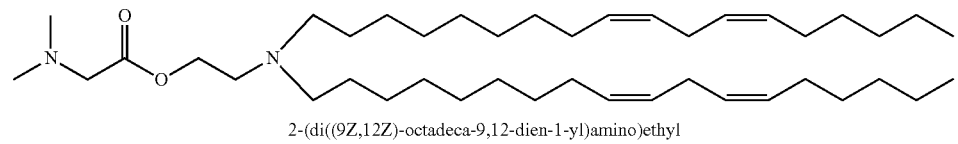<br>2-(di((9Z,12Z)-octadeca-9,12-dien-1-yl)amino)ethyl dimethylglycinate |
| 38 | 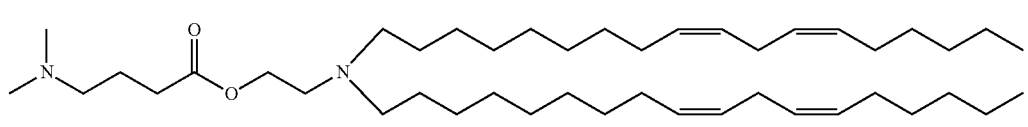<br>2-(di((9Z,12Z)-octadeca-9,12-dien-1-yl)amino)ethyl 4-(dimethylamino)butanoate |
| 39 | 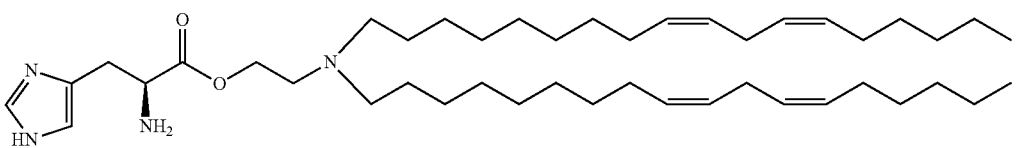<br>2-(di((9Z,12Z)-octadeca-9,12-dien-1-yl)amino)ethyl L-histidinate |

TABLE 1-continued

| Compound No. | Chemical structure/Chemical name |
|---|---|
| 40 | 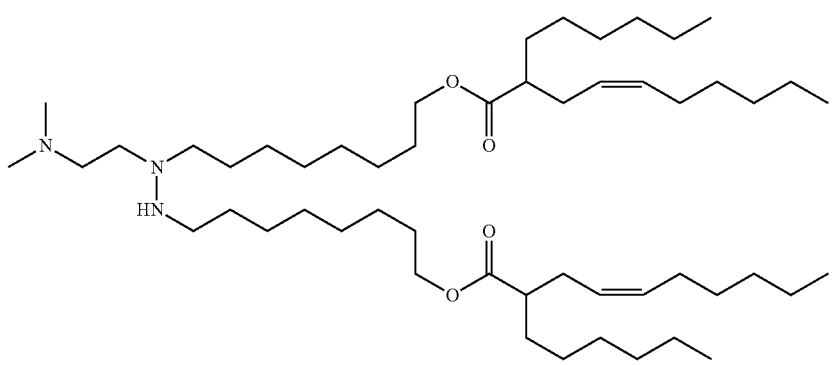<br>(1-(2-(dimethylamino)ethyl)hydrazine-1,2-diyl)bis(octane-8,1-diyl)(4Z,4'Z)-bis(2-hexyldec-4-enoate) |
| 41 | 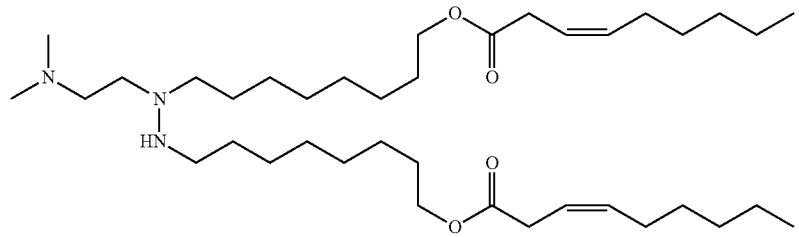<br>(1-(2-(dimethylamino)ethyl)hydrazine-1,2-diyl)bis(octane-8,1-diyl)(3Z,3'Z)-bis(non-3-enoate) |
| 42 | 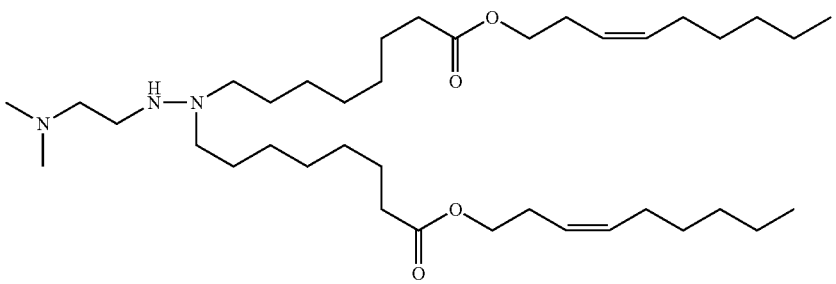<br>di((Z)-non-3-en-1-yl) 8,8'-(2-(2-(dimethylamino)ethyl)hydrazine-1,1-diyl)dioctanoate |
| 43 | 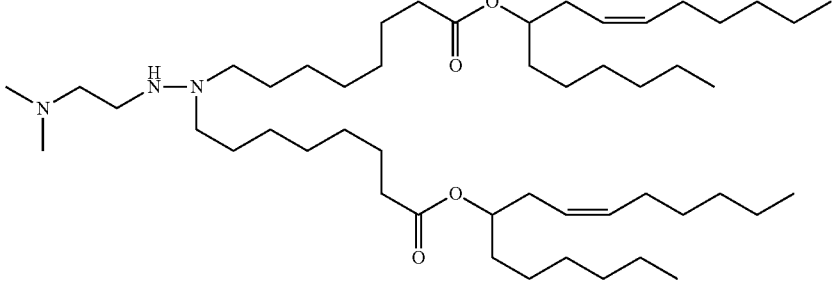<br>di((Z)-pentadec-9-en-7-yl) 8,8'-(2-(2-(dimethylamino)ethyl)hydrazine-1,1-diyl)dioctanoate |

TABLE 1-continued

| Compound No. | Chemical structure/Chemical name |
|---|---|
| 44 | di((Z)-pentadec-9-en-7-yl) 8,8'-(((4-(dimethylamino)butanoyl)oxy)azanediyl)dioctanoate |
| 45 | di((Z)-non-3-en-1-yl) 8,8'-(((4-(dimethylamino)butanoyl)oxy)azanediyl)dioctanoate |
| 46 | di((Z)-pentadec-9-en-7-yl) 8,8'-(2-(((2-(dimethylamino)ethyl)thio)carbonyl)hydrazine-1,1-diyl)dioctanoate |
| 47 | di(tridecan-7-yl) 8,8'-(2-(((2-(dimethylamino)ethyl)thio)carbonyl)hydrazine-1,1-diyl)dioctanoate |

TABLE 1-continued

| Compound No. | Chemical structure/Chemical name |
|---|---|
| 48 | 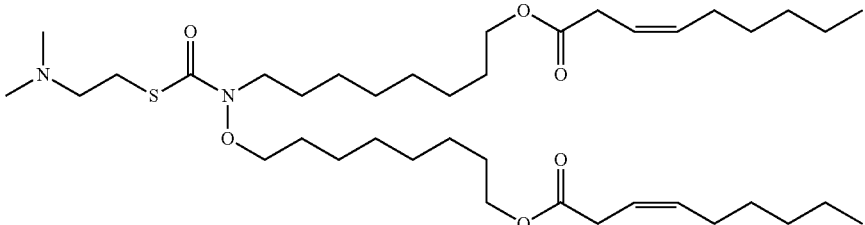<br>8-(((((2-(dimethylamino)ethyl)thio)carbonyl)((8-(((Z)-non-3-enoyl)oxy)octyl)oxy)amino)octyl (Z)-non-3-enoate |
| 49 | 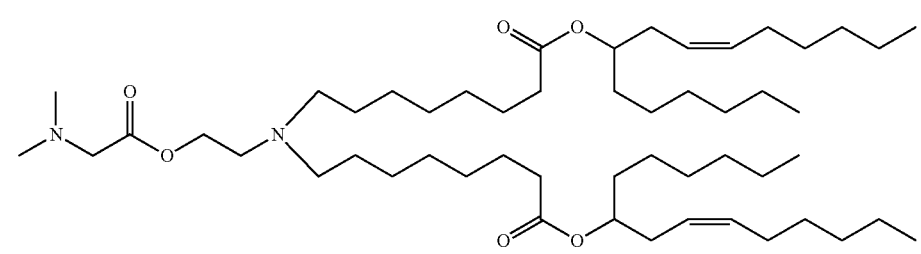<br>di((Z)-pentadec-9-en-7-yl) 8,8'-((2-((dimethylglycyl)oxy)ethyl)azanediyl)dioctanoate |
| 50 | 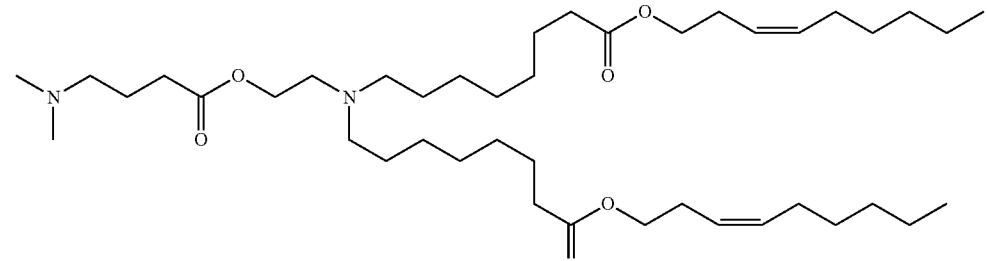<br>di((Z)-non-3-en-1-yl) 8,8'-((2-((4-(dimethylamino)butanoyl)oxy)ethyl)azanediyl)dioctanoate |
| 51 | 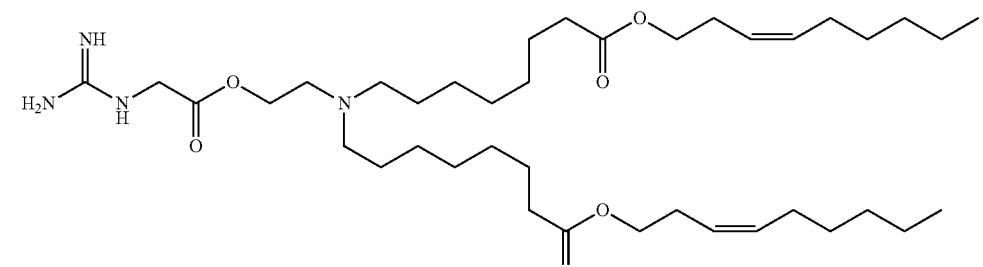<br>di((Z)-non-3-en-1-yl) 8,8'-((2-((carbamimidoylglycyl)oxy)ethyl)azanediyl)dioctanoate |
| 52 | 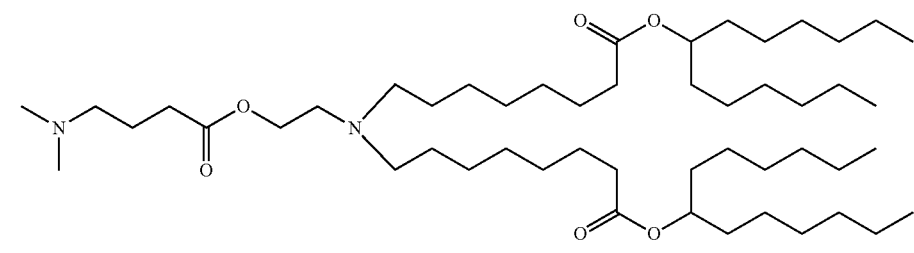<br>di(tridecan-7-yl) 8,8'-((2-((4-(dimethylamino)butanoyl)oxy)ethyl)azanediyl)dioctanoate |

TABLE 1-continued

| Compound No. | Chemical structure/Chemical name |
|---|---|
| 53 | 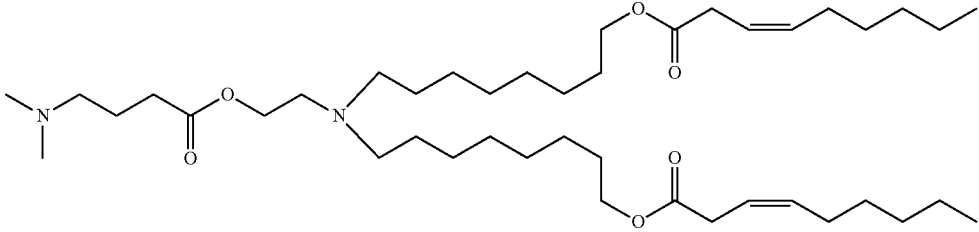<br>((2-((4-(dimethylamino)butanoyl)oxy)ethyl)azanediyl)bis(octane-8,1-diyl) (3Z,3′Z)-bis(non-3-enoate) |
| 54 | 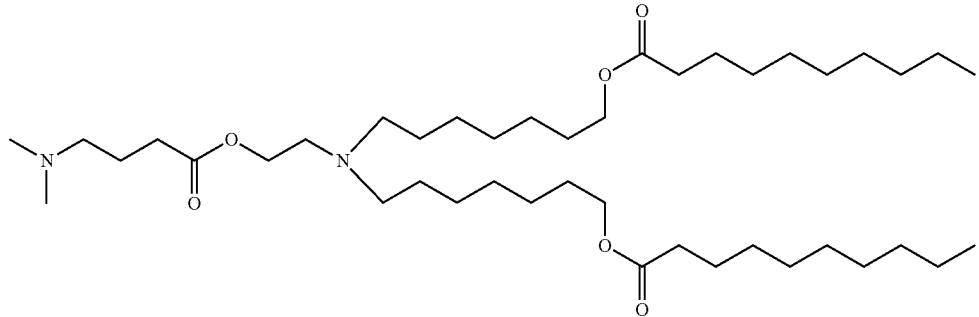<br>((2-((4-(dimethylamino)butanoyl)oxy)ethyl)azanediyl)bis(heptane-7,1-diyl)bis(decanoate) |
| 55 | 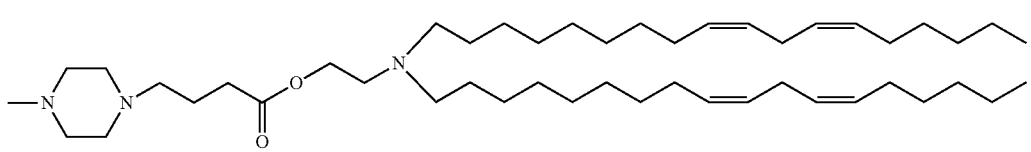<br>2-(di((9Z,12Z)-octadeca-9,12-dien-1-yl)amino)ethyl 4-(4-methylpiperazin-1-yl)butanoate |
| 56 | 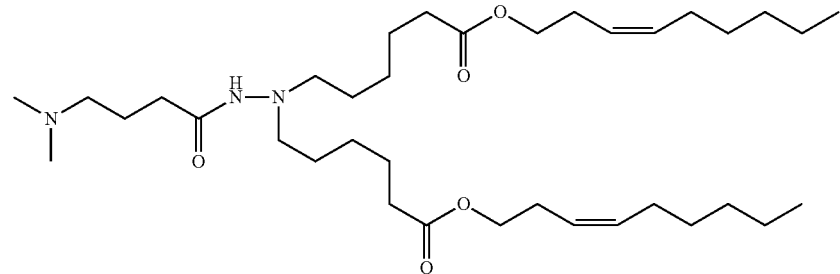<br>di((Z)-non-3-en-1-yl) 6,6′-(2-(4-(dimethylamino)butanoyl)hydrazine-1,1-diyl)dihexanoate |

TABLE 1-continued

| Compound No. | Chemical structure/Chemical name |
|---|---|
| 57 | 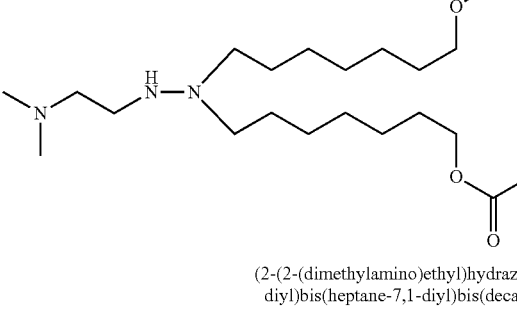
(2-(2-(dimethylamino)ethyl)hydrazine-1,1-diyl)bis(heptane-7,1-diyl)bis(decanoate) |
| 58 | 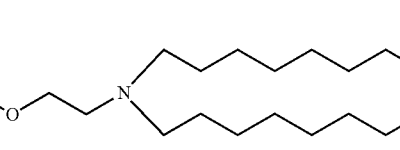
(9Z,12Z)-N-(2-(4-(dimethylamino)butoxy)ethyl)-N-((9Z,12Z)-octadeca-9,12-dien-1-yl)octadeca-9,12-dien-1-amine |
| 59 | 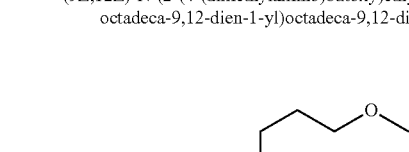
4-(dimethylamino)-N',N'-bis(6-(((Z)-non-3-en-1-yl)oxy)hexyl)butanehydrazide |
| 60 | 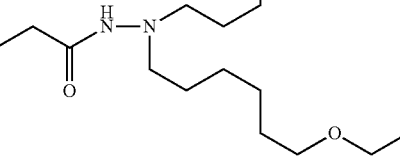
2-(di((9Z,12Z)-octadeca-9,12-dien-1-yl)amino)ethyl 4-(pyrrolidin-1-yl)butanoate |
| 61 | 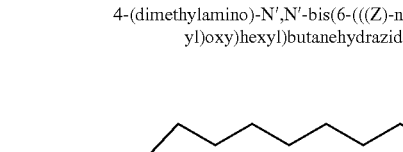
N-(2-(4-(dimethylamino)butoxy)ethyl)-6-(((Z)-non-3-en-1-yl)oxy)-N-(6-(((Z)-non-3-en-1-yl)oxy)hexyl)hexan-1-amine |

TABLE 1-continued

| Compound No. | Chemical structure/Chemical name |
|---|---|
| 62 | ((2-(4-(dimethylamino)butoxy)ethyl)azanediyl)bis(heptane-7,1-diyl)bis(decanoate) |
| 63 | di((Z)-non-3-en-1-yl) 6,6'-((2-(4-(dimethylamino)butoxy)ethyl)azanediyl)dihexanoate |
| 64 (intermediate) | 2-(di((9Z,12Z)-octadeca-9,12-dien-1-yl)amino)ethan-1-ol |
| 65 (intermediate) | di((Z)-non-3-en-1-yl) 6,6'-((2-hydroxyethyl)azanediyl)dihexanoate |
| 66 (intermediate) | ((2-hydroxyethyl)azanediyl)bis(heptane-7,1-diyl)bis(decanoate) |

In another aspect, the cationic lipid of the present invention is represented by the structure of formula (III):

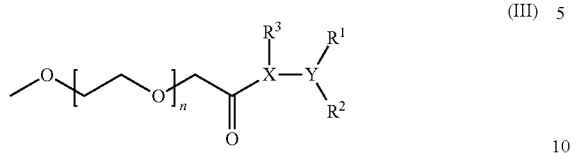

(III)

wherein
X and Y are each independently O, N or NH, wherein X and Y cannot both be O;
each of $R^1$, $R^2$ and $R^3$ is independently absent or a $C_{10}$-$C_{22}$ alkyl, a $C_{10}$-$C_{22}$ alkenyl or a $C_{10}$-$C_{22}$ alkynyl; and
n is an integer between 1 and 30;
including salts, hydrates, solvates, polymorphs, optical isomers, geometrical isomers, enantiomers, diastereomers, and mixtures thereof.

In another aspect, the cationic lipid of the present invention is represented by the structure of formula (IIIA):

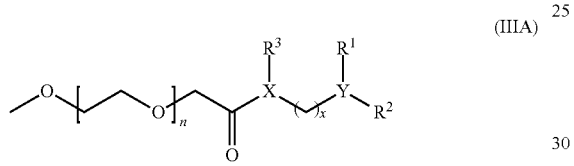

(IIIA)

wherein
X and Y are each independently O, N or NH, wherein X and Y cannot both be O;
each of $R^1$, $R^2$ and $R^3$ is independently absent or a $C_{10}$-$C_{22}$ alkyl, a $C_{10}$-$C_{22}$ alkenyl or a $C_{10}$-$C_{22}$ alkynyl;
n is an integer between 1 and 30; and
x is 0 or 2;
including salts, hydrates, solvates, polymorphs, optical isomers, geometrical isomers, enantiomers, diastereomers, and mixtures thereof.

In some embodiments of formula (III) or (IIIA), X and Y are each independently selected from the group consisting of O and N. In other embodiments of formula (III), X and Y are each independently selected from the group consisting of O, N and NH.

Specific examples of the compounds of formula (III) are compounds 67-70, the structures of which are depicted in Table 2.

TABLE 2

| Compound No. | Chemical structure/Chemical name |
|---|---|
| 67 | 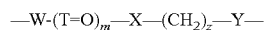 |
| 68 | |
| 69 | |
| 70 | | where n is as defined above for formula (III) or (IIIA).

Additional Embodiments of the Present Invention

In further embodiments, the present invention relates to a cationic lipid comprising a functional group represented by the structure:

—W-(T=O)$_m$—X—(CH$_2$)$_z$—Y— wherein
X and Y are each independently O or N, wherein X and Y cannot both be O;
W is a bond, O, NH or S;
T is C or S;
m is 0 or 1; and
z is 0 or 2;
wherein the functional group is linked to at least one saturated or unsaturated fatty acid residue.

In some embodiments, the cationic lipid comprises two fatty acid residues symmetrically or asymmetrically linked to the aforementioned functional group.

In one aspect of the present invention, the cationic lipid is represented by the structure of formula (I'):

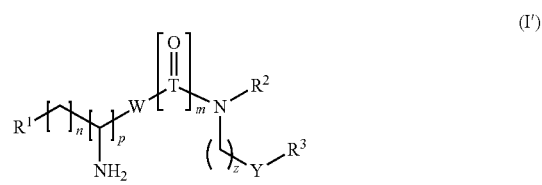

(I')

wherein
Y is O or NH;
T is C or S;
W is a bond, O, NH or S;
$R^1$ is selected from the group consisting of:
(a) NR$^4$R$^5$ wherein R$^4$ and R$^5$ are each independently a $C_1$-$C_4$ alkyl; or R$^4$ and R$^5$ together with the nitrogen to which they are attached form a 5 or 6 membered heterocyclic or heteroaromatic ring, optionally containing one or more heteroatoms selected from O, N and S; or NR$^4$R$^5$ represent a guanidine group (—NHC(=NH)NH$_2$);
(b) the side chain of a natural or unnatural amino acid; and
(c) a 5 or 6 membered heterocyclic or heteroaromatic ring containing one or more heteroatoms selected from O, N and S;

$R^2$ and $R^3$ are selected from the group consisting of:
(a) a $C_{10}$-$C_{22}$ alkyl, a $C_{10}$-$C_{22}$ alkenyl or a $C_{10}$-$C_{22}$ alkynyl; and
(b) $C_4$-$C_{10}$ alkylene-Z—$C_4$-$C_{22}$ alkyl wherein Z is —O—C(=O)— or —C(=O)—O;

n is 0, 1, 2, 3, 4, 5 or 6;
m is 0 or 1;
p is 0 or 1; and
z is 0 or 2;
including salts, hydrates, solvates, polymorphs, optical isomers, geometrical isomers, enantiomers, diastereomers, and mixtures thereof.

In some embodiments, the compound of formula (I') comprises a functional group selected from hydrazine, hydroxylamine and hydrazide. Each possibility represents a separate embodiment of the present invention.

In some embodiments of formula (I'), m is 0. In other embodiments of formula (I'), m is 1. In other embodiments of formula (I'), p is 0. In other embodiments of formula (I'), p is 1. In other embodiments of formula (I'), m is 0 and p is 0. In other embodiments of formula (I'), m is 1 and p is 0. In other embodiments of formula (I'), z is 0. In other embodiments of formula (I'), z is 2. In other embodiments of formula (I'), T is C. In other embodiments of formula (I'), W is a bond. In other embodiments of formula (I'), $R^1$ is $NR^4R^5$.

In some representative embodiments of formula (I'), p is 0, W is a bond and T is C, and the compound is represented by the structure of formula (Ia'):

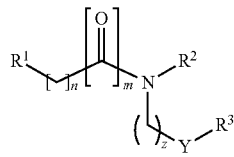

(Ia')

wherein $R^1$, $R^2$, $R^3$, Y, m, n and z are as defined in formula (I'). In some embodiments of formula (Ia'), m is 0. In other embodiments of formula (Ia'), m is 1. In other embodiments of formula (Ia'), z is 0. In other embodiments of formula (Ia'), $R^2$ and $R^3$ are each independently a $C_{14}$-$C_{20}$ alkyl or a $C_{14}$-$C_{20}$ alkenyl. In other embodiments of formula (Ia'), $R^2$ and $R^3$ are each independently a $C_4$-$C_{10}$ alkylene-Z—$C_4$-$C_{22}$ alkyl wherein Z is —O—C(=O)— or —C(=O)—O—. In other embodiments of formula (Ia), Y is O. In other embodiments of formula (Ia'), Y is NH.

In other representative embodiments of formula (I'), $R^1$ is $NR^4R^5$, and the compound is represented by the structure of formula (Ia-1'):

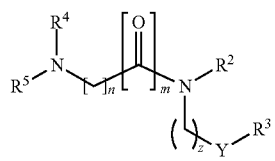

(Ia-1')

wherein $R^2$, $R^3$, $R^4$, $R^5$, Y, m, n and z are as defined in formula (I). In some embodiments of formula (Ia-1'), $R^4$ and $R^5$ are each $CH_3$. In other embodiments of formula (Ia-1'), $R^4$ and $R^5$ together with the nitrogen to which they are attached form a heterocyclic ring selected from pyrrolidinyl piperidininyl and piperazinyl, each of which is optionally substituted with an alkyl. Each possibility represents a separate embodiment of the present invention. In another aspect of the present invention, the cationic lipid is represented by the structure of formula (II'):

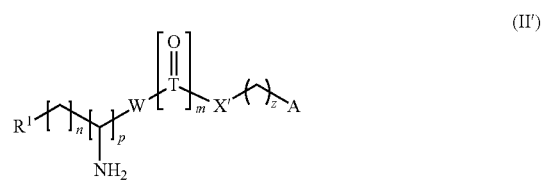

(II')

wherein
A is

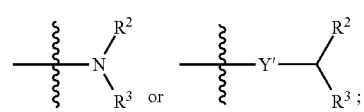

X' is O or NH;
Y' is O or NH;
provided that when A is

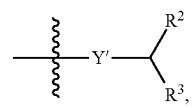

X' and Y' cannot both be O;
T is C or S;
W is a bond, O, NH or S;
$R^1$ is selected from the group consisting of:
(a) $NR^4R^5$ wherein $R^4$ and $R^5$ are each independently a $C_1$-$C_4$ alkyl; or $R^4$ and $R^5$ together with the nitrogen to which they are attached form a 5 or 6 membered heterocyclic or heteroaromatic ring, optionally containing one or more heteroatoms selected from O, N and S; or $NR^4R^5$ represent a guanidine group (—NHC(=NH)$NH_2$);
(b) the side chain of a natural or unnatural amino acid; and
(c) a 5 or 6 membered heterocyclic or heteroaromatic ring containing one or more heteroatoms selected from O, N and S;
$R^2$ and $R^3$ are selected from the group consisting of:
(a) a $C_{10}$-$C_{22}$ alkyl, a $C_{10}$-$C_{22}$ alkenyl or a $C_{10}$-$C_{22}$ alkynyl; and
(b) $C_4$-$C_{10}$ alkylene-Z—$C_4$-$C_{22}$ alkyl wherein Z is —O—C(=O)— or —C(=O)—O;
n is 0, 1, 2, 3, 4, 5 or 6;
m is 0 or 1;
p is 0 or 1; and
z is 0 or 2;
including salts, hydrates, solvates, polymorphs, optical isomers, geometrical isomers, enantiomers, diastereomers, and mixtures thereof.

In some embodiments, the compound of formula (II') comprises a functional group selected from hydrazine, hydroxylamine and hydrazide. Each possibility represents a separate embodiment of the present invention.

In some embodiments of formula (II'), m is 0. In other embodiments of formula (I), m is 1. In other embodiments of formula (II'), m is 1. In other embodiments of formula (I), m is 1 and p is 0. In other embodiments of formula (II'), z is 0. In other embodiments of formula (II'), z is 2. In other embodiments of formula (II'), T is C. In other embodiments of formula (II'), W is a bond.

In some representative embodiments of formula (II'), the cationic lipid is represented by the structure of formula (IIa)':

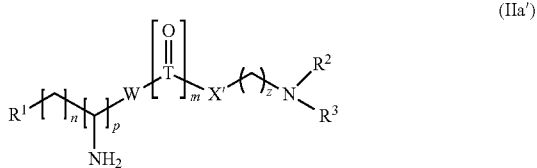

wherein $R^1$, $R^2$, $R^3$, X', T, W, n, m, p and z are as defined in formula (II').

In some embodiments of formula (IIa') p is 0, W is a bond and T is C, and the compound is represented by the structure of formula (IIa-1'):

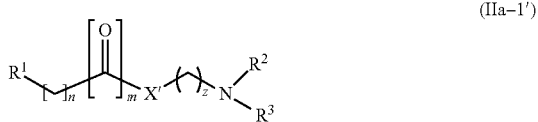

wherein $R^1$, $R^2$, $R^3$, X', n, m and z are as defined in formula (II').

In other embodiments of formula (IIa'), $R^1$ is $NR^4R^5$, and the compound is represented by the structure of formula (IIa-2'):

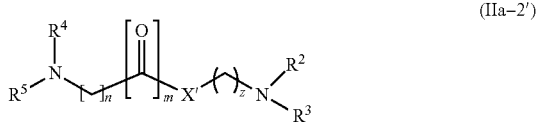

wherein $R^2$, $R^3$, $R^4$, $R^5$, X', n, m and z are as defined in formula (II').

In yet other embodiments of formula (IIa'), p is 1, m is 1, W is a bond and T is C, and the compound is represented by the structure of formula (IIa-3'):

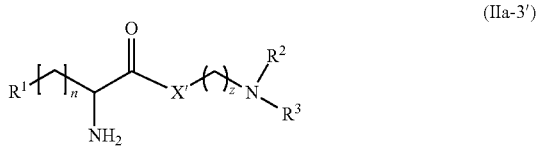

wherein $R^1$ is the side chain of a natural or unnatural amino acid; and $R^1$, $R^2$, $R^3$, X', n and z are as defined in formula (II).

In other representative embodiments of formula (II'), the cationic lipid is represented by the structure of formula (IIb'):

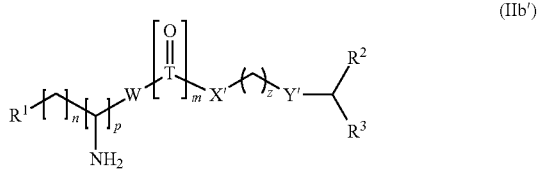

wherein $R^1$, $R^2$, $R^3$, T, W, X', Y' n, m, p and z are as defined in formula (II').

In some representative embodiments of formula (IIb'), p is 0, W is a bond, T is C, and $R^1$ is $NR^4R^5$, and the compound is represented by the structure of formula (IIb-1'):

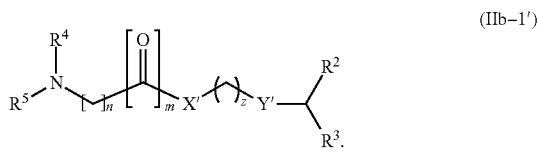

wherein $R^2$, $R^3$, $R^4$, $R^5$, X', Y', n, m and z are as defined in formula (II').

In some embodiments of the compounds of any of formulae (II'), (IIa'), (IIa-1'), (IIa-2'), (IIa-3'), (IIb') and (IIb-1'), $R^2$ and $R^3$ are each independently a $C_{14}$-$C_{20}$ alkyl or a $C_{14}$-$C_{20}$ alkenyl.

In other embodiments of the compounds of any of formulae (II'), (IIa'), (IIa-1'), (IIa-2'), (IIa-3'), (IIb') and (IIb-1'), $R^2$ and $R^3$ are each independently a $C_4$-$C_{10}$ alkylene-Z—$C_4$-$C_{22}$ alkyl wherein Z is —O—C(=O)— or —C(=O)—O—.

In other embodiments of the compounds of any of formulae (II'), (IIa'), (IIa-1'), (IIa-2'), (IIa-3'), (IIb') and (IIb-1'), X' is O.

In other embodiments of the compounds of any of formulae (II'), (IIa'), (IIa-1'), (IIa-2'), (IIa-3'), (IIb') and (IIb-1'), X' is NH.

In other embodiments of the compounds of any of formulae (II'), (IIa'), (IIa-1'), (IIa-2'), (IIa-3'), (IIb') and (IIb-1'), Y' is NH.

In other embodiments of the compounds of any of formulae (II'), (IIa'), (IIa-1'), (IIa-2'), (IIa-3'), (IIb') and (IIb-1'), $R^4$ and $R^5$ are each $CH_3$, or wherein $R^4$ and $R^5$ together with the nitrogen to which they are attached form a heterocyclic ring selected from pyrrolidinyl piperidinyl, piperazinyl, each of which is optionally substituted with an alkyl.

In another aspect, the cationic lipid of the present invention is represented by the structure of formula (III'):

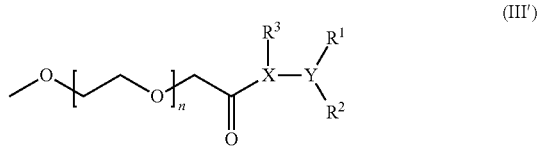

wherein
X and Y are each independently is O or N;
each of $R^1$, $R^2$ and $R^3$ is independently absent or a $C_{10}$-$C_{22}$ alkyl, a $C_{10}$-$C_{22}$ alkenyl or a $C_{10}$-$C_{22}$ alkynyl; and
n is 1 to 30;

including salts, hydrates, solvates, polymorphs, optical isomers, geometrical isomers, enantiomers, diastereomers, and mixtures thereof.

Chemical Definitions

An "alkyl" group refers to any saturated aliphatic hydrocarbon, including straight-chain and branched-chain alkyl groups. In one embodiment, the alkyl group has 1-4 carbons designated here as $C_1$-$C_4$-alkyl. In another embodiment, the alkyl group has 10-22 carbons designated here as $C_{10}$-$C_{22}$-alkyl. In another embodiment, the alkyl group has 4-10 carbons designated here as $C_4$-$C_{10}$-alkyl. In another embodiment, the alkyl group has 4-22 carbons designated here as $C_4$-$C_{22}$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkenyl" group refers to an aliphatic hydrocarbon group containing at least one carbon-carbon double bond including straight-chain, branched-chain and cyclic alkenyl groups. In one embodiment, the alkenyl group has 10-22 carbons designated here as $C_{10}$-$C_{22}$-alkenyl. In another embodiment, the alkenyl group has 4-10 carbons designated here as $C_4$-$C_{10}$-alkenyl. In another embodiment, the alkenyl group has 4-22 carbons designated here as $C_4$-$C_{22}$-alkenyl. Exemplary alkenyl groups include ethenyl, propenyl, n-butenyl, i-butenyl, 3-methylbut-2-enyl, n-pentenyl, heptenyl, octenyl, cyclohexyl-butenyl and decenyl. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 10-22 carbons designated here as $C_{10}$-$C_{22}$-alkynyl. In another embodiment, the alkynyl group has 4-10 carbons designated here as $C_4$-$C_{10}$-alkynyl. In another embodiment, the alkynyl group has 4-22 carbons designated here as $C_4$-$C_{22}$-alkynyl. Exemplary alkynyl groups include ethynyl, propynyl, n-butynyl, 2-butynyl, 3-methylbutynyl, n-pentynyl, heptynyl, octynyl and decynyl. The alkynyl group can be unsubstituted or substituted through available carbon atoms with one or more groups defined hereinabove for alkyl.

The term "heteroaryl" used herein alone or as part of another group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. If nitrogen is a ring atom, the present invention also contemplates the N-oxides of the nitrogen containing heteroaryls. Non-limiting examples of heteroaryl moieities include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group refers to a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic ring moieties include piperidinyl, pyrrolidinyl piperazinyl, pyrrolinyl, pyrazolinyl, pyrazolidinyl, morpholinyl, thiomorpholinyl, pyranyl, thiopyranyl, indolinyl, dihydrofuranyl, tetrahydrofuranyl, dihydrothiophenyl, tetrahydrothiophenyl, dihydropyranyl, tetrahydropyranyl, dihydrothiazolyl, and the like. In some embodiments, the cyclic group is pyrrolidinyl. In other embodiments, the heteroaryl or heterocyclyl group is piperidinyl. In other embodiments, the heterocyclyl group is piperidine. The heterocyclyl group can be unsubstituted or substituted through available atoms with one or more groups defined hereinabove for alkyl.

As used herein in the specification and in the claims section below the term "amino acid" or "amino acids" is understood to include the 20 naturally occurring amino acids, i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Each possibility represents a separate embodiment of the invention. According to other embodiments, the term amino acids refers to non-natural amino acids or synthetic amino acids.

Furthermore, the term "amino acid" includes both D- and L-amino acids. According to the principles of the present invention, the term "amino acid side chain" refers to a group "R" of an amino acid of the formula $H_2N$—C(R)—COOH.

The term "hydrazine" moiety refers to the group "—NH—NH—"

The term "hydroxylamine" moiety as used herein refers to the group "—NH—O—"

The term "hydrazide" moiety as used herein refers to the group "—C(=O)—N—N"

The term "hydroxylamine" moiety as used herein refers to the group "—O—$CH_2$—$CH_2$—N—" or "—N—$CH_2$—$CH_2$—O—"

The term "ethylenediamine" moiety as used herein refers to the group "—N—$CH_2$—$CH_2$—N—" or "—N—$CH_2$—$CH_2$—N—"

The term "guanidine" as used herein refers to the group —NHC(=NH)$NH_2$.

The term "leaving group" as used herein refers to any labile leaving group with is readily replaced by another moiety. In some embodiments, the leaving group is selected from the group consisting of halogen, sulfonyloxy and —OC(O)R' wherein R' is an alkyl, aryl or alkylaryl. In some preferred embodiments, the leaving group is selected from the group consisting of Cl, Br, I, mesylate (OMs), triflate (OTr) and tosylate (OTs). In a currently preferred embodiment, the leaving group X is Br. Each possibility represents a separate embodiment of the present invention.

The term "protecting group" refers to chemical residues used to block reactive sites during chemical synthesis, that enable chemical reaction to be carried out selectively at one reaction site in a multifunctional compound, other reactive sites must be temporarily blocked. The residues used to block these reactive sites called protecting groups.

The term "nitrogen protecting group" or "N protecting group" or "amino protecting group" as used herein interchangeably refers to refers to a readily cleavable group bonded to amino groups. Examples of amino-protecting groups include t-butoxycarbonyl (BOC), benzyloxycarbonyl, acetyl, phenylcarbonyl, or a silyl group, which can be substituted with alkyl (trialkylsilyl), with an aryl (triarylsilyl) or a combination thereof (e.g., dialkylphenylsilyl), e.g., trimethylsilyl (TMS) or t-butyldimethyl silyl (TBDMS). Other examples of hydroxy protecting groups include, for example, $C_1$-$C_4$ alkyl (e.g., methyl, ethyl, propyl, butyl and the like), —$CH_2Ph$ (benzyl or bzl), allyl (All), (allyl)-CO—($C_1$-$C_6$ alkyl), —$SO_2$—($C_1$-$C_6$ alkyl), —$SO_2$-aryl, —CO—Ar in which Ar is an aryl group as defined above, and —CO—($C_1$-$C_6$ alkyl)Ar (e.g., a carboxybenzyl (Bz) group). Other examples of hydroxy protecting groups include acid sensitive protecting groups such as tetrahydropyranyl (THP), methoxymethyl (MOM), triphenylmethyl (Trityl) and dimethoxy trityl (DMT). Each possibility represents a separate embodiment of the present invention. Protecting groups can be removed by applying deprotecting agents as known in the art. Methods of incorporation and deprotection, are described by C. B. Reese and E. Haslam, "Protective Groups in Organic Chemistry," J. G. W. McOmie, Ed., Plenum Press, New York, NY, 1973, Chapters 3 and 4, respectively, and T. W. Greene and P. G. M. Wuts, "Protective Groups in Organic Synthesis," 2nd ed., John Wiley and Sons, New York, NY, 1991 and A. J. Pearson and W. R. Roush, Activating Agents and Protecting Groups, John Wiley and Sons (1999), the contents of each of which are incorporated by reference in their entirety. According some embodiments, pharmaceutically acceptable salts includes both 'acid' and 'base' addition salts, which retain the biologically effectiveness of the acid or base.

One or more of the cationic lipids of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the invention.

The term "organic or inorganic cation" refers to counter-ions for the anion of a salt. The counter-ions include, but are not limited to, alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.* (1977), 66:1-19, which is incorporated herein by reference.

Compositions and Therapeutic Uses

In some aspects, the present invention provides a composition comprising a cationic lipid according to any one of formulae (I), (Ia), (Ia-1), (II), (IIa), (IIa-1), (IIa-2), (IIa-3), (IIa-4), (IIb) and (IIb-1), e.g., any one of compounds 1 to 66, and a pharmaceutically acceptable excipient. The composition may further comprise comprising at least one additional neutral or PEG-modified lipid.

In some embodiments, the composition may further comprise a nucleic acid. Examples of nucleic acids include small interfering RNA (siRNA), micro RNA (miRNA), antisense oligo nucleotides, messenger RNA (mRNA), ribozymes, pDNA, CRISPR mRNA, gRNA and immune stimulating nucleic acids. Each possibility represents a separate embodiment of the present invention.

In some embodiments, the present invention provides a method of gene silencing, comprising the step of contacting a cell with a composition comprising a cationic lipid of the present invention. In some embodiments, the cell is a cancer cell.

In other embodiments, the composition further comprises one or more components selected from the group consisting of a neutral lipid, a charged lipid, a steroid, and a polymer-conjugated lipid. Each possibility represents a separate embodiment of the present invention.

In other embodiments, the compositions of the present invention may be used as a delivery system to administer a therapeutic agent to its target location in the body. Thus, in some embodiments, the present invention relates to a method for administering a therapeutic agent, by preparing a composition comprising a cationic lipid as described herein and a therapeutic agent, and administering the combination to a subject in need thereof.

In particular embodiments, the present invention provide novel cationic lipids that enable the formulation of improved compositions for the in vitro and in vivo delivery of IVT-mRNA and/or other oligonucleotides.

In some embodiments, these lipid nanoparticle compositions are useful for expression of protein encoded by mRNA.

In other embodiments, these improved lipid nanoparticles compositions are useful for upregulation of endogenous protein expression by delivering miRNA inhibitors targeting one specific miRNA or a group of miRNA regulating one target mRNA or several mRNA.

In other embodiments, these improved lipid nanoparticle compositions are useful for down-regulating (e.g., silencing) the protein levels and/or mRNA levels of target genes.

In some other embodiments, the lipid nanoparticles are also useful for delivery of mRNA and plasmids for expression of transgenes.

In yet other embodiments, the lipid nanoparticle compositions are useful for inducing a pharmacological effect resulting from expression of a protein, e.g., increased production of red blood cells through the delivery of a suitable erythropoietin mRNA, or protection against infection through delivery of mRNA encoding for a suitable antibody.

According to some embodiments, the cationic lipid may be in the form of nanoparticles and administered as is. In some embodiments, the nanoparticles may be administered in a solution. In some embodiments, the nanoparticles may be formulated to a suitable pharmaceutical composition to be administered by any desired route of administration. Exemplary routes of administration include such routes as, but not limited to: topical, oral or parenteral. Depending on the intended mode of administration, the compositions used may be in the form of solid, semi-solid or liquid dosage forms, such, as for example, tablets, suppositories, pills, capsules, powders, liquids, suspensions, or the like, preferably in unit dosage forms suitable for single administration of precise dosages. The pharmaceutical compositions may include the cationic particles, a pharmaceutical acceptable excipient, and, optionally, may include other medicinal agents, pharmaceutical agents, carriers, adjuvants, and the like. It is preferred that the pharmaceutically acceptable carrier be one which is inert to the nucleic acid encapsulated within the particles and which has no detrimental side effects or toxicity under the conditions of use. In some embodiments, the administration is localized. In some embodiments, the administration is systemic.

In some embodiments, injectable formulations for parenteral administration can be prepared as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, and the like. Aqueous injection suspensions may also contain substances that increase the viscosity of the suspension, including, for example, sodium carboxymethylcellulose, sorbitol, and/or dextran. Optionally, the suspension may also contain stabilizers. The parenteral formulations can be present in unit dose or multiple dose sealed containers, such as ampules and vials, and can be stored in a freeze-dried (lyophilized) condition requiring only the addition of the sterile liquid carrier, such as, for example, water, for injections immediately prior to use. In some embodiments, parenteral administration includes intravenous administration.

In other embodiments, for oral administration, a pharmaceutically acceptable, non-toxic composition may be formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include solutions, suspensions, tablets, dispersible tablets, pills, capsules, powders, sustained release formulations and the like. Formulations suitable for oral administration can consist of liquid solutions such as effective amounts of the compound(s) dissolved in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, (such as, for example ethanol, benzyl alcohol, and the polyethylene alcohols), either with or without the addition of a pharmaceutically acceptable surfactant, suspending agents, or emulsifying agents.

In determining the dosages of the particles to be administered, the dosage and frequency of administration may be selected in relation to the pharmacological properties of the specific nucleic acids encapsulated within the particles.

In some representative embodiments, a particle comprising a nucleic acid, such as, for example, siRNA, miRNA, shRNA, anti-sense RNA, and the like, may be used in the treatment of various leukocyte-associated conditions, depending on the identity of the nucleic acid, the specific target leukocyte, and the like. In some embodiments, the nucleic acid encapsulated within the particles may be a nucleic acid capable of inducing silencing of a target gene. In some embodiments, the target gene may be any gene, the expression of which is related to the condition to be treated. In some embodiments, the target gene may be a gene selected from, but not limited to: growth factors (such as EGFR, PDGFR), genes related to angiogenesis pathways (such as VEGF, Integrins), genes involved in intracellular signaling pathways and cell cycle regulation (such as PI3K/AKT/mTOR, Ras/Raf/MAPK, PDK1, CHK1, PLK1, Cyclins). In some embodiments, a combination of nucleic acids, each having one or more targets may be encapsulated within the particles.

According to some embodiments, exemplary leukocyte-associated conditions that may be treated by the targeted particles may be selected from, but not limited to: various types of cancer, various infections (such as, for example, viral infection, bacterial infection, fungal infection, and the like), autoimmune diseases, neurodegenerative diseases, inflammations, and the like.

In some representative embodiments, the targeted particles comprising a nucleic acid (such as, siRNA or miRNA, shRNA, anti-sense RNA, or the like), may be used for the treatment of cancer.

In some embodiments, cancer is a disorder in which a population of cells has become, in varying degrees, unresponsive to the control mechanisms that normally govern proliferation and differentiation. In some embodiments, the cancer is a blood cancer. Non-limiting examples of blood cancers are lymphoma, leukemia and myeloma. Lymphomas may be divided into two categories: Hodgkin lymphoma and non-Hodgkin lymphoma. Most non-Hodgkin lymphomas are B-cell lymphomas, that grow quickly (high-grade) or slowly (low-grade). There are 14 types of B-cell non-Hodgkin lymphomas. The others are T-cell lymphomas.

In some representative embodiments, the nucleic acid that may be used for the treatment of cancer is directed against a target gene, which is involved in the regulation of cell cycle. In some representative embodiments, the target gene may be Polo-like Kinase 1 (PLK), Cyclin D1, CHK1, Notch pathway genes.

According to some exemplary embodiments, the plurality of lipids of the lipid particles may be of natural or synthetic source and may be selected from, but not limited to: cationic lipids, phosphatidylethanolamines, ionized lipids, membrane stabilizing lipids, phospholipids, and the like, or combinations thereof. Each possibility represents a separate embodiment of the present invention.

In some embodiments, the membrane stabilizing lipids may be selected from, but not limited to: cholesterol, phospholipids (such as, for example, phosphatidylcholine, phosphatidylethanolamine, phosphatidylinositol, phosphatidylserine, phosphatidylglycerol, diphosphatidylglycerols), cephalins, sphingolipids (sphingomyelins and glycosphingolipids), glycoglycerolipids, and combinations thereof. Each possibility represents a separate embodiment of the present invention.

In some embodiments, the phosphatidylethanolamines may be selected from, but not limited to: 1,2-dilauroyl-L-phosphatidyl-ethanolamine (DLPE), 1,2-Dioleoyl-sn-glycero-3-phosphoethanolamine (DOPE), 1,2-Diphytanoyl-sn-glycero-3-phosphoethanolamine (DPhPE) 1,3-Dipalmitoyl-sn-glycero-2-phosphoethanolamine (1,3-DPPE), 1-Palmitoyl-3-oleoyl-sn-glycero-2-phosphoethanolamine (1,3-POPE), Biotin-Phosphatidylethanolamine, 1,2-Dimyristoyl-sn-glycero-3-phosphoethanolamine (DMPE), Dipalmitoylphosphatidylethanolamine (DPPE), 1,2-Distearoyl-sn-glycero-3-phosphoethanolamine (DSPE) or combinations thereof. In some embodiments, the Phosphatidylethanolamines may be conjugated to a PEG-Amine derivative. Each possibility represents a separate embodiment of the present invention.

According to some embodiments, "neutral lipid" refers to any of a number of lipid species that exist either in an uncharged or neutral zwitterionic form at physiological pH, such lipids include, but are not limited to, phosphotidylcholines such as 1,2-Distearoyl-sn-glycero-3-phosphocholine (DSPC), 1,2-Dipalmitoyl-sn-glyccro-3-phosphocholine (DPPC), 1,2-Dimyristoyl-sn-glyccro-3-phosphocholine (DMPC), 1-Palmitoyl-2-olcoyl-sn-glyccro-3-phosphocholine (POPC), 1,2-dioleoyl-sn-glyccero-3-phosphocholine (DOPC), phophatidyl ethanolamines such as 1,2-Diolcoyl-sn-glyccro-3-phosphoethanolamine (DOPE), sphingomyelins (SM), ceramides, steroids such as sterols and their derivatives. Neutral lipids may be synthetic or naturally derived.

According to some embodiments, the particles (lipid phase thereof), may further include one or more PEG derivatives. In some embodiments, the PEG derivatives may be conjugated to one or more additional molecules, such as, a lipid. In some embodiments, the PEG derivative is selected from, but not limited to: PEG-DMG 3-N-(-methoxy poly(ethylene glycol)2000)carbamoyl-1,2-dimyrisyl glycerol, PEG-cDMA 3-N-(-methoxy poly(ethylene glycol)2000)carbamoyl-1,2-dimyristyloxy-propylamine; PEG-cDSA, 3-N-(-methoxy poly(ethylene glycol)2000)carbamoyl-1,2-distearyloxy-propylamine, DSPE-PEG, PEG-maleimide, DSPE-PEG-maleimide, or combinations thereof. Each possibility represents a separate embodiment of the present invention.

In some embodiments, the maleimide derivative/moiety may be conjugated, attached or linked to a PEG-derivative, which may be by itself conjugated, linked and/or attached to a lipid.

According to some embodiments, the ratio between the various lipids in the particle may vary. In some embodiments, the ratio is a molar ratio. In some embodiments, the ratio is a weight ratio. In some embodiments, each of the lipid groups may be at molar ratio/a weight ratio of about 1%-99%.

According to some embodiments, the weight ratio between the nucleic acid and the lipid mixture may be adjusted so as to achieve maximal biological effect by the nucleic acid on the target site. In some embodiments, the ratio between the nucleic acid and the lipid phase may be 1:1. For example, the weight ratio between the nucleic acid and the lipid phase may be 1:2. For example, the weight ratio between the nucleic acid and the lipid phase may be 1:5. For example, the weight ratio between the nucleic acid and the lipid phase may be 1:10. For example, the weight ratio between the nucleic acid and the lipids phase may be 1:16. For example, the weight ratio between the nucleic acid and the lipid phase may be 1:20. In some embodiments, the weight ratio between the nucleic acid and the lipid phase is about 1:1 to 1:20 (w:w).

In some embodiments, the particles are nanoparticles. In some embodiments, the particles (including the nucleic acid encapsulated within) and the targeting moiety on the surface particles have a particle size (diameter) in the range of about 10 to about 500 nm. In some embodiments, the particles have a particle size (diameter) in the range of about 10 to about 350 nm. In some embodiments, the particles have a particle size (diameter) in the range of about 50 to about 250 nm. In some embodiments, the particles have a particle size (diameter) in the range of about 10 to about 200 nm. In some embodiments, the particles have a particle size (diameter) in the range of about 20 to about 200 nm. In some embodiments, the particles have a particle size (diameter) in the range of about 50 to about 200 nm. In some embodiments, the particles have a particle size (diameter) in the range of about 75 to about 200 nm. In some embodiments, the particles have a particle size (diameter) in the range of about 90 to about 200 nm. In some embodiments, the particles have a particle size (diameter) in the range of about 100 to about 200 nm. In some embodiments, the particles have a particle size (diameter) in the range of about 120 to about 200 nm. In some embodiments, the particles have a particle size (diameter) in the range of about 150 to about 200 nm. In some embodiments, the particles have a particle size (diameter) in the range of about 50 to about 150 nm. In some embodiments, the particles have a particle size (diameter) in the range of over about 10 nm. In some embodiments, the particles have a particle size (diameter) of over about 20 nm. In some embodiments, the particles have a particle size (diameter) of over about 30 nm. In some embodiments, the particles have a particle size (diameter) of over about 40 nm. In some embodiments, the particles have a particle size (diameter) of over about 50 nm. In some embodiments, the particles have a particle size (diameter) of over about 60 nm. In some embodiments, the particles have a particle size (diameter) of over about 70 nm. In some embodiments, the particles have a particle size (diameter) of over about 80 nm. In some embodiments, the particles have a particle size (diameter) of over about 90 nm. In some embodiments, the particles have a particle size (diameter) of over about 100 nm. In some embodiments, the particles have a particle size (diameter) of over about 200 nm. In some embodiments, the particles have a particle size (diameter) of not more than about 500 nm. In some embodiments, the particles (including the nucleic acid encapsulated within) have a particle size (diameter) in the range of about 5 to about 200 nm. In some embodiments, the particles (including the nucleic acid encapsulated within) have a particle size (diameter) in the range of about 50 to about 60 nm. In some embodiments, the particles (including the nucleic acid encapsulated within) have a particle size (diameter) in the range of about 55 to about 58 nm. In some embodiments, the size is a hydrodynamic diameter.

According to exemplary embodiments, the particles may be comprised of a cationic lipid (such as compound shown in Table 1 or 2), cholesterol, 1,2-Distearoyl-sn-glycero-3-phosphocholine (DSPC), PEG derivative (such as DMG-PEG) and PEG-maleimide conjugated to a lipid (such as DSPE-PEG-maleimide); at various mol:mol ratios, and further conjugated to a targeting moiety, wherein the targeting moiety is conjugated, linked, attached to the maleimide moiety. For example, the lipid phase may be comprised of: cationic lipid (DLinMC3)/DSPC/cholesterol/DMG-PEG/DSPE-PEG-Maleimide (mol/mol 50:10:38:1.5:0.5). For example, the lipid phase may be comprised of: DLinMC3-DMA/Chol/DSPC/DMG-PEG/DSPE-PEG-maleimide (mol/mol 50:38:10:1.95:0.05).

According to some embodiments, the lipid phase may comprise about 30-60% (mol) cationic lipids. For example, the cationic lipid(s) may comprise about 40-50% (mol) of the lipid phase.

According to some embodiments, the lipid phase may comprise about 20-70% (mol) membrane stabilizing lipids. For example, the membrane stabilizing lipids may comprise about 40-60% of the lipid phase. In some embodiments, more than one type of membrane stabilizing lipid may be used in the lipid phase. For example, the membrane stabilizing lipid may include cholesterol (being about 30-50% (mol) of the lipid phase), and a phospholipid (such as, for example, DSPC), that may be about 5-15% (mol) of the lipid phase.

According to some embodiments, the lipid phase may comprise about 0.01-3% (mol:mol) of PEG-maleimide (optionally conjugated to a lipid). For example, the PEG-maleimide may comprise about 0.05-0.6% of the lipid mixture.

According to some embodiments, an additional PEG-derivative (conjugated to a lipid) may comprise about 0.5-10% of the lipid phase composition.

According to some exemplary embodiments, there is provided a method for the preparation of targeted particles for delivery of a nucleic acid to leukocytes, the method comprising one or more of the steps of:
 a) mixing a plurality of lipids, including, a cationic lipid according to the invention, membrane stabilizing lipid and PEG-maleimide conjugated to a phospholipid, in an organic solvent at a desired ratio;
 b) adding nucleic acids to the mixture in a suitable solution at a desired ratio;
 c) mixing the lipid mixture and the nucleic acids in a microfluidic micromixer to form particles;
 d) dialyzing the particles to remove undesired solvents;
 e) incubating the particles with reduced targeting antibodies to generate targeted particles;
 f) removing unconjugated antibodies, optionally by gel filtration;
 g) filtration of reconstituted t-conjugated particles encapsulating nucleic acid molecules;

In some embodiments, the lipids are suspended in an acidic aqueous buffer, such as, ethanol. In some embodiments, the nucleic acid is in an acetate buffer solution.

In some embodiments, the nucleic acid may be mixed with the lipid mixture in a microfluidizer mixer to form particles encapsulating/carrying the nucleic acid.

Definitions

To facilitate an understanding of the present invention, a number of terms and phrases are defined below. It is to be understood that these terms and phrases are for the purpose of description and not of limitation, such that the terminology or phraseology of the present specification is to be interpreted by the skilled artisan in light of the teachings and guidance presented herein, in combination with the knowledge of one of ordinary skill in the art.

As referred to herein, the terms "nucleic acid", "nucleic acid molecules" "oligonucleotide", "polynucleotide", and "nucleotide" may interchangeably be used herein. The terms are directed to polymers of deoxy ribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, Antisense RNA, and the like. Each possibility represents a separate embodiment of the present invention. The terms further include oligonucleotides composed of naturally occurring bases, sugars, and covalent inter nucleoside linkages, as well as oligonucleotides having non-naturally occurring portions, which function similarly to respective naturally occurring portions.

The terms "polypeptide," "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "construct", as used herein, refers to an artificially assembled or isolated nucleic acid molecule which may include one or more nucleic acid sequences, wherein the nucleic acid sequences may include coding sequences (that is, sequence which encodes an end product), regulatory sequences, non-coding sequences, or any combination thereof. The term construct includes, for example, vector but should not be seen as being limited thereto.

"Expression vector" refers to constructs that have the ability to incorporate and express heterologous nucleic acid fragments (such as, for example, DNA), in a foreign cell. In other words, an expression vector comprises nucleic acid sequences/fragments (such as DNA, mRNA, tRNA, rRNA), capable of being transcribed. Many prokaryotic and eukaryotic expression vectors are known and/or commercially available. Selection of appropriate expression vectors is within the knowledge of those having skill in the art. In some representative embodiments, the expression vector may encode for a double stranded RNA molecule in the target site.

The term "expression", as used herein, refers to the production of a desired end-product molecule in a target cell. The end-product molecule may include, for example an RNA molecule; a peptide or a protein; and the like; or combinations thereof.

As used herein, the terms "introducing" and "transfection" may interchangeably be used and refer to the transfer of molecules, such as, for example, nucleic acids, polynucleotide molecules, vectors, and the like into a target cell(s), and more specifically into the interior of a membrane-enclosed space of a target cell(s). The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. The transfection of the cell may be performed on any type of cell, of any origin, such as, for example, human cells, animal cells, plant cells, virus cell, and the like. The cells may be selected from isolated cells, tissue cultured cells, cell lines, cells present within an organism body, and the like.

The term "treating" and "treatment" as used herein refers to abrogating, inhibiting, slowing or reversing the progression of a disease or condition, ameliorating clinical symptoms of a disease or condition or preventing the appearance of clinical symptoms of a disease or condition. The term "preventing" is defined herein as barring a subject from acquiring a disorder or disease or condition.

The term "treatment of cancer" is directed to include one or more of the following: a decrease in the rate of growth of the cancer (i.e. the cancer still grows but at a slower rate); cessation of growth of the cancerous growth, i.e., stasis of the tumor growth, and, the tumor diminishes or is reduced in size. The term also includes reduction in the number of metastases, reduction in the number of new metastases formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like. In some embodiments, the cancer is a blood cancer.

The term "Leukocytes" is directed to white blood cells (WBCs), produced and derived from a multipotent, hematopoietic stem cell in the bone marrow. The white blood cells have nuclei, and types of white blood cells can be classified in into five main types, including, neutrophils, eosinophils, basophils, lymphocytes, and monocytes, based on functional or physical characteristics. The main types may be classified into subtypes. For example, lymphocytes include B cells, T cells, and NK cells. B-cells, for example, release antibodies and assist activation of T cells. T cells, for example, can be classified to several subtypes, including: T-helper cells (CD4+ Th) which activate and regulate T and B cells; cytotoxic T cells (CD8+) that can target and kill virus-infected cells and tumor cells; Gamma-delta T cells (γδ T cells) which can bridge between innate and adaptive immune responses and be involved in phagocytosis; and Regulatory (suppressor) T cells which modulate the immune system, maintain tolerance to self-antigens, and abrogate autoimmune conditions.

Synthetic Methods

The compounds of the present invention can be prepared in accordance the following general synthetic methods:

$z = 0, 2$
$z_1 = 2\text{-}10$
$n = 0\text{-}6$
R = alkyl, alkenyl, alkynyl
R', R" = alkyl
NR'R" = heterocyclic ring, guanidine
X = leaving group

SCHEME 2-continued

| General Scheme | Method |
|---|---|
| (chemical structures) | A&B |
| (chemical structures) | A&D |
| (chemical structures) | |

$z = 0, 2$
$z_1, x = 2\text{-}10$
$n = 0,6$
R = alkyl, alkenyl, alkynyl
R', R" = alkyl
P = amine protecting group
LG = leaving group

SCHEME 3

| General Scheme | Method |
|---|---|
| (chemical structures) | B |
| (chemical structures) | B |

SCHEME 3-continued

| General Scheme | Method |
|---|---|

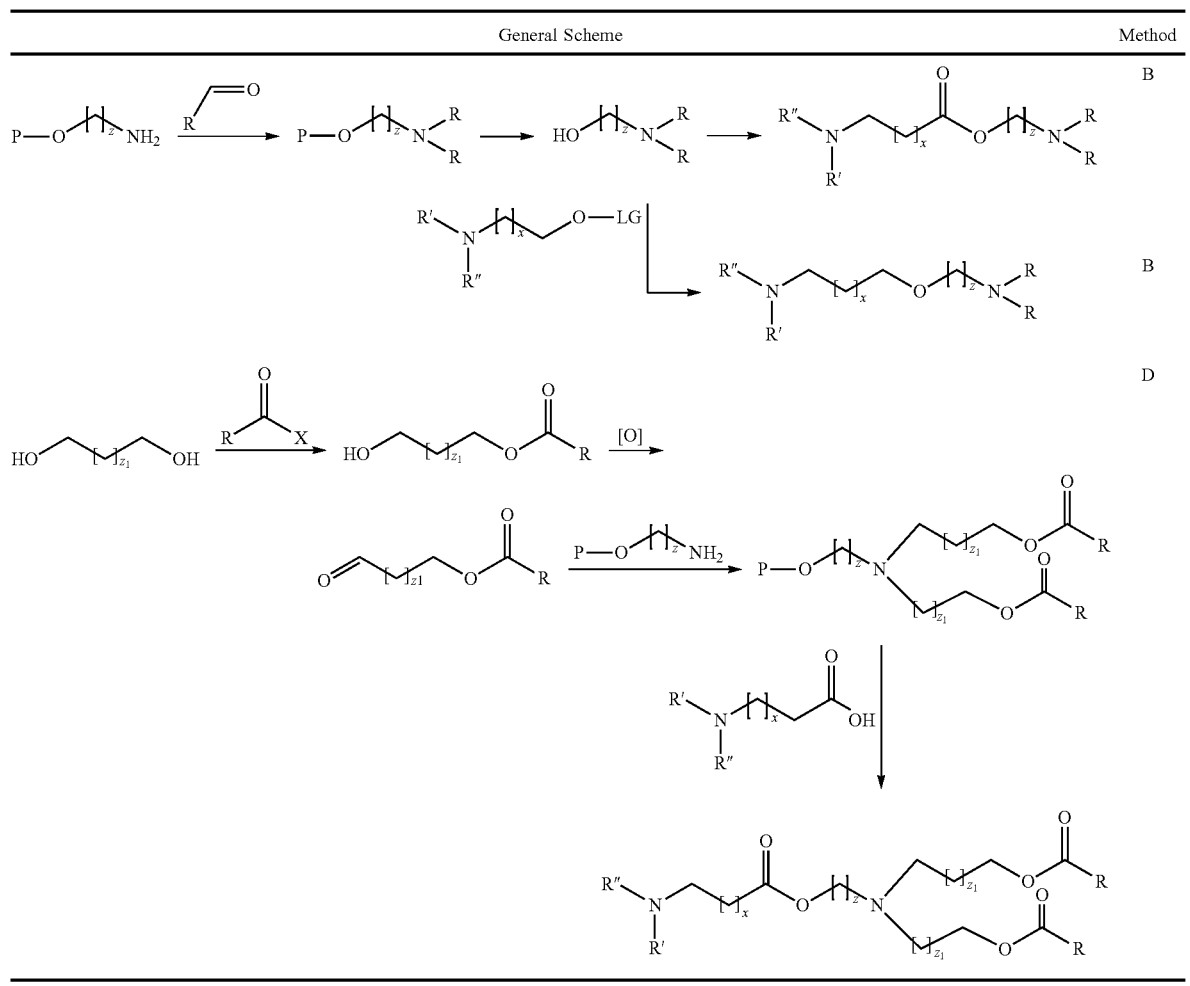

z = 0, 2
x, $z_1$ = 2-10
R = alkyl, alkenyl, alkynyl
P = protecting group
LG = leaving group The foregoing examples of the related art and limitations related therewith are intended to be illustrative and not exclusive. Other limitations of the related art will become apparent to those of skill in the art upon a reading of the specification and a study of the figures.

All references cited herein are hereby incorporated by references in their entirety herein.

Example 1: Materials and Methods

Materials

Lipids: All lipids used for LNPs production (Cholesterol, DSPC and DSPE PEG-Mal) were purchased from Avanti Polar lipids (USA).

Monoclonal antibodies: anti-CD45 AF647, Annexin-647 was purchased from BioLegend. Propodeum Iodide was purchased from Sigma-Aldrich.

siRNA molecules were designed and screened by Alnylam Pharmaceuticals (USA).

Chemically Modified siRNAs Sequences:

```
CD45 siRNA:
                                         (SEQ ID NO: 1)
   Sense strand:      cuGGcuGAAuuucAGAGcAdTsdT (SEQ ID NO: 2)
   Anti-Sense strand: UGCUCUGAAAUUcAGCcAGdTsdT NC5 siRNA (siNC5 or ctl siRNA):
                                         (SEQ ID NO: 5)
   Sense strand:      CAUAUUGCGCGUAUAGUCGCGUUAG (SEQ ID NO: 6)
   Anti-Sense strand: UGGUAUAACGCGCAUAUCAGCGCAAUC Luc siRNA (siLuc):
                                         (SEQ ID NO: 3)
   Sense strand:      cuuAcGcuGAGuAcuucGAdTsdT (SEQ ID NO: 4)
   Anti-Sense strand: UCGAAGuACUcAGCGuAAGdTsdT
```

Alexa-647-labeled siRNA possessed the same sequence as siLuc. 2'-OMe modified nucleotides are in lower case, and phosphorothioate linkages are represented by "s".

```
PLK 1 siRNA (PLK 1)
                                           (SEQ ID NO: 7)
Sense strand         GCUUAAUGACGAGUUCUUUACUUCT (SEQ ID NO: 8)
Anti-Sense strand:   GACGAAUUACUGCUCAAGAAAUGAAGA
```

Cell Lines:

SupT1, HEK 293, NAR and OVCAR-8 cells were purchased from the American Type Culture Collection (ATCC) and cultured as recommended.

Preparation of Lipid-Based Nanoparticles (LNPs) Entrapping siRNAs

LNPs were prepared by using microfluidic micro mixture (Precision NanoSystems, Vancouver, BC, Canada) as described by Cohen et. al. One volume of lipid mixtures (cationic lipid, DSPC, Chol, DMG-PEG and DSPE-PEG Mal at 50:10:38:1.5:0.5 mole ratio, 9.64 nM total lipid concentration) in ethanol and three volumes of siRNA (1:16 w/w siRNA to lipid) containing acetate buffer solutions were injected through the micro mixer at a combined flow rate of 2 mL/minute (0.5 mL/min for ethanol and 1.5 mL/min for aqueous buffer). For labeled LNPs, 10% of Alexa-647 labeled siRNA were incorporated. For Cy5 labeled particles, 10% Cy5 labeled non-targeted siRNA was used. The resultant mixture was dialyzed against PBS (pH 7.4) for 16 h to remove ethanol.

Size, ζ-Potential and Ultrastructure Analysis of a CD38-LNPs-siRNA

LNPs size distribution and ζ potential were determined by dynamic light scattering using a Malvern nano ZS ζ-sizer (Malvern instruments, UK). For size measurements, LNPs were diluted 1:20 in PBS. All utilized samples showed a polydispersity index (PDI) lower than 0.2. For ζ potential measurements, LNPs were diluted 1:200 in DDW. In some cases, as indicated, size and zeta potential measurements were performed in water.

Quantitative Real-Time PCR

The mRNA levels of pololike kinase 1 (PLK1 gene) in cells was quantified by real-time PCR, forty eight or Seventy-two hours post-transfection. Total RNA was isolated using the E-Z RNA purification kit (Biological industries, Beit Haemek, Israel), and 1 μg of RNA from each sample was reverse transcribed into cDNA using the High Capacity cDNA Reverse Transcription Kit (Applied Biosystems, Foster City, CA), Quantification of cDNA (5 ng total) was performed on the step one Sequence Detection System (Applied Biosystems, Foster City, CA) using syber green (Applied Biosystems). GAPDH was chosen as a housekeeping gene.

For real time PCR the following primers were chosen:

```
Primers for PLK1:
                                           (SEQ ID NO: 9)
    forward - ACCAGCACGTCGTAGGATTC (SEQ ID NO: 10)
    reverse - CAAGCACAATTTGCCGTAGG Primers for GAPDH:
                                           (SEQ ID NO: 11)
    forward - TCA GGG TTT CAC ATT TGG CA (SEQ ID NO: 12)
    reverse - GAG CAT GGA TCG GAA AAC CA
```

In Vitro Gene Silencing

Supt1 or NAR or OVCAR cells were placed in tissue culture 12-wells plates at a density of $1 \times 10^5$ cells with 1 mL of full medium. LNPs containing different siRNAs (siPLK1 or siCD45 or siLUC) were added to the wells and the concentration was mentioned in figures. Cells were isolated at different time intervals mentioned in the figures and analyzed by either flow cytometry (for siCD45 knockdown), or qPCR for analysis of PLK1 silencing. Apoptosis assay using PI/Annexin was analyzed by flow cytometry in case of siPLK1 induced cell death.

Cell Cycle Studies:

The transfected cells were washed with ice-cold PBS, and fixed with 70% ethanol for 1 h. Then, the cells were washed twice with cold PBS and incubated for 10 min at 37° C. in 250 μL PBS with 10 μg/mL propidium iodide (PI), 2.5 μg/mL DNase-free RNase A (Sigma, USA) and 0.01% Triton-X. PI fluorescence was assessed by flow cytometry. Analyzes by FlowJo™ were performed on at least 9000 cells per samples after gating out debris and cell duplets based on the FL2-Area/FL2-Width channels. Cell cycle distributions were obtained via the application of the Dean-Jett-Fox model on gated cells with RMS scores ranging between 1.5 and 2.5.

Example 2: Synthesis of Lipids

General Preparation Methods (Exemplary Embodiments of Schemes 1-3).

SCHEME 4

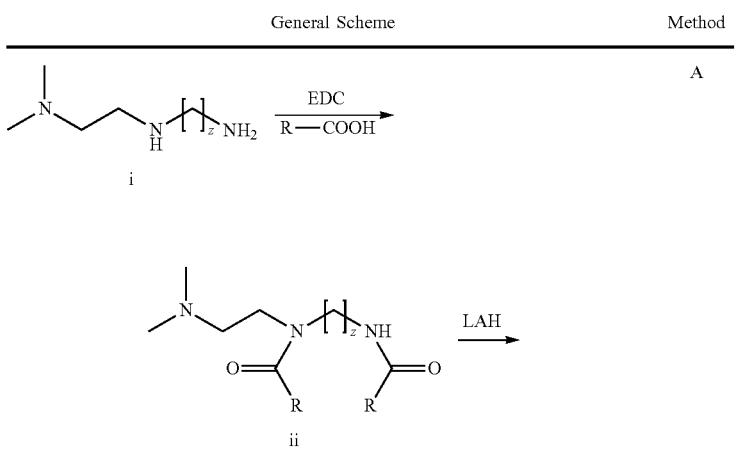

SCHEME 4-continued
| General Scheme | Method |
|---|---|
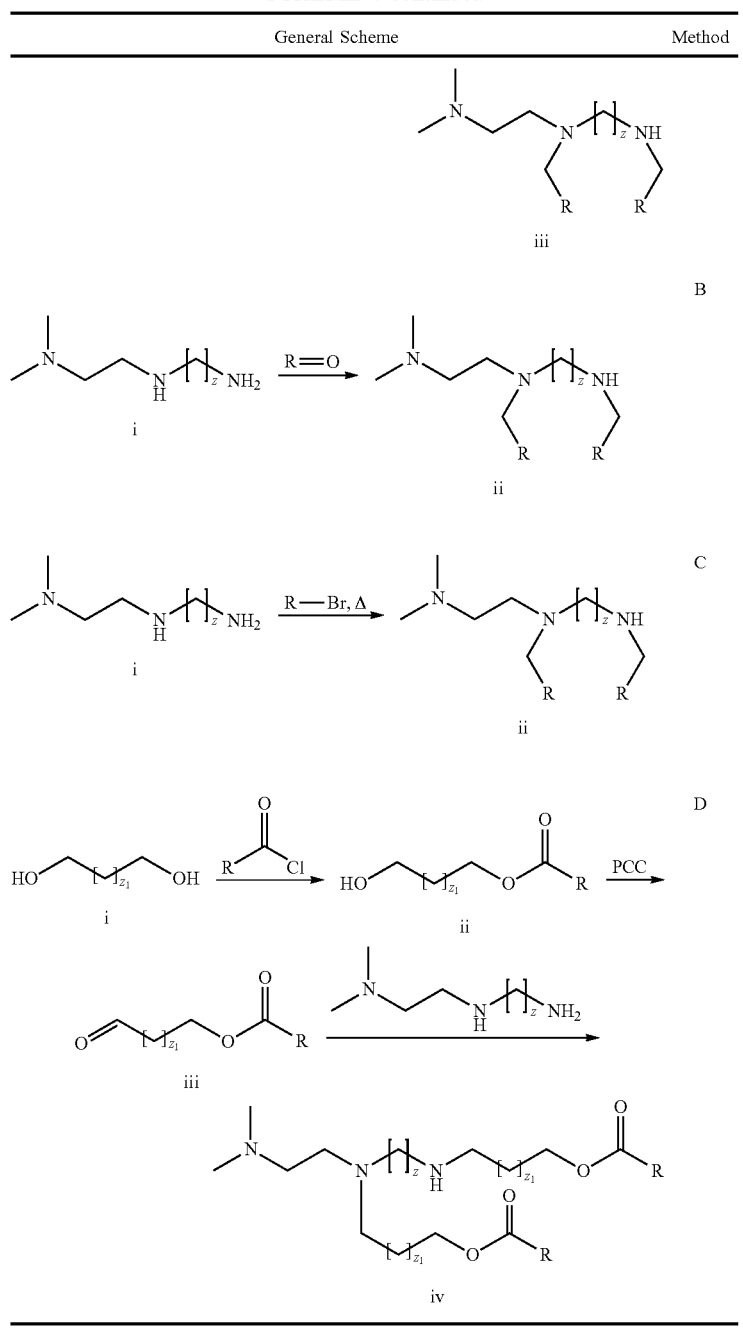
z = 0, 2
$z_1$ = 2-10
R = alkyl, alkenyl, alkynyl
SCHEME 5
| General Scheme | Method |
|---|---|
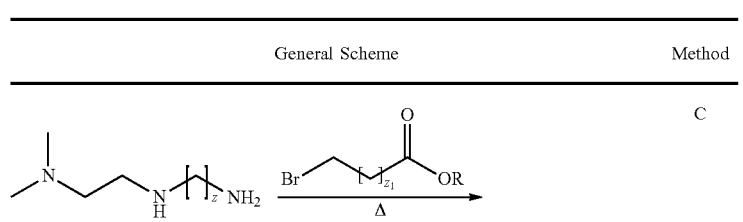

SCHEME 5-continued
| General Scheme | Method |
|---|---|
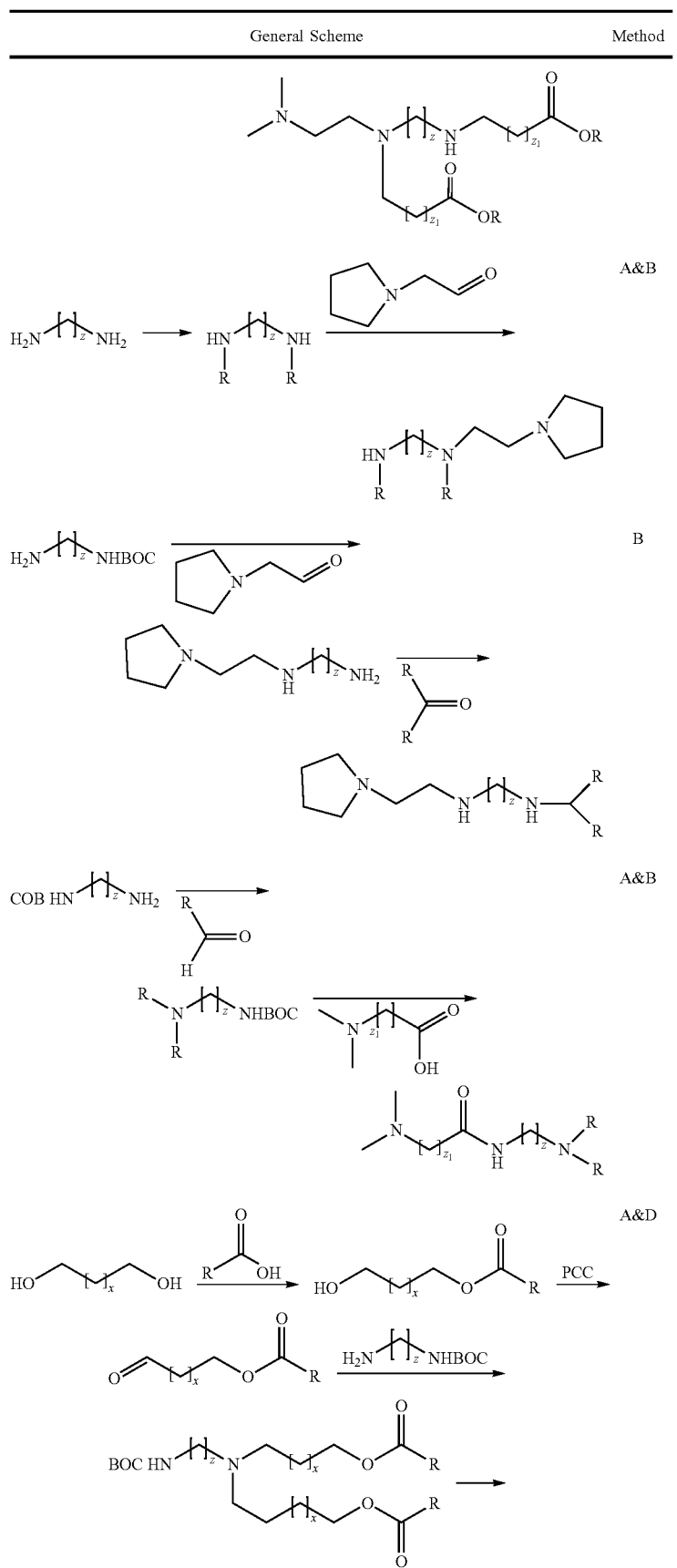

SCHEME 5-continued
| General Scheme | Method |
|---|---|
| 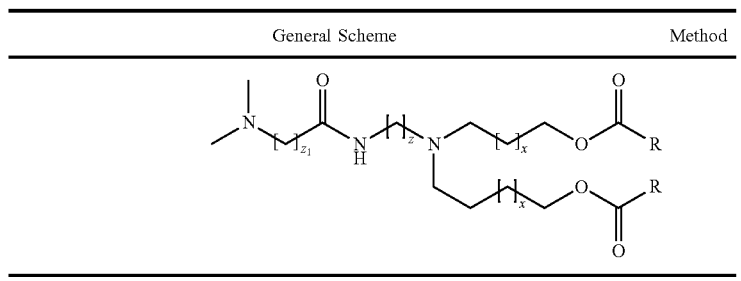 | |
z = 0,2
$z_1$, x = 2-10
R = alkyl, alkenyl, alkynyl
SCHEME 6
| General Scheme | Method |
|---|---|
| 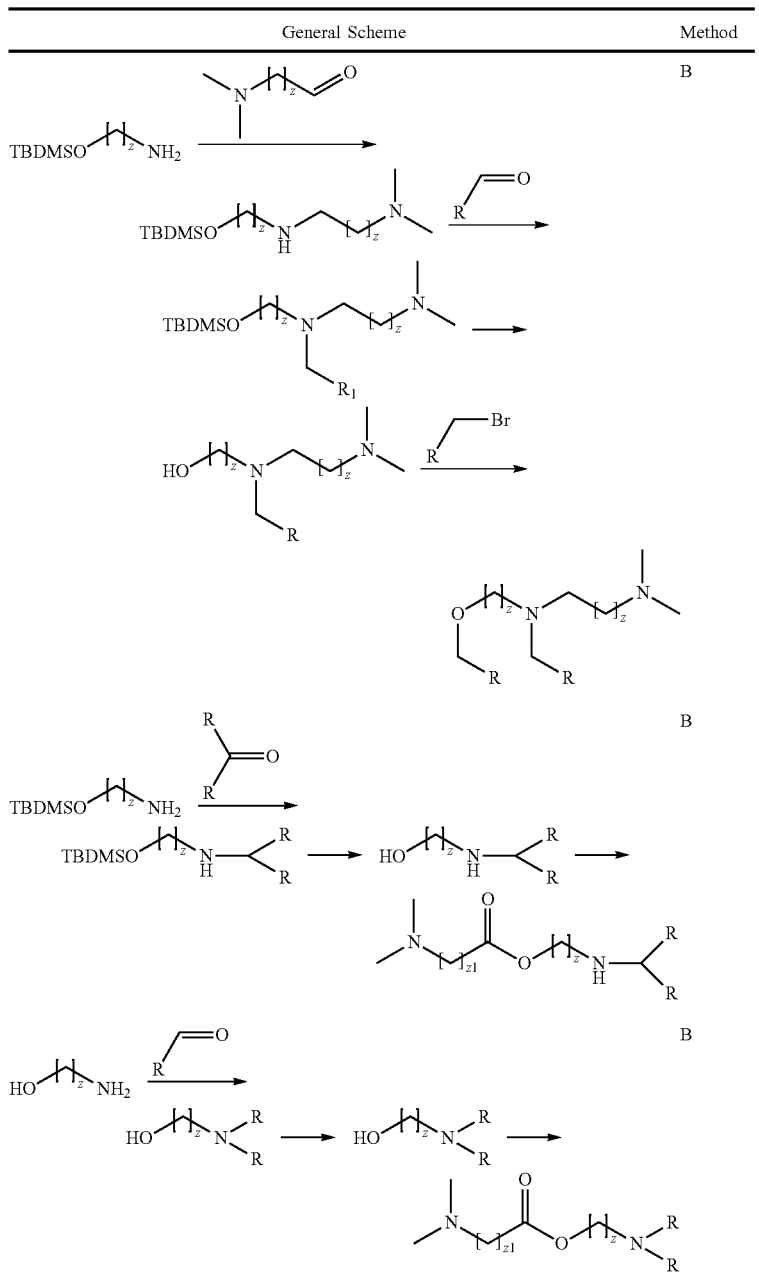 | B<br><br>B<br><br>B |

SCHEME 6-continued

| General Scheme | Method |
|---|---|
| 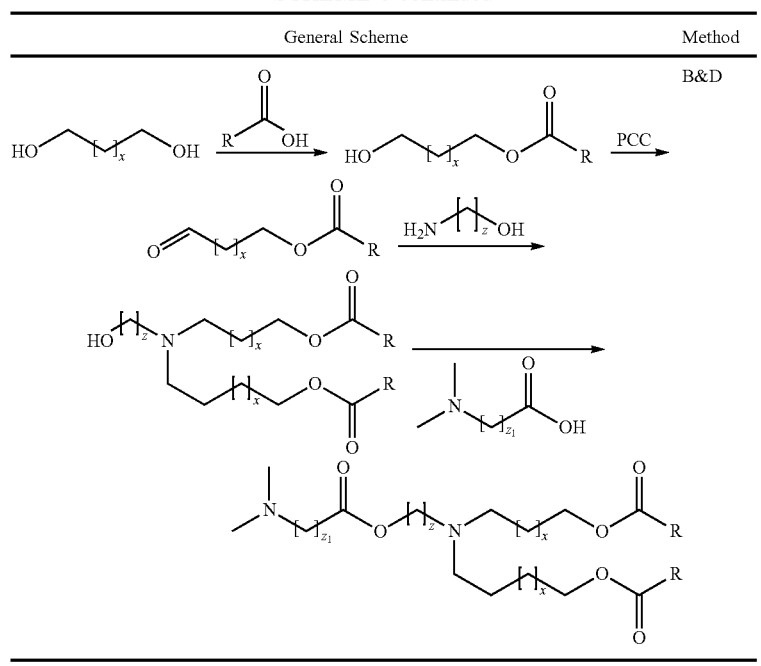 | B&D | z = 0, 2
zl, x = 2-10
R, R[2,] R[3] = alkyl, alkenyl, alkynyl

Method A:

Compound (i) or the amine functional compound as defined above is conjugated to fatty acids via standard EDC/NHC coupling method yielded the compound (ii). Further reduction with Lithium aluminum hydride (LAH) followed by silica gel column chromatography purification give desired final compound (iii).

Method B:

Compound (i) and/or the amine functional compound and alkyl/alkenyl fatty chain corresponding aldehyde stirred for 2 hr at RT under argon, followed by reduction with NaCNBH$_4$ or Sodium triacetoxy borohydride and silica gel column chromatography purification yields desired final compound.

Method C:

Compound (i) or the amine functional compound as defined above, is heated with corresponding alkyl/alkenyl bromide (any other as defined above) for overnight followed by column chromatography purification yields desired final compound (ii).

Method D:

Di-hydroxyl compound reacted with fatty acid chloride in presence of tri ethyl amine give the compound (ii). The compound (ii) is further oxidized with pyridinium chlorochromate (PCC) followed by reacted with amine functional compound and silica gel column chromatography purification yields desired compound (iv).

Synthesis of Lipid 1 (Method A)

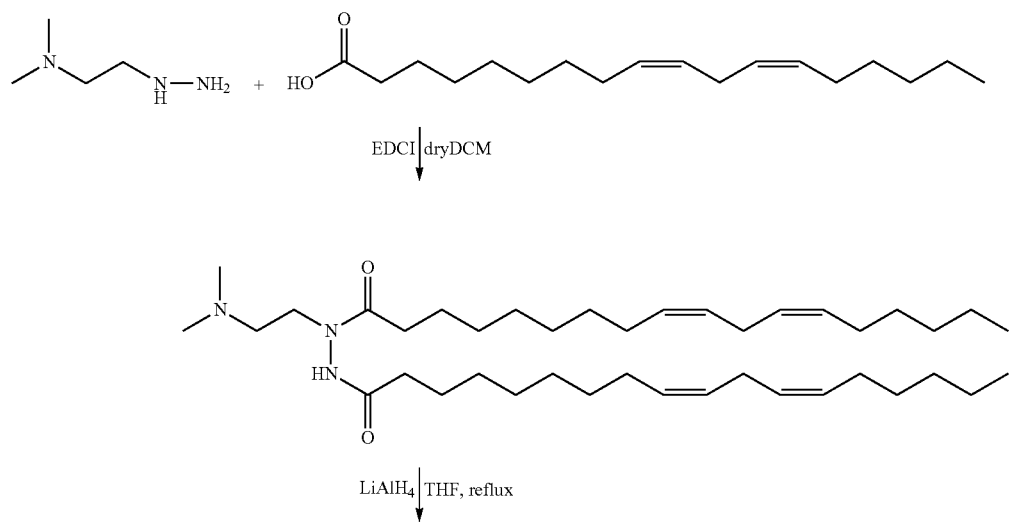

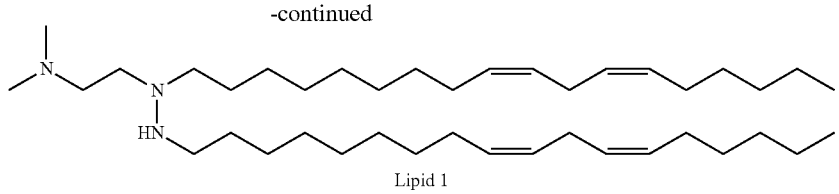

Lipid 1

Linoleic acid (0.88 mg, 3.14 mmol) and EDCI (0.9 mg, 4.71 mmol) were taken in a 100 mL flask and dissolved in dry DCM followed by addition of dimethylaminoethyl hydrazine hydrochloride (0.2 mg, 1.25 mmol) and tri ethylamine (0.1 ml). The reaction mixture was stirred for 24 hr, washed with water and brine solution. The crude compound was purified by silica gel column chromatography (MeOH:CHCl$_3$ (4:96)) to yield 0.8 g of pure compound (9Z,12Z)—N'-(2-(dimethylamino)ethyl)-N'-((9Z,12Z)-octadeca-9,12-dienoyl)octadeca-9,12-dienehydrazide.

$^1$H NMR (400 MHz, CDCl$_3$): δ 5.22-5.45 (8H, m); 3.7-3.8 (1H, t); 3.2-3.3 (1H, m); 2.8 (4H, t), 2.6 (2H, t), 2.3 (6H, s); 2.2 (4H, m); 2.0 (8H, q); 1.2-1.4 (32H, m), 0.9 (6H, t).

ESI-MS: 628.6 (M+1)

The above compound (0.8 mg, 1.27 mmol) was taken in a 50 mL round bottomed (RB) flask and dissolved in 5 mL of dry THF, followed by addition of 1N LAH in THF solution (6 mL, 6.36 mmol) and the reaction mixture was refluxed for 24 hr. The reaction was quenched with saturated ammonium chloride at 0° C. followed by silica gel column chromatography (MeOH:CHCl$_3$ (2:98)) purification to yield 0.3 g of pure compound 2-(1,2-di((9Z,12Z)-octadeca-9,12-dien-1-yl)hydrazinyl)-N,N-dimethylethan-1-amine as pale yellow liquid.

$^1$H NMR (400 MHz, CDCl$_3$): δ NMR: 5.22-5.45 (8H, m); 3.2 (2H, t); 3.1 (2H, t); 2.8 (4H, t), 2.5 (2H, m); 2.4 (6H, s); 2.3 (1H, m); 2.0 (12H, q); 1.5 (4H, m); 1.2-1.4 (32H, m), 0.9 (6H, t).

ESI-MS: 600.6 (M+1)

Synthesis of Lipids 10 & 12

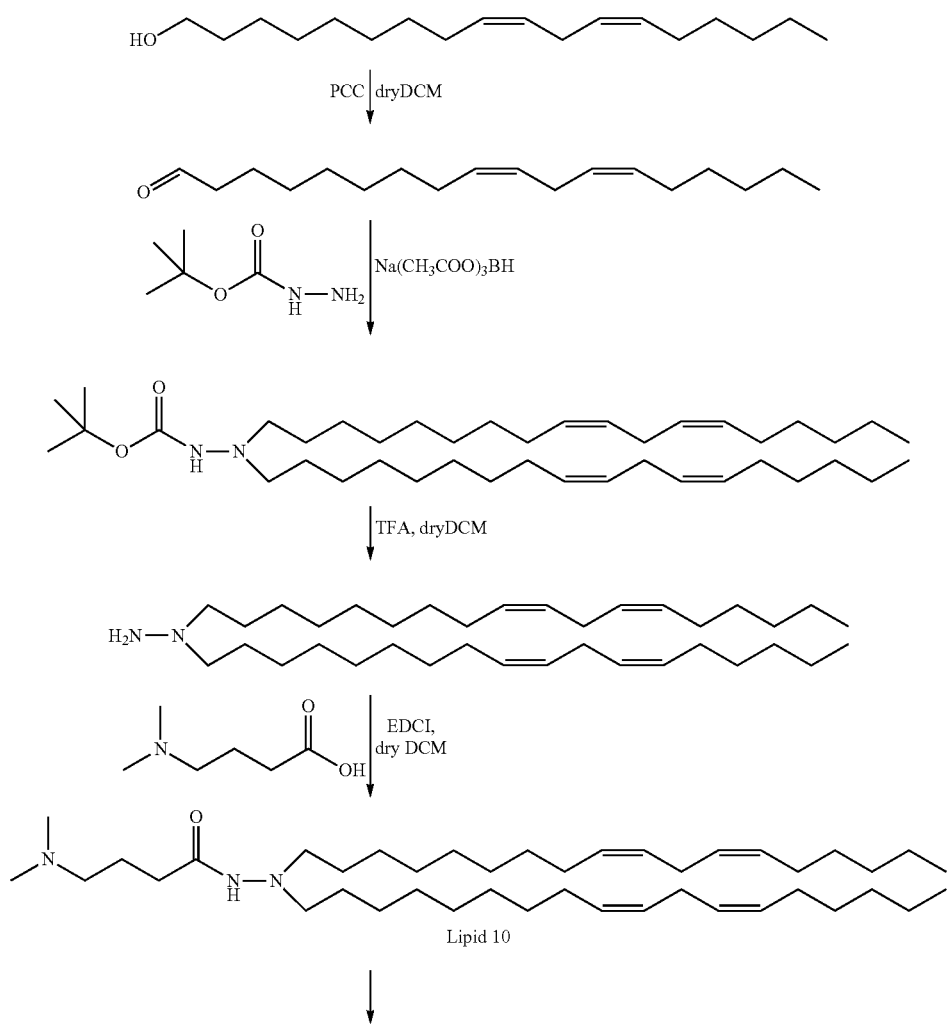

Lipid 10

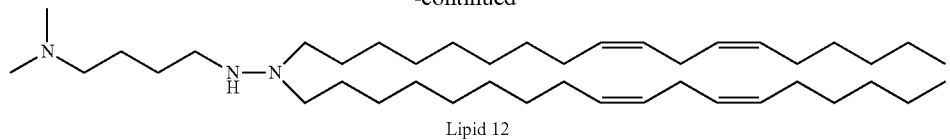

Lipid 12

Linoleic alcohol (1.7 g, 6.3 mmol) was dissolved in dry DCM under argon and molecular sieves were added to the reaction mixture. PCC (2 g, 9.5 mmol) was added by fractions to the reaction mixture over a period of 10 min. The reaction mixture was stirred for 1 hr and filtered through silica pad to remove PCC followed by evaporating the solvent to yield 1.5 g of crude linoleic aldehyde. The crude aldehyde (1.5 g, 5.6 mmol) and Boc-hydrazide (0.6 g, 4.5 mmol) were dissolved in dry DCM under argon atmosphere then Sodium triacetoxy borohydride (4.7 g, 22.6 mmol) was added to the reaction mixture and stirred for 24 hr at room temperature. The reaction was quenched with sodium hydroxide solution and extract with DCM (3×50 mL) followed by washing with water and brine solution. The solvent was evaporated and the residue was purified by silica column chromatography (EtOAc:Hexane (5:95) yielded 1.3 g of pure compound N, N-dilinoleyl-boc hydrazide.

$^1$H NMR (400 MHz, CDCl$_3$): δ 5.22-5.45 (8H, m); 2.8 (4H, t), 2.6 (3H, bs), 2.0-2.1 (8H, q); 1.5-1.8 (6H, m); 1.4-1.5 (12H, s), 1.2-1.4 (32H, m), 0.9 (6H, t)

ESI-MS: 629.6 (M+1)$^+$

N, N-dilinoleyl-boc hydrazide (1.3 g, 2.07 mmol) was dissolved in dry DCM under argon atmosphere. The reaction mixture was cooled to 0° C. and trifluoroacetic acid (TFA) (2 mL) was added drop wise and stirred for 3 hr. Upon completion of reaction by TLC analysis, the reaction mixture was washed with sodium bicarbonate followed by brine solution. The solvent was evaporated and the crude reaction mixture (0.4 g, 0.76 mmol), N, N-dimethyl aminobutyric acid (0.19 g, 1.3 mmol) and EDCI (0.43 g, 2.26 mmol) were dissolved in dry DCM under argon atmosphere. Triethylamine was added and the reaction stirred for 24 hr. The reaction mixture was washed with water followed by sodium bicarbonate and brine solution. The solvent was evaporated and the residue was purified by silica gel column chromatography (MeOH:CHCl$_3$ (2:98) to yield 0.3 g of pure lipid 10 as colorless liquid.

$^1$H NMR (400 MHz, CDCl$_3$): δ 5.22-5.45 (8H, m); 2.8 (4H, t), 2.6 (3H, m), 2.3-2.5 (4H, m); 2.2 (6H, s); 2.0 (8H, q); 1.6-1.8 (8H, m); 1.2-1.5 (36H, m), 0.9 (6H, t)

ESI-MS: 642.6 (M+1)$^+$

The compound 2 was dissolved in dry THF and 1M LAH in THF solution was added to the reaction mixture and refluxed for 12 h. The reaction was quenched with ammonium chloride solution followed by solvent evaporation and silica gel column chromatography purification yielded pure lipid 12.

$^1$H NMR (400 MHz, CDCl$_3$): δ NMR: 5.22-5.45 (8H, m); 2.8 (4H, t), 2.6 (2H, m), 2.4-2.5 (6H, m); 2.2 (6H, s); 2.0 (8H, q); 1.6-1.8 (8H, m); 1.2-1.5 (36H, m), 0.9 (6H, t)

ESI-MS: 629.1 (M+1)$^+$

Synthesis of Lipid 11

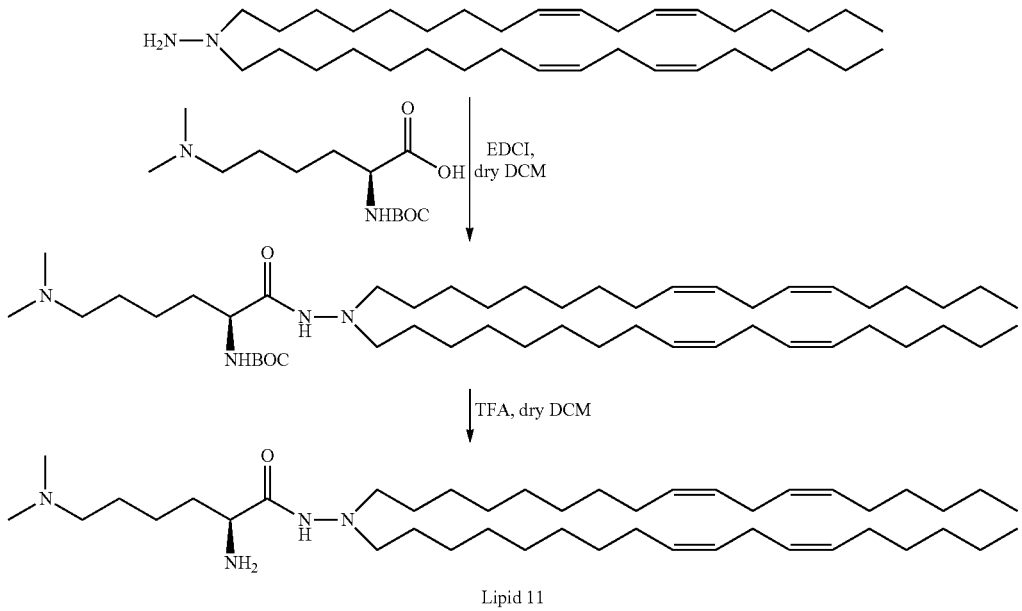

Lipid 11

N,N-dilinoleyl hydrazine (300 mg, 0.56 mmol), N$_\varepsilon$,N$_\varepsilon$ dimethyl-N$_\alpha$ boc L-lysine (180 mg, 1.13 mmol) and EDCI (320 mg, 1.68 mmol) were taken in 50 mL RB flask and dissolved in 10 mL dry DCM under argon. The reaction mixture was stirred for 24 h, and then the reaction mixture was washed with water followed by sodium bicarbonate and brine solution. The crude product was purified by silica gel column chromatography (MeOH:CHCl₃; 3:97) to yield 200 mg of pure compound.

¹H NMR (400 MHz, CDCl₃): δ 5.22-5.45 (8H, m); 3.8-4.0 (1H, m); 2.8 (4H, t), 2.6-2.7 (4H, t), 2.4 (2H, m); 2.2 (6H, s), 2.0 (8H, m), 1.5-1.8 (6H, m); 1.4 (9H, s), 1.2-1.4 (34H, m), 0.9 (6H, t).

ESI-MS: 785.6 (M+1)⁺

The above compound (200 mg, 0.25 mmol) was taken in 50 mL RB flask and dissolved in 4 mL dry DCM under argon atmosphere. Trifluoroacetic acid (2 mL) was added dropwise at 0° C. The reaction mixture was stirred for 3 hr. The solvent was washed with sodium bicarbnonate solution followed by brine. The reaction mixture was purified by silica gel column chromatography using chloroform and methanol solvent system (95:5) to yield 120 mg of pure compound 11 (2-amino-6-(dimethylamino)-N',N'-di((9Z,12Z)-octadeca-9,12-dien-1-yl)hexanehydrazide) as semi solid.

¹H NMR (400 MHz, CDCl₃): δ 5.22-5.45 (8H, m); 3.4 (1H, m), 2.8 (4H, t), 2.7 (4H, t), 2.5 (2H, t), 2.4 (6H, s), 2.0 (m), 1.6 (2H, m), 1.4-1.5 (6H, m), 1.2-1.4 (34H, m), 0.9 (6H, t)

ESI-MS: 686.6 (M+1)⁺

Synthesis of Lipid 14 reaction was quenched with sodium hydroxide solution followed by washing with water and brine solution. The solvent was evaporated and the residue was purified by silica column chromatography (EtOAc:Hexane (5:95) to yield 1.5 g (55%) of pure white color compound N,N-dilinoleyl-hydroxylamine.

¹H NMR (400 MHz, CDCl₃): δ 5.27-5.39 (8H, m); 2.77 (4H, t, J=6.84 Hz), 2.57-2.68 (4H, m), 2.05 (8H, q, J=6.80, 6.87 Hz); 1.50-1.65 (4H, m), 1.22-1.42 (32H, m), 0.89 (6H, t, J=6.86 Hz).

ESI-MS: 530 [M+1]⁺

N,N-dilinoleyl-hydroxylamine (0.48 g, 0.90 mmol, 1 equiv.) N, N-dimethyl aminobutyric acid hydrochloride (0.30 g, 1.8 mmol, 2 equiv.), EDCI (0.34 g, 1.8 mmol, 2 equiv.) and DMAP (0.01 g, 0.09 mmol, 0.1 equiv.) were dissolved in dry DCM under argon atmosphere. Then trimethylamine (0.25 ml, 1.8 mmol, 2 equiv.) was added and the reaction was stirred for 24 hr. The reaction mixture was washed with water, followed by sodium bicarbonate and brine solution. The solvent was evaporated and the residue was purified by silica gel column chromatography (MeOH:CHCl3 (3:97) to yield 0.6 g (85%) of pure lipid 14 as colorless liquid.

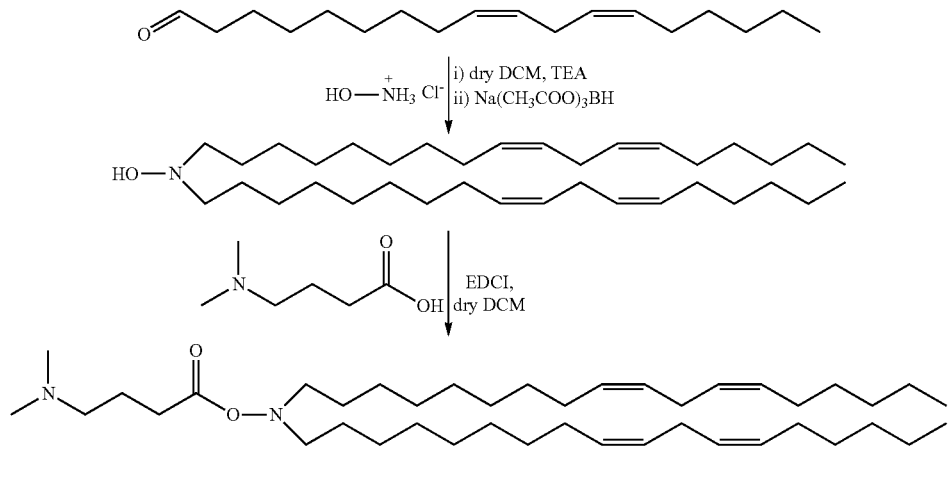

Linoleyl aldehyde (2.64 g, 10.0 mmol, 2 equiv.) and hydroxylamine hydrochloride (0.34 g, 5.0 mmol, 1.0 equiv.) were dissolved in dry DCM under argon atmosphere then trimethylamine (0.7 ml, 5.0 mmol, 1.0 equiv.) was added. After dissolving the compounds, sodium triacetoxyborohydride (3.1 g, 15.0 mmol, 3 equiv.) was added to the reaction mixture and stirred for 24 hr at room temperature. The ¹H NMR (400 MHz, CDCl₃): δ 5.22-5.45 (8H, m); 2.71-2.87 (8H, m), 2.24-2.36 (4H, m); 2.21 (6H, s); 1.93-2.12 (8H, m); 1.74-1.81 (2H, m); 1.42-1.58 (4H, m); 1.6-1.8 (8H, m); 1.20-1.40 (32H, m), 0.89 (6H, t, J=6.90 Hz).

Mass: 643.1 [M]⁺; 644.1 [M+1]⁺

Synthesis of Lipid 15

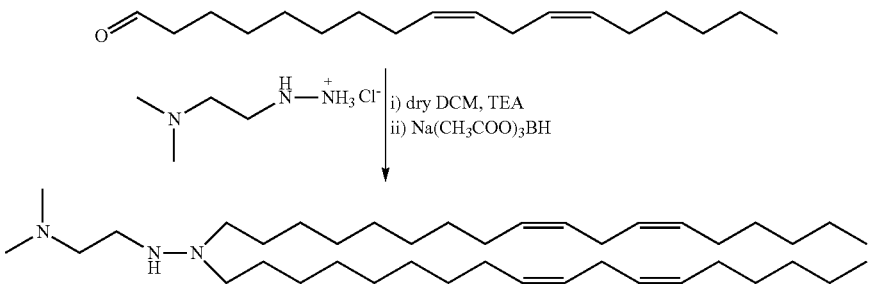

Linoleyl aldehyde (1.7 g, 6.06 mmol, 2 equiv.), N,N-dimethylaminoethyl hydrazine hydrochloride (0.53 g, 3.03 mmol, 1 equiv.) and trimethylamine (0.84 ml, 6.06 mmol, 2 equiv.) were dissolved in dry DCM under argon atmosphere, then sodium tri acetoxyborohydride (1.91 g, 9.09 mmol, 3 equiv.) was added and the reaction mixture was stirred for 24 hr at room temperature. The reaction was quenched with sodium hydroxide solution followed by washing with water and brine solution. The solvent was evaporated and the residue was purified by silica gel column chromatography (MeOH:CHCl$_3$ (3:97) yielded 1.08 g (60%) of pure lipid 15 as colorless liquid.

$^1$H NMR (400 MHz, CDCl$_3$): δ 6.77 (1H, t, J=5.55 Hz), 5.34-5.48 (8H, m); 3.13 (2H, m), 3.00-3.05 (2H, m), 2.77 (4H, t, J=6.44 Hz), 2.41-2.48 (4H, m), 2.22-2.34 (2H, m), 2.28 (s, 6H); 1.46-1.51 (4H, m); 1.32-1.40 (32H, m), 0.89 (6H, t, J=6.90 Hz).

ESI-MS: 599 ([M]$^+$), 600 ([M+1]$^+$).

Synthesis of Lipid 22

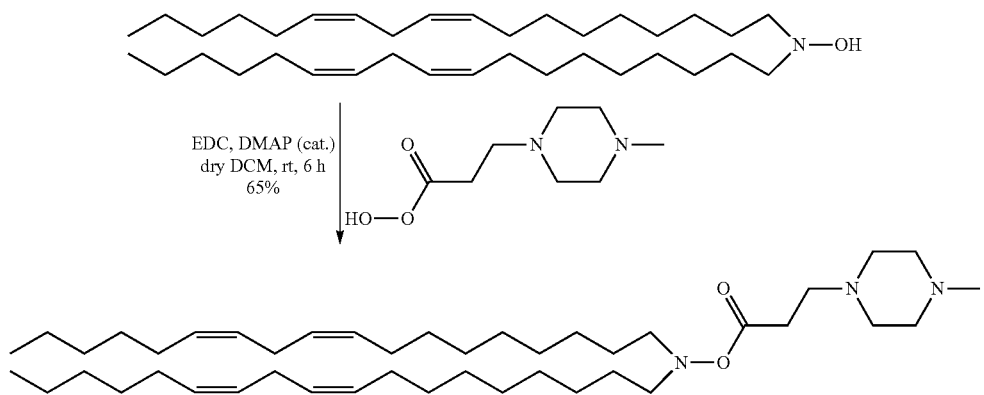

N,N-dilinoleyl-hydroxylamine (0.20 g, 0.37 mmol, 1 equiv.) N-methyl piperazine propanoic acid (0.12 g, 0.74 mmol, 2 equiv.), EDCI (0.13 g, 0.74 mmol, 2 equiv.) and DMAP (5 mg, 0.03 mmol, 0.1 equiv.) were dissolved in dry DCM under argon atmosphere. Then trimethylamine (0.1 ml, 0.74 mmol, 2 equiv.) was added and the reaction was stirred for 24 hr. The reaction mixture was washed with water, followed by sodium bicarbonate and brine solution. The solvent was evaporated and the residue was purified by silica gel column chromatography (MeOH:CHCl$_3$ (5:95) to yield 0.21 g (76%) of pure lipid as colorless liquid.

$^1$H NMR (400 MHz, CDCl$_3$): δ 5.21-5.45 (8H, m); 2.75-2.87 (8H, m), 2.70 (2H, t, J=7.28 Hz); 2.47 (2H, t, J=7.25 Hz); 2.27 (3H, s); 1.98-2.10 (8H, m); 1.44-1.57 (4H, m); 1.15-1.40 (32H, m), 0.88 (6H, t, J=6.81 Hz).

Mass: 684.8 [M+1]$^+$

Synthesis of Lipid 38

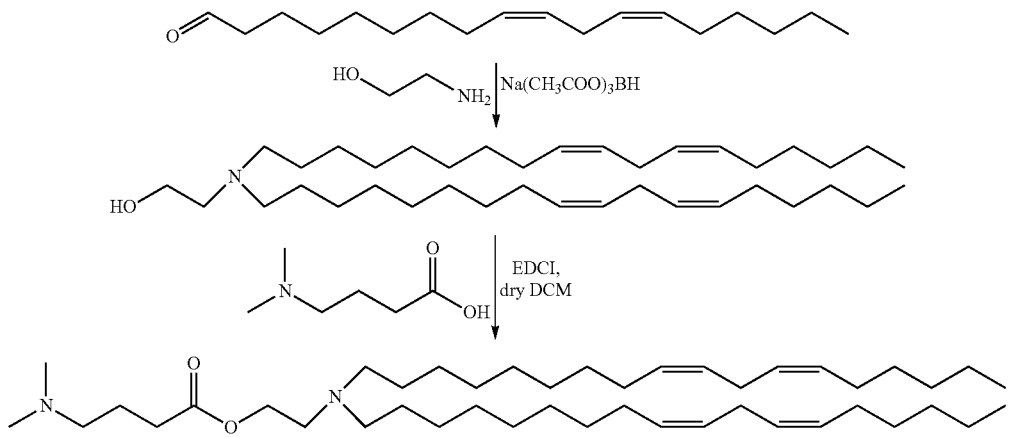

Linoleyl aldehyde (2.64 g, 10.0 mmol, 2 equiv.) and ethanolamine (0.30 g, 5.0 mmol, 1 equiv.) were dissolved in dry DCM under argon atmosphere, then sodium tri acetoxyborohydride (3.1 g, 15.0 mmol, 3 equiv.) was added, and the reaction mixture was stirred for 24 hr at room temperature. The reaction was quenched with sodium hydroxide solution followed by washing with water and brine solution. The solvent was evaporated and the residue was purified by column chromatography (MeOH:CHCl$_3$ (2:98) to yield 2.3 g (85%) of pure yellowish color compound N,N-dilinoleyl-aminoethanol.

$^1$H NMR (400 MHz, CDCl$_3$): δ 5.35-5.46 (8H, m); 3.52 (2H, t, J=5.38 Hz); 2.77 (4H, t, J=6.37 Hz), 2.57 (2H, t, J=5.38 Hz), 2.43-2.49 (4H, m), 2.05 (8H, q, J=6.73, 6.75 Hz), 1.43-1.48 (4H, m), 1.32-1.38 (32H, m), 0.89 (6H, t, J=6.85 Hz)

ESI-MS: 558 [M+1]$^+$

N, N-dilinoleyl-aminoethanol (0.55 g, 1.0 mmol, 1 equiv.), N,N-dimethyl aminobutyric acid (0.33 g, 2.0 mmol, 2 equiv.), EDCI (0.38 g, 2.0 mmol, 2 equiv.) and DMAP (0.01 g, 0.01 mmol, 0.1 equiv.) were dissolved in dry DCM under argon atmosphere. Trimethylamine (0.28 ml, 2.00 mmol, 2 equiv.) was added and the reaction mixture was stirred for 24 hr. The reaction mixture was washed with water, followed by sodium bicarbonate and brine solution. The solvent was evaporated and the residue was purified by silica gel column chromatography (MeOH:CHCl$_3$ (3:97) to yield 0.46 g (70%) of pure lipid 38 as colorless liquid.

$^1$H NMR (400 MHz, CDCl$_3$): δ 5.27-5.45 (8H, m); 4.12 (2H, t, J=6.33 Hz); 2.77 (4H, t, J=6.37 Hz); 2.67 (2H, t, J=6.34 Hz); 2.38-2.49 (4H, m), 2.19-2.38 (4H, m); 2.21 (6H, s); 2.05 (8H, q, J=6.82, 6.84 Hz); 1.70-1.85 (4H, m); 1.20-1.50 (36H, m), 0.9 (6H, t, J=6.85 Hz).

ESI-MS: 671 ([M]$^+$), 672 ([M+1]$^+$).

Synthesis of Lipids 54 and 57

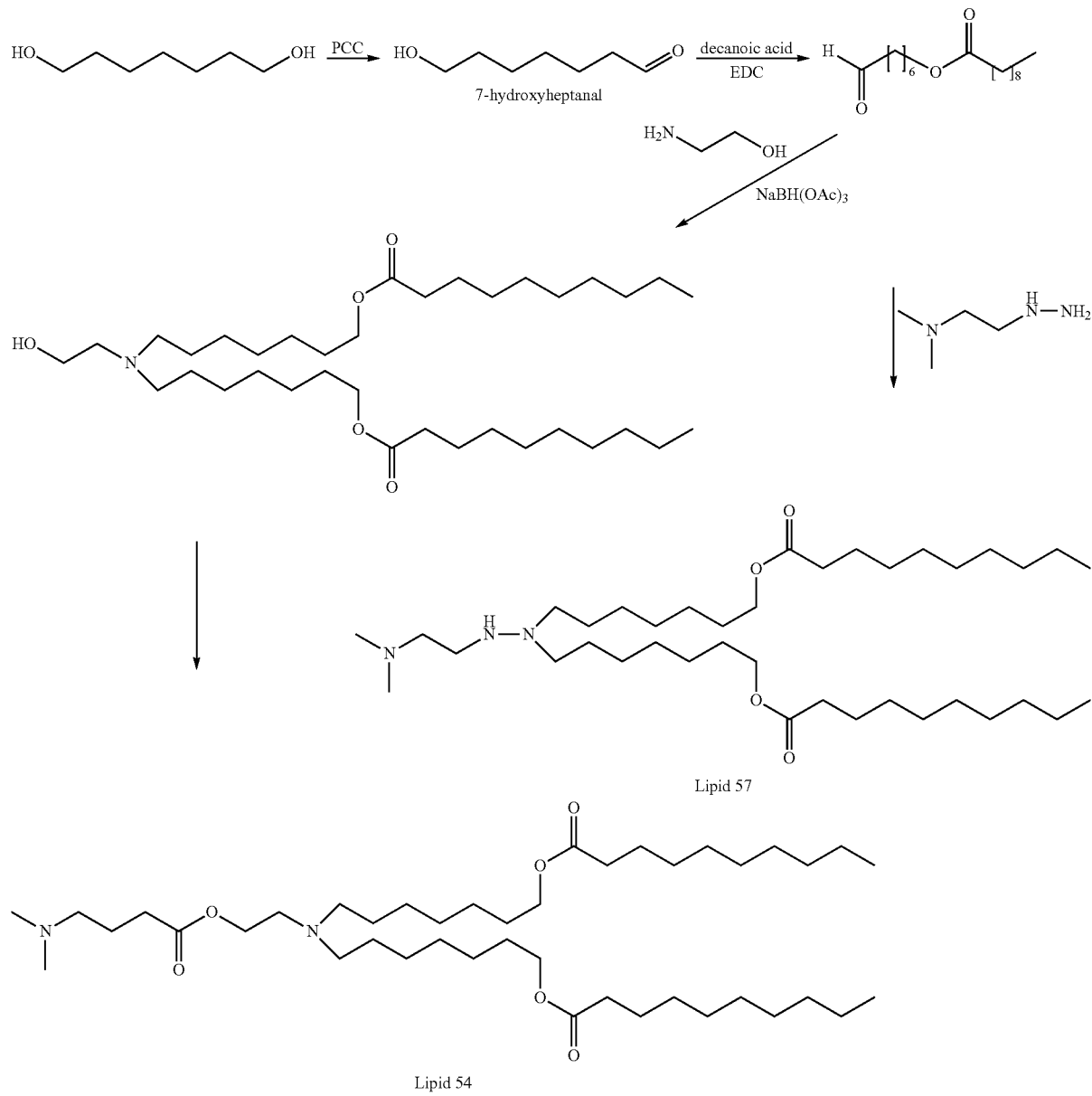

Lipid 57

Lipid 54

7-oxoheptyl decanoate

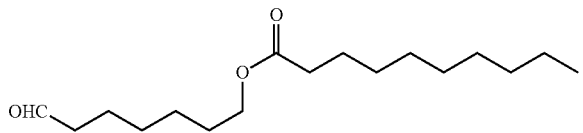 [SMILES: CCCCCCCCCC(=O)OCCCCCCC=O]

1,7-heptanediol (5 g, 37 mmol) was taken in a 100 mL flask and dissolved in dry DCM followed by portion-wise slow addition of PCC (8.9 g, 41.6 mmol) for 15 min. Then, the reaction mixture was stirred at room temperature for 2 h. The crude reaction mixture was filtered through a silica gel pad and washed with DCM (2×50 mL). The organic solvent was dried over with $Na_2SO_4$ and the solvent was removed under reduced pressure. The obtained crude hydroxyl aldehyde was used directly without any further purification.

The crude hydroxy aldehyde (1.3 g, 10.0 mmol), decanoic acid (2.0 g, 12.0 mmol) and EDC (2.8 g, 15.0 mmol) were taken in a 100 mL flask and dissolved in dry DCM and addition of DMAP (cat.) at 0° C. The reaction mixture was stirred for 24 hr at RT. The reaction mixture was then washed with water followed by brine solution and dried over anhydrous $Na_2SO_4$. The crude mixture was purified by silica column chromatography (EtOAc:Hexane (05:95) to give colorless oil with 90% (2.4 g) yield.

$^1$H NMR (400 MHz, $CDCl_3$): δ 9.76 (1H, t, J=1.91 Hz); 4.05 (2H, t, J=6.76 Hz), 2.43 (2H, dt, J=7.48, 5.70 Hz); 2.28 (2H, t, J=7.68 Hz); 1.78-1.52 (8H, m); 1.44-1.33 (4H, m); 1.32-1.20 (12H, m), 0.87 (3H, t, J=6.62 Hz).

Mass: 285.8 $[M+1]^+$, 283.8 $[M-1]^+$

(2-(2-(dimethylamino)ethyl)hydrazine-1,1-diyl)bis(heptane-7,1-diyl) bis(decanoate) (Lipid 57)

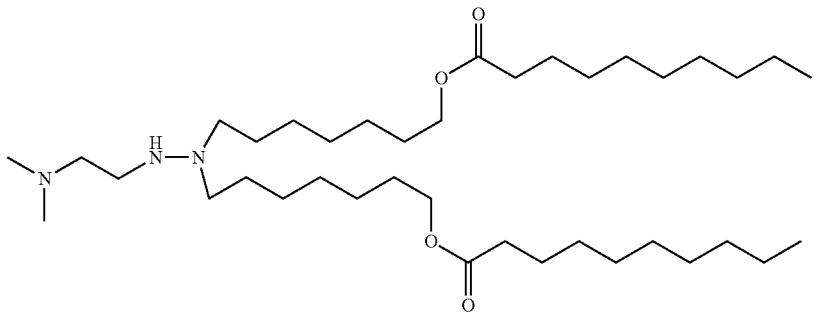 [SMILES: CCCCCCCCCC(=O)OCCCCCCCN(CCCCCCCOC(=O)CCCCCCCCC)NCCN(C)C]

7-oxoheptyl decanoate (0.6 g, 2.2 mmol) and dimethylaminoethyl hydrazine hydrochloride (0.18 g, 1.0 mmol) were dissolved in dry DCM followed by addition of trimethylamine (0.1 ml). Sodium triacetoxyborohydride (0.6 g, 3.0 mmol) was added to the reaction mixture and stirred for 24 hr at room temperature. The reaction mixture was washed with $NaHCO_3$ solution followed by brine solution and dried over sodium sulphate. The crude mixture was purified by silica gel column chromatography (MeOH:$CHCl_3$ (5:95) to yield 73% (0.51 g) pure (2-(2-(dimethylamino)ethyl)hydrazine-1,1-diyl)bis(heptane-7,1-diyl) bis(decanoate) as pale yellow liquid.

$^1$H NMR (400 MHz, $CDCl_3$): δ 9.28 (1H, t, J=5.55 Hz); 4.01 (1H, t, J=6.60 Hz), 3.70 (2H, t, J=7.70 Hz), 3.30-3.20 (3H, m), 2.54 (3H, t, J=7.55 Hz), 2.33-2.21 (6H, m), 2.20 (s, 6H); 1.80-1.70 (4H, m); 1.37-1.17 (24H, m), 0.83 (6H, t, J=6.90 Hz).

ESI-MS: 640 ($[M+1]^+$).

((2-hydroxyethyl)azanediyl)bis(heptane-7,1-diyl) bis(decanoate)

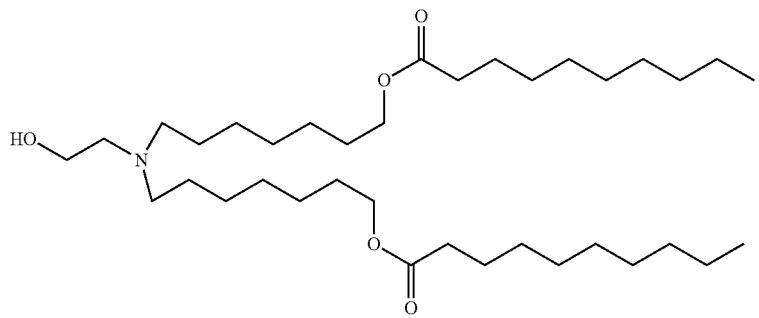 [SMILES: CCCCCCCCCC(=O)OCCCCCCCN(CCO)CCCCCCCOC(=O)CCCCCCCCC]

7-oxoheptyl decanoate (1.0 g, 3.7 mmol) and ethanolamine (0.11 g, 1.85 mmol) were dissolved in dry DCM followed by addition of sodium tri acetoxyborohydride (1.1 g, 5.5 mmol), and the reaction mixture was stirred for 24 hr at room temperature. The reaction mixture was washed with sodium bicarbonate solution followed by brine solution and dried over sodium sulphate. The crude mixture was was purified by silica gel column chromatography (MeOH: CHCl$_3$ (2:97) to yield 85% (0.91 g) of pure ((2-hydroxyethyl)azanediyl)bis(heptane-7,1-diyl) bis(decanoate) as pale liquid.

$^1$H NMR (400 MHz, CDCl$_3$): δ 4.05 (4H, t, J=6.98 Hz); 3.60 (2H, t, J=5.31 Hz); 2.66 (2H, t, J=5.31 Hz); 2.54 (4H, t, J=7.58 Hz); 2.28 (4H, t, J=7.58 Hz); 1.68-1.54 (8H, m); 1.53-1.41 (4H, m); 1.20-1.40 (32H, m), 0.89 (6H, t, J=6.80 Hz).

ESI-MS: 598 ([M+1]$^+$).

((2-((4-(dimethylamino)butanoyl)oxy)ethyl)
azanediyl)bis(heptane-7,1-diyl) bis(decanoate)
(Lipid 54)

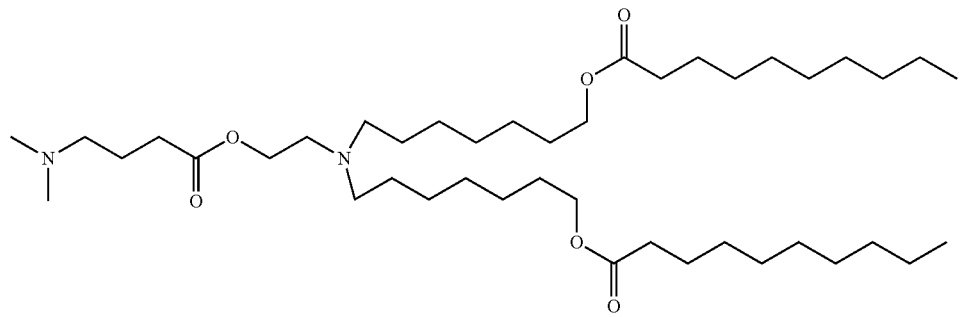 [SMILES: CCCCCCCCCC(=O)OCCCCCCCN(CCCCCCCOC(=O)CCCCCCCCC)CCOC(=O)CCCN(C)C]

((2-hydroxyethyl)azanediyl)bis(heptane-7,1-diyl) bis(decanoate) (0.4 g, 0.7 mmol) and 4-(dimethylamino)butanoic acid (0.17 g, 1.0 mmol) was taken in 100 mL flask and dissolved in dry DCM. Than EDCI (0.27 g, 1.4 mmol) was added to the reaction mixture followed by DMAP (cat.) and stirred it for overnight. The reaction mixture was washed with water followed by brine solution and dried over Na$_2$SO$_4$. The crude mixture was purified by silica gel column chromatography (MeOH:CHCl$_3$ (2:98) to yield 75% (0.37 g) pure ((2-((4-(dimethylamino)butanoyl) oxy)ethyl) azanediyl)bis(heptane-7,1-diyl) bis(decanoate) as pale liquid.

$^1$H NMR (400 MHz, CDCl$_3$): δ 4.11 (2H, t, J=6.51 Hz); 4.04 (4H, t, J=6.78 Hz); 2.66 (2H, t, J=6.51 Hz); 2.43 (4H, t, J=7.73 Hz); 2.33 (2H, t, J=7.58 Hz); 2.28 (4H, t, J=7.58 Hz); 2.21 (6H, s); 1.68-1.54 (6H, m); 1.67-1.52 (8H, m); 1.46-1.36 (4H, m); 1.20-1.40 (32H, m), 0.87 (6H, t, J=6.80 Hz).

ESI-MS: 711 ([M+1]$^+$).

Synthesis of Lipid 24

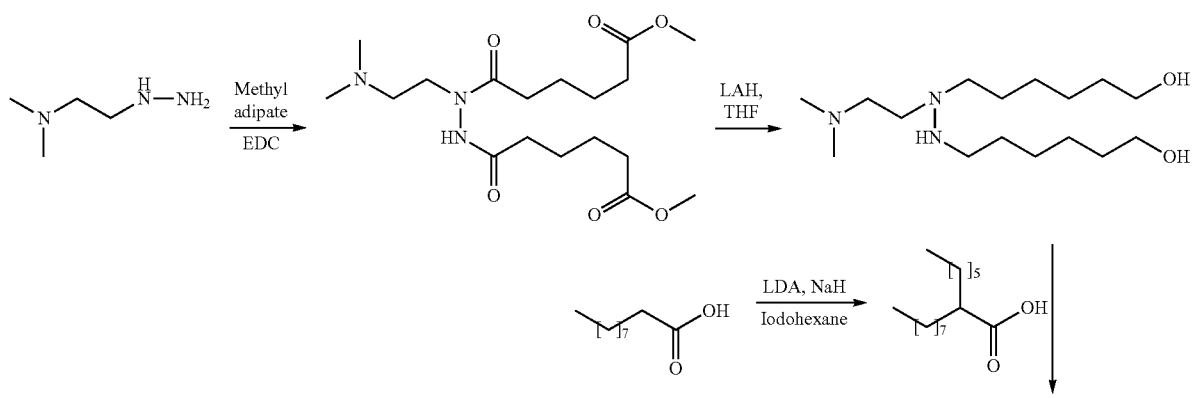

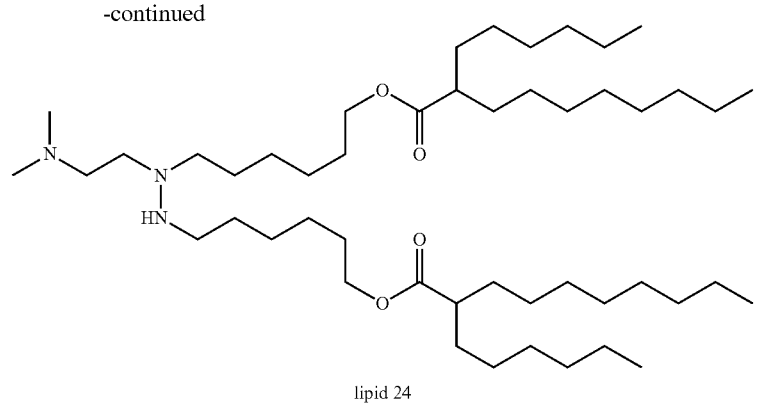

lipid 24

2-hexyldecanoic acid

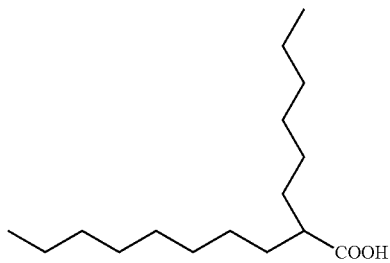 [SMILES: CCCCCCCCC(CCCCCC)C(=O)O]

The freshly prepared LDA (9.0 mL, 2M in THF, 18.0 mmol) in THF (30 mL) was slowly added to a solution of decanoic acid (2.6 g, 15.3 mmol) and NaH (60 w/w % mineral oil suspension, 690 mg, 18.0 mmol) in THF (19 mL) at 0° C. and stirred for 30 min at room temperature. After addition of n-$C_6H_{13}I$ (2.6 mL, 18.0 mmol), the reaction mixture was stirred for 6 h at 45° C. then quenched with 1N HCl at room temperature. The organic layer was dried over anhydrous $Na_2SO_4$ and concentrated under reduced pressure. The residue was purified by flash silica column chromatography (EtOAc:Hex (10:90)) to give (3.7 g, 65%) as a colorless liquid.

$^1$H NMR (400 MHz, $CDCl_3$): δ 2.38-2.28 (1H, m); 1.69-1.53 (2H, m); 1.50-1.40 (2H, m); 1.36-1.20 (20H, m); 0.87 (6H, t, J=6.87 Hz).

Mass: 255 [M−1]$^+$

Dimethyl 6,6'-(1-(2-(dimethylamino)ethyl)hydrazine-1,2-diyl)bis(6-oxohexanoate)

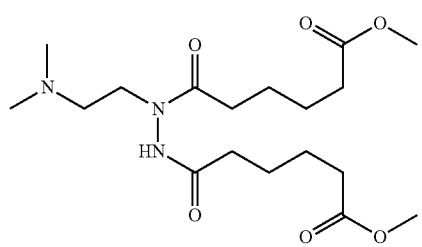

Methyl adipate (1.6 g, 10.0 mmol), dimethylaminoethyl hydrazine (0.88 g, 5.0 mmol) and EDC (2.8 g, 15.0 mmol) were dissolved in dry DCM followed by addition of triethyl amine. The reaction mixture was stirred for overnight. The reaction mixture was washed with water followed by brine solution and dried over sodium sulphate. The crude mixture was purified by column chromatography (MeOH:$CHCl_3$ (5:95) to give pale yellow liquid.

$^1$H NMR (400 MHz, $CDCl_3$): δ 3.66 (3H, s); 3.64 (3H, s); 2.26-2.41 (6H, m); 2.15-2.26 (12H, s); 1.65-1.54 (4H, m); 1.65-1.55 (4H, m).

Mass: 388 [M+1]$^+$ 6,6'-(1-(2-(dimethylamino)ethyl)hydrazine-1,2-diyl)bis(hexan-1-ol)

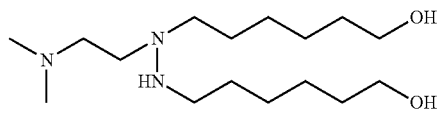 [SMILES: CN(C)CCN(CCCCCCO)NCCCCCCO]

Dimethyl-6,6'-(1-(2-(dimethylamino)ethyl)hydrazine-1,2-diyl)bis(6-oxohexanoate) (0.77 g, 2.0 mmol) was dissolved in dry THF followed by addition of excess LAH (10.0 mL, 2M in THF, 20.0 mmol). The reaction mixture was refluxed for 24 hr, quenched by slow addition of $H_2O$ and filtered and dried over $Na_2SO_4$. The solvent removed by under reduced pressure purified by silica gel column chromatography to yield 90% (0.5 g) pure 6,6'-(1-(2-(dimethylamino)ethyl)hydrazine-1,2-diyl)bis(hexan-1-ol).

$^1$H NMR (400 MHz, $CDCl_3$): δ 3.62 (4H, t, J=6.70 Hz); 2.70 (2H, t, J=6.87 Hz); 2.65 (2H, t, J=7.10 Hz); 2.50-2.60 (4H, m,); 2.44 (2H, t, J=6.91 Hz); 2.29 (6H, s); 1.65-1.45 (6H, m); 1.44-1.25 (8H, m).

ESI-MS: 304 ([M+1]$^+$).

(1-(2-(dimethylamino)ethyl)hydrazine-1,2-diyl)bis(hexane-6,1-diyl) bis(2-hexyldecanoate) (Lipid 24)

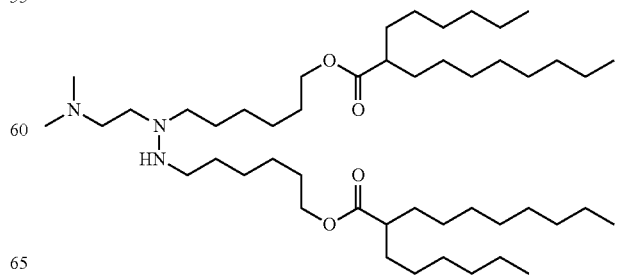

6,6'-(1-(2-(dimethylamino)ethyl)hydrazine-1,2-diyl)bis(hexan-1-ol) (0.30 g, 1.0 mmol) and 2-hexyl-decanoic acid (0.50 g, 2.2 mmol, 2 equiv.) were taken in 50 mL flask and dissolved in dry DCM. Than EDC (0.27 g, 1.4 mmol) was added to the reaction mixture followed by DMAP (cat.), and the reaction was stirred for overnight. The reaction mixture was washed with water followed by brine solution and dried over Na$_2$SO$_4$. The crude mixture was purified by silica gel column chromatography (MeOH:CHCl$_3$ (5:95) to yield 65% (0.49 g) pure compound as pale liquid.

$^1$H NMR (400 MHz, CDCl$_3$): δ 3.72 (4H, t, J=5.65 Hz); 3.20-3.34 (4H, m); 2.31 (4H, t, J=6.71 Hz); 2.21 (6H, s); 1.71-1.85 (4H, m); 1.68-1.50 (6H, m); 1.50-1.36 (6H, m); 1.32-1.17 (50H, m), 0.84 (12H, t, J=6.91 Hz).

ESI-MS: 780 ([M+1]$^+$).

Synthesis of Lipid 56

The mixture was stirred at room temperature overnight. The solution was washed with ethyl acetate to remove some organic impurities. The aqueous layer was acidified to pH 3-4 with concentrated HCl 37% and then extracted with ethyl acetate (2×50 mL). The organic layer was washed with saturated NaCl (2×50 mL), dried with Na$_2$SO$_4$, and filtered. The organic layer was concentrated in vacuo to yield>90% (2.0 g) as colorless oil.

$^1$H NMR (400 MHz, CDCl$_3$): δ 3.62 (2H, t, J=6.30 Hz); 2.33 (2H, t, J=7.45 Hz); 1.63 (2H, pent); 1.55 (2H, q, J=7.45 Hz); 1.42-1.32 (2H, m).

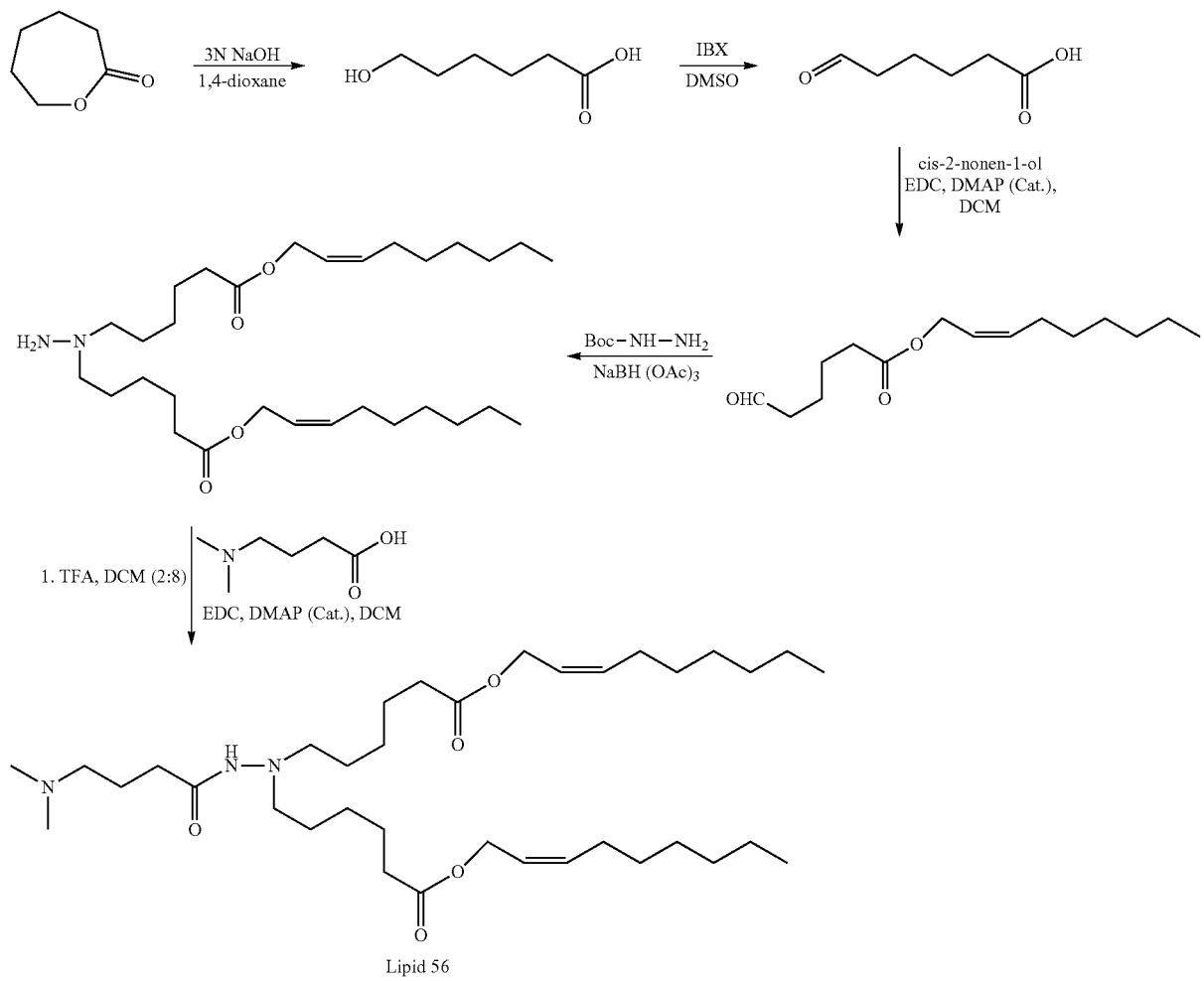

6-hydroxyhexanoic acid

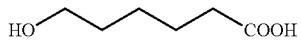

7-oxoheptanoic acid

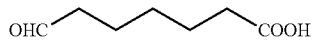

ε-caprolactone (2.2 g, 20.0 mmol) was dissolved in dioxane 6 mL, and 50 ml of a 3M NaOH solution was added.

IBX (1.0 g, 3.5 mmol, 1.5 eq) was added to a solution of 6-hydroxyhexanoic acid (0.60 g, 4.5 mmol) in DMSO (10 mL). The mixture was stirred for 6 h and quenched by addition of water. The precipitate was removed by filtration. Extraction with ethyl acetate (2×50 ml), anhydrification with Na$_2$SO$_4$, and removal of the solvent in vacuo gave almost pure oxoacid yield 0.46 g (78%) as colorless oil.

$^1$H NMR (400 MHz, CDCl$_3$): δ 9.48 (1H, t, J=1.57 Hz); 2.33 (2H, t, J=7.45 Hz); 2.20 (2H, t, J=7.20 Hz); 2.10-1.95 (2H, m), 1.45-1.32 (2H, m).

(Z)-non-2-en-1-yl 6-oxohexanoate

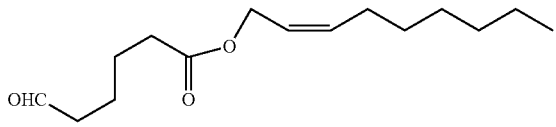 [SMILES: CCCCCC/C=C\COC(=O)CCCCC=O]

7-oxoheptanoic acid (0.26 g, 2.0 mmol) and cis-2-nonen-1-ol (0.28 g, 2.0 mmol, 1 equiv.) taken in 50 mL flask and dissolved in dry DCM and EDCI (0.27 g, 1.4 mmol) was added to the reaction mixture followed by DMAP (cat) stirred for overnight. The reaction mixture was washed with water followed by brine solution and dried over sodium sulphite. The crude mixture was purified by silica gel column chromatography (EtOAc:Hexane (5:95) to yield 85% (0.44 g) pure compound as liquid.

$^1$H NMR (400 MHz, CDCl$_3$): δ 9.74 (1H, t, J=1.69 Hz), 5.68-5.58 (1H, m); 5.54-5.44 (1H, m); 4.60 (2H, d, J=7.20 Hz); 2.40-2.50 (2H, m); 2.38-2.28 (2H, m); 2.08 (2H, q, J=7.70, 6.90 Hz); 1.70-1.60 (4H, m); 1.40-1.20 (8H, m); 0.86 (6H, t, J=6.95 Hz).

ESI-MS: 277 ([M+Na]$^+$).

Di((Z)-non-2-en-1-yl) 6,6'-(2-(tert-butoxycarbonyl)hydrazine-1,1-diyl)dihexanoate

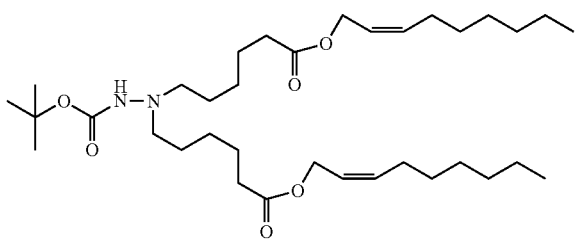 [SMILES: CCCCCC/C=C\COC(=O)CCCCCN(CCCCCC(=O)OC/C=C\CCCCCC)NC(=O)OC(C)(C)C]

(Z)-non-2-en-1-yl 6-oxohexanoate (0.25 g, 1.0 mmol, 2 equiv.) and Boc-hydrazine (0.06 g, 0.5 mmol, 1.0 equiv.) were dissolved in dry DCM under nitrogen atmosphere then sodium tri acetoxyborohydride (0.63 g, 3.0 mmol, 3.0 equiv) was added to the reaction mixture and stirred for 12 h at room temperature. The reaction was quenched with sodium bicarbonate solution and extracted with DCM followed by washing with water and brine solution. The solvent was evaporated and purified by column chromatography (EtOAc:Hexane (10:90) to yield 0.21 g (78%) of pure lipid as colorless liquid.

$^1$H NMR (400 MHz, CDCl$_3$): δ 5.60-5.50 (2H, m); 5.47-5.37 (2H, m); 5.25 (br s, 1H), 4.53 (2H, s), 4.51 (2H, s), 2.65-2.42 (4H, m), 2.21 (4H, t, J=7.50 Hz), 2.00 (4H, q, J=7.90, 7.11 Hz), 1.54 (4H, pent); 1.32-1.45 (15H, m), 1.30-1.09 (18H, m), 0.79 (6H, t, J=6.75 Hz).

ESI-MS: 609 ([M+1]$^+$), 553 ([M-t-Bu]$^+$).

Di((Z)-non-2-en-1-yl) 6,6'-(hydrazine-1,1-diyl)dihexanoate

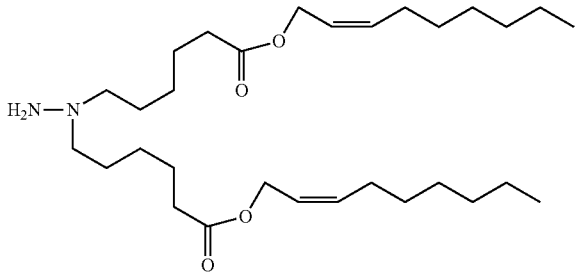 [SMILES: CCCCCC/C=C\COC(=O)CCCCCN(N)CCCCCC(=O)OC/C=C\CCCCCC]

The above Boc-protected-hydrazine compound (0.25 g, 0.41 mmol) was dissolved in TFA/DCM (2:8) 10 mL under nitrogen atmosphere for 2 h at room temperature. The reaction was quenched with sodium bicarbonate solution and extracted with DCM followed by washing with water and brine solution and drying over Na$_2$SO$_4$. The solvent was evaporated to yield, without further purification 0.20 g (99%) of pure hydrazine as pale yellow liquid.

$^1$H NMR (400 MHz, CDCl$_3$): δ 5.70-5.58 (2H, m); 5.56-5.42 (2H, m); 4.62 (2H, s), 4.60 (2H, s); 2.44 (4H, t, J=7.52 Hz); 2.31 (4H, t, J=7.52 Hz); 2.09 (4H, q, J=7.52, 7.15 Hz); 1.64 (4H, pent); 1.55 (4H, pent); 1.43-1.20 (18H, m); 0.87 (6H, t, J=7.15 Hz).

ESI-MS: 509 ([M+1]$^+$)

Di((Z)-non-2-en-1-yl) 6,6'-(2-(4-(dimethylamino)butanoyl)hydrazine-1,1-diyl)dihexanoate (Lipid 56)

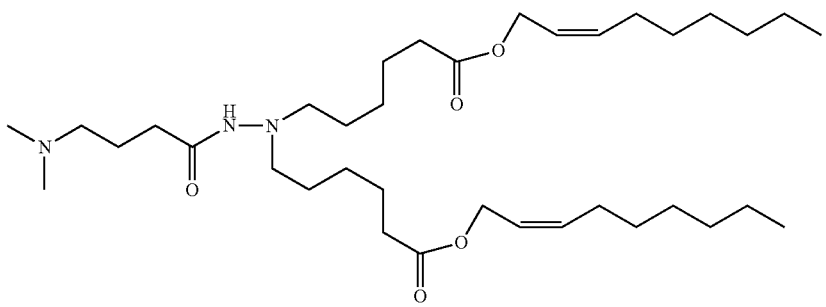 [SMILES: CCCCCC/C=C\COC(=O)CCCCCN(CCCCCC(=O)OC/C=C\CCCCCC)NC(=O)CCCN(C)C]

Di((Z)-non-2-en-1-yl) 6,6'-(hydrazine-1,1-diyl)dihexanoate (0.20 g, 0.4 mmol, 1 equiv.), N,N-dimethyl aminobutyric acid hydrochloride (0.10 g, 0.6 mmol, 1.5 equiv.), EDC (0.15 g, 0.8 mmol, 2.0 equiv.) and DMAP (cat.) were dissolved in dry DCM under nitrogen atmosphere. Then trimethylamine (0.28 ml, 2.00 mmol, 2 equiv.) was added and the reaction was stirred for 12 h. To the reaction mixture was added sodium bicarbonate and the mixture was washed with water, followed by and brine solution and drying over $Na_2SO_4$. The solvent was evaporated and the reaction mixture was purified by silica column chromatography (MeOH:$CHCl_3$ (5:95) to yield 85% (0.20 g) of pure lipid as pale yellow liquid.

$^1$H NMR (400 MHz, $CDCl_3$): δ 5.67-5.57 (4H, m); 5.57-5.44 (4H, m); 4.61 (4H, t, J=5.52 Hz); 2.66 (2H, t, J=8.16 Hz); 2.45 (2H, t, J=7.47 Hz); 2.40 (2H, t, J=7.75 Hz); 2.34-2.20 (4H, m); 2.28 (6H, s); 2.08 (4H, q, J=7.80 Hz); 2.00-1.90 (4H, m); 1.86-1.76 (2H, m); 1.70-1.55 (4H, m), 1.54-1.40 (4H, m), 1.38-1.20 (14H, m), 0.87 (6H, t, J=6.92 Hz).

ESI-MS: 622 ([M+1]$^+$).

Example 3: Physico-Chemical Characterization

| LNP-siRNA formulations | Size (d · nm) | PDI | Zeta-potential (mV) |
|---|---|---|---|
| Dlin-MC3-DMA | 44.5 | 0.18 | −1 |
| Lipid 1 | 45.1 | 0.14 | 18.5 |
| Lipid 2 | 56.3 | 0.06 | 13.9 |
| Lipid 9 | 75.1 | 0.04 | −13.6 |
| Lipid 10 | 50.5 | 0.08 | 18.5 |
| Lipid 11 | 108.5 | 0.10 | 20.4 |
| Lipid 14 | 44.3 | 0.09 | −3.6 |
| Lipid 15 | 52.5 | 0.11 | 10.1 |
| Lipid 33 | 46.0 | 0.15 | −10.8 |
| Lipid 21 | 67.7 | 0.16 | −2.8 |
| Lipid 38 | 59.0 | 0.08 | 6.7 |
| Lipid 55 | 97.0 | 0.17 | −1.28 |
| Lipid 54 | 138.6 | 0.06 | −1.82 |

Example 4: Biological Results

In vitro gene silencing was performed as described in Example 1.

Figure 1B:
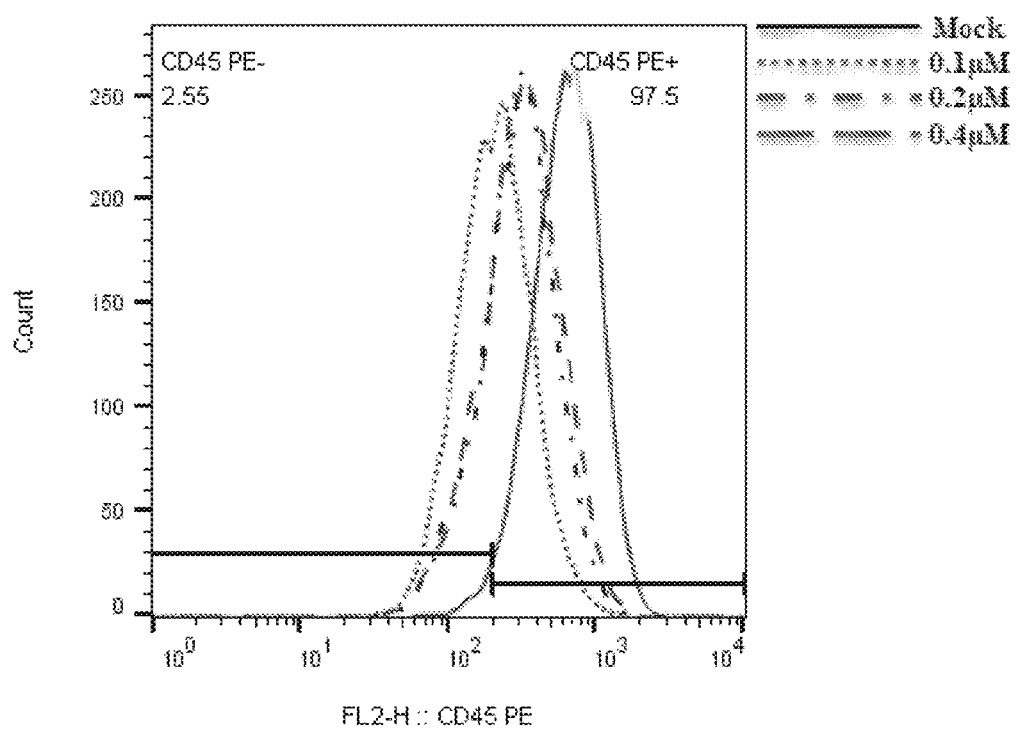

FIG. 1 depicts in vitro gene silencing effect lipid 1: Human T cells SupT1 were treated with lipid nanoparticle (LNP) comprising of cationic lipid 1 encapsulated siCD45 for 48 hrs (A) or 72 hrs (B) at different siRNA doses (0.4 µM, 0.2 µM, 0.1 µM). The results demonstrate the efficiency of the lipid 1 to down-regulate CD45 gene in hard to transfect T cells.

Figure 2A:
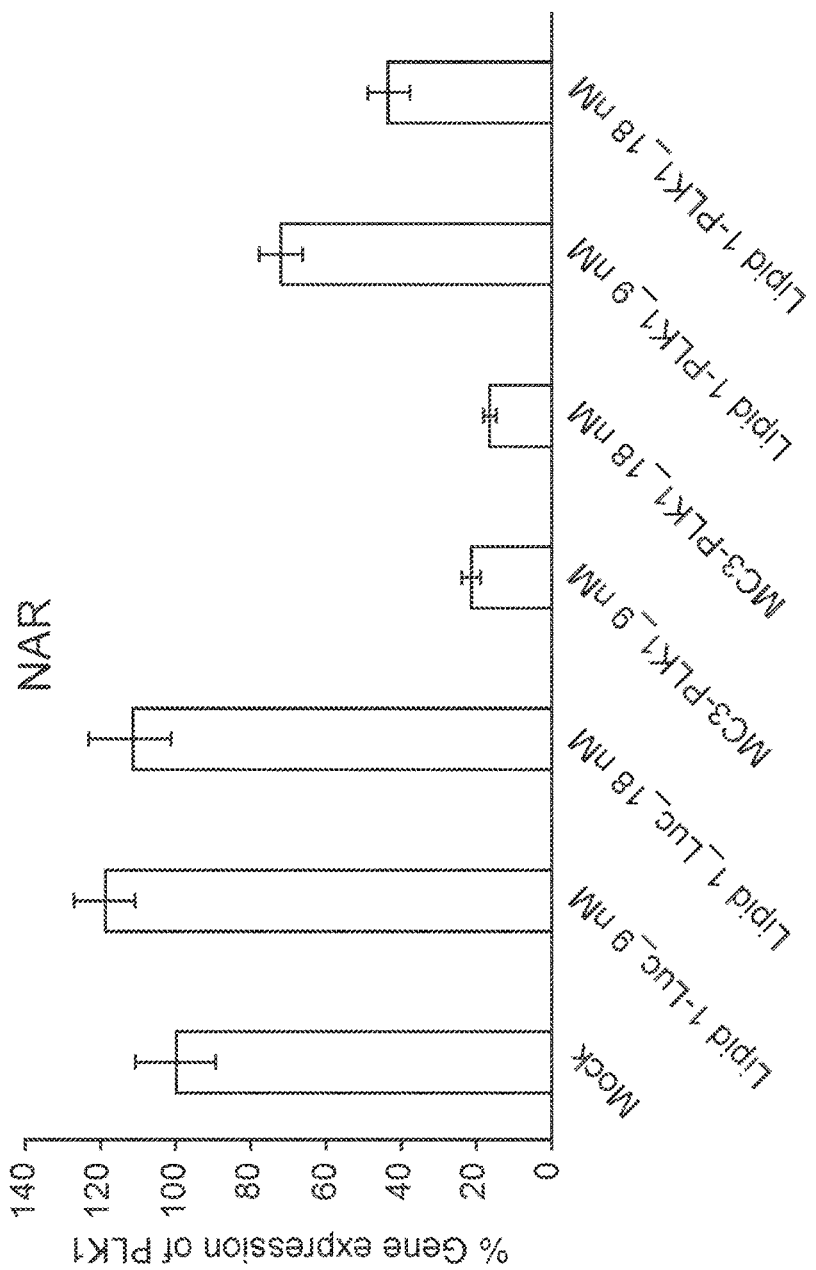
FIG. 2: Drug resistant human ovarian carcinoma cells (NAR) were treated with either LNP-siPLK-1 or LNP-siLuc nanoparticles for 72 hr and PLK-1 expression was measured by qPCR.
Figure 2B:
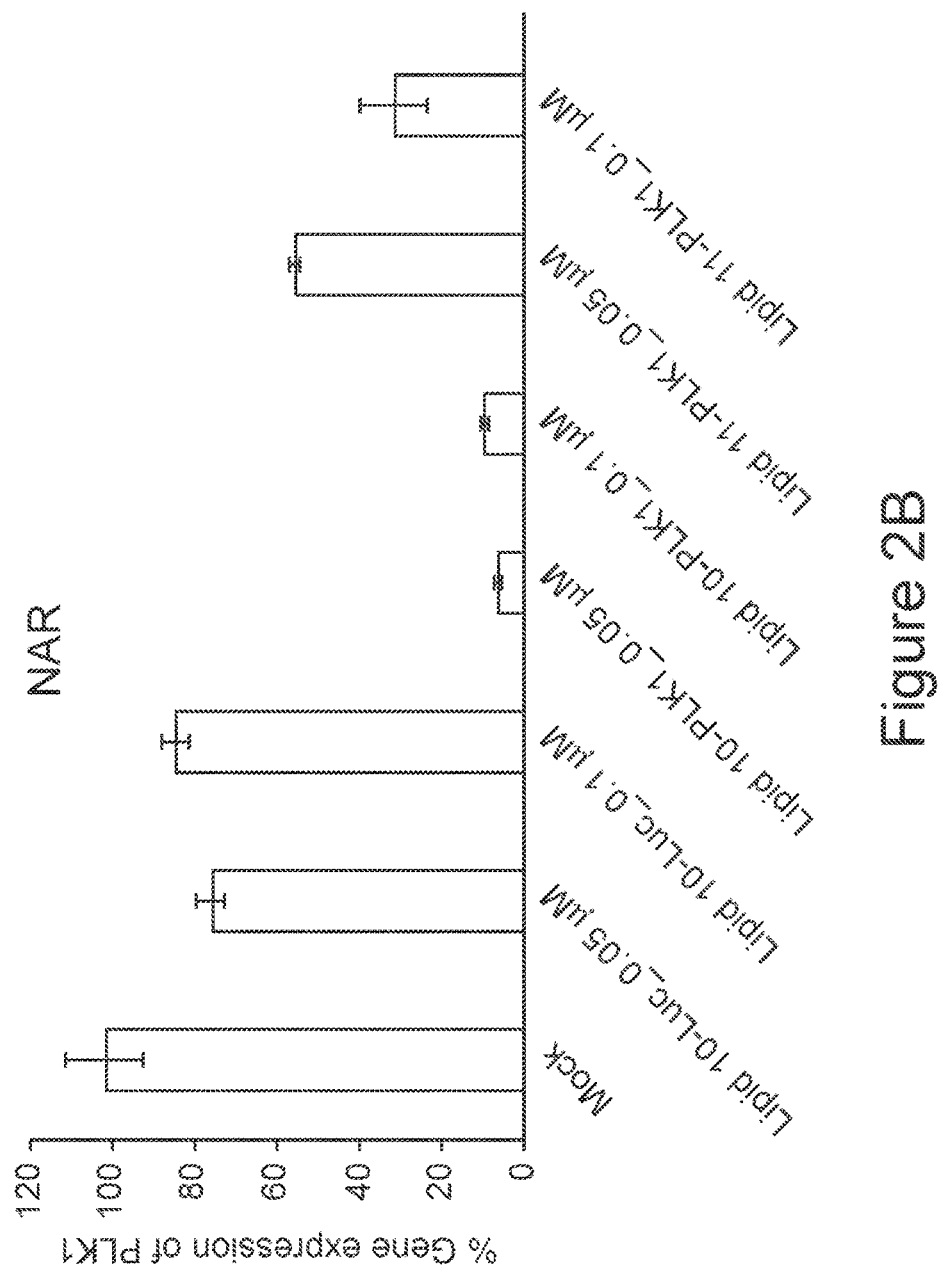

Drug resistant human ovarian carcinoma cells (NAR) were treated with either LNP-siPLK-1 or LNP-siLuc nanoparticles Lipid 1 LNPs (A); Lipid 10&11 LNPs (B) for 72 hrs and PLK-1 expression was measured by qPCR as described in Example 1. As shown in FIG. 2A, Lipid1 containing LNPs downregulating the proto-oncogene PLK1 efficiently, this can induce the apoptosis in cancer cells. At higher doses of cntr LUC-siRNA, LNPs with lipid 1 did not affect plk1 expression. Further as shown in FIG. 2B, lipid 10&11 containing LNPs-siPLK1 also down regulating plk1 gene efficiently at different doses whereas siLUC LNPs has no effect on plk1 expression.

Figure 3:
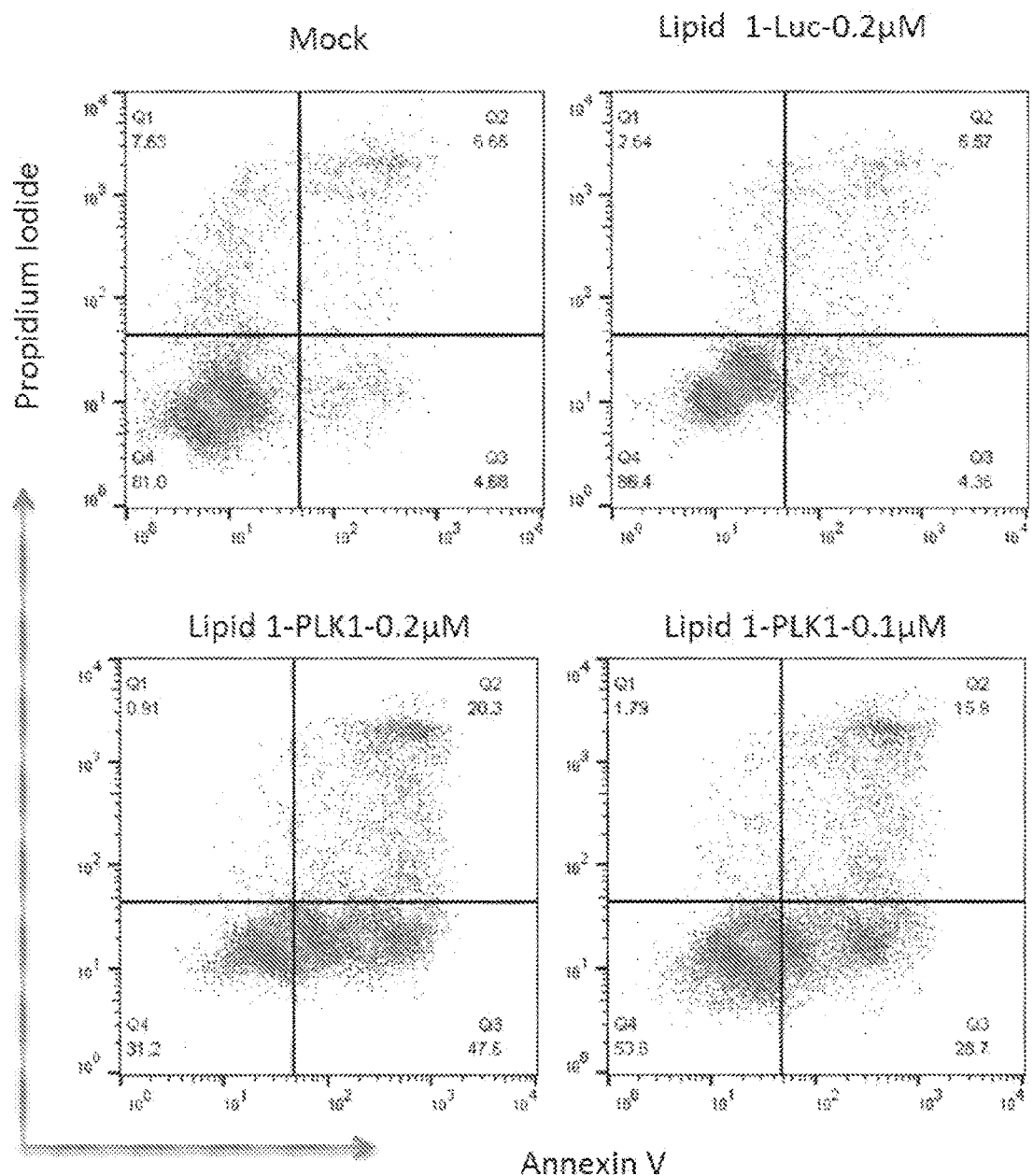
FIG. 3: In vitro gene silencing effect of lipid 1 in NAR cells: Human ovarian cancer cells (NAR cells) were treated with lipid1/siPLK1 nanoparticles for 48 hr at different siRNA concentrations (0.2 μM and 0.1 μM). Apoptotic cells were analyzed by FACS using PI/Annexin.

In Vitro Gene Silencing Effect of Lipid 1 in NAR Cells:

Human ovarian cancer cells (NAR cells) were treated with lipid1/siPLK1 nanoparticles for 48 hr at different siRNA concentrations (0.2 µM and 0.1 µM). Apoptotic cells were analyzed by FACS using PI/Annexin. As shown in FIG. 3, siPLK1-LNPs with lipid1 inducing apoptosis in cancer cell due to downregulation of proto-oncogene plk1. Percentage of early apoptotic cells was higher in cells treated with siPLK1-LNPs at 0.2 uM dose of siPLK1. There was no effect on cell cycle in cells treated with siLUC-LNPs indicating the efficient delivery of siPLK1 to NAR cells.

Figure 4:
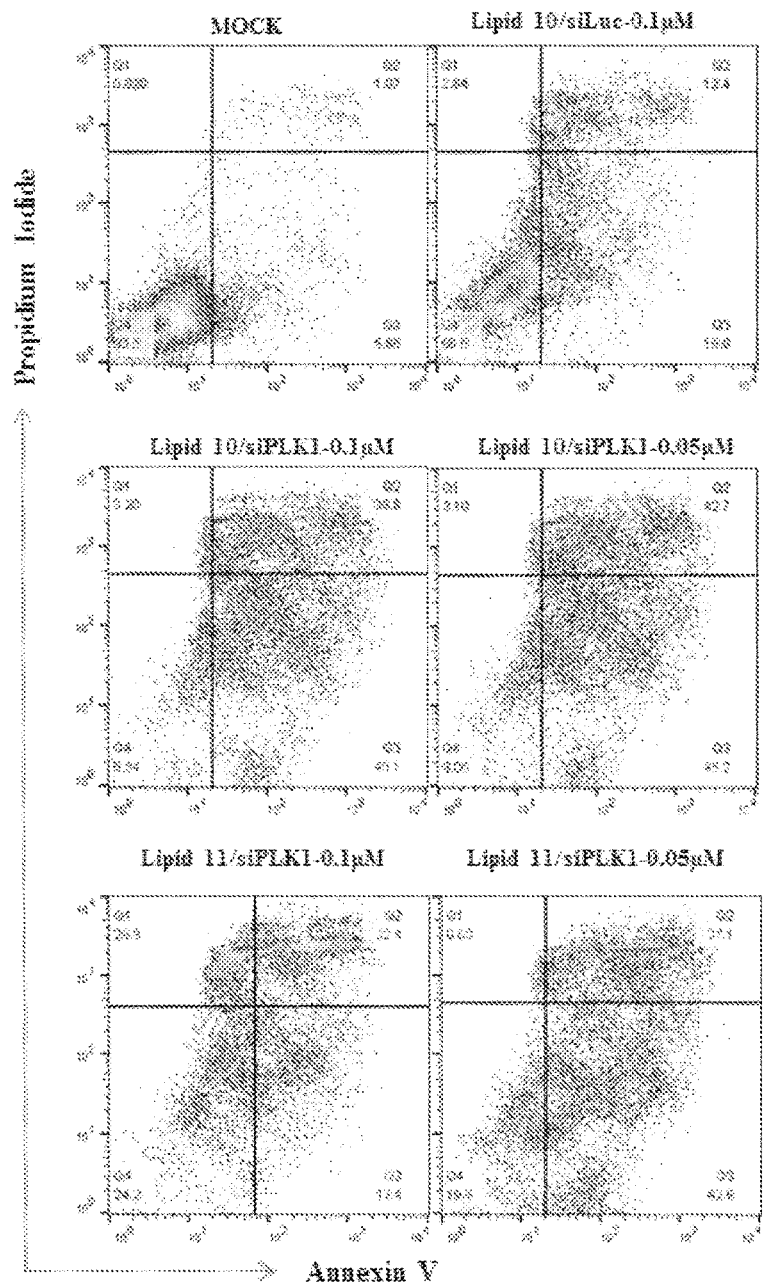
FIG. 4: In vitro gene silencing effect of lipid 10 and 11 in NAR cells: Human ovarian cancer cells (NAR cells) were treated with lipid1/siPLK1 nanoparticles for 48 hr at different siRNA concentrations (0.1 μM and 0.05 μM). Apoptotic cells were analyzed by FACS using PI/Annexin.

In Vitro Gene Silencing Effect of Lipid 10 and 11 in NAR Cells:

Human ovarian cancer cells (NAR cells) were treated with either lipid10 or lipid 11/siPLK1 nanoparticles for 48 hr at different siRNA concentrations (0.1 µM and 0.05 µM). siLUC-LNPs used as a negative control. Apoptotic cells were analyzed by FACS using PI/Annexin. As shown in FIG. 4, siPLK1-LNPs composed of either lipid10 or lipid 11 efficiently downregulating PLK1 gene followed by inducing apoptosis in NAR cells.

Figure 5:
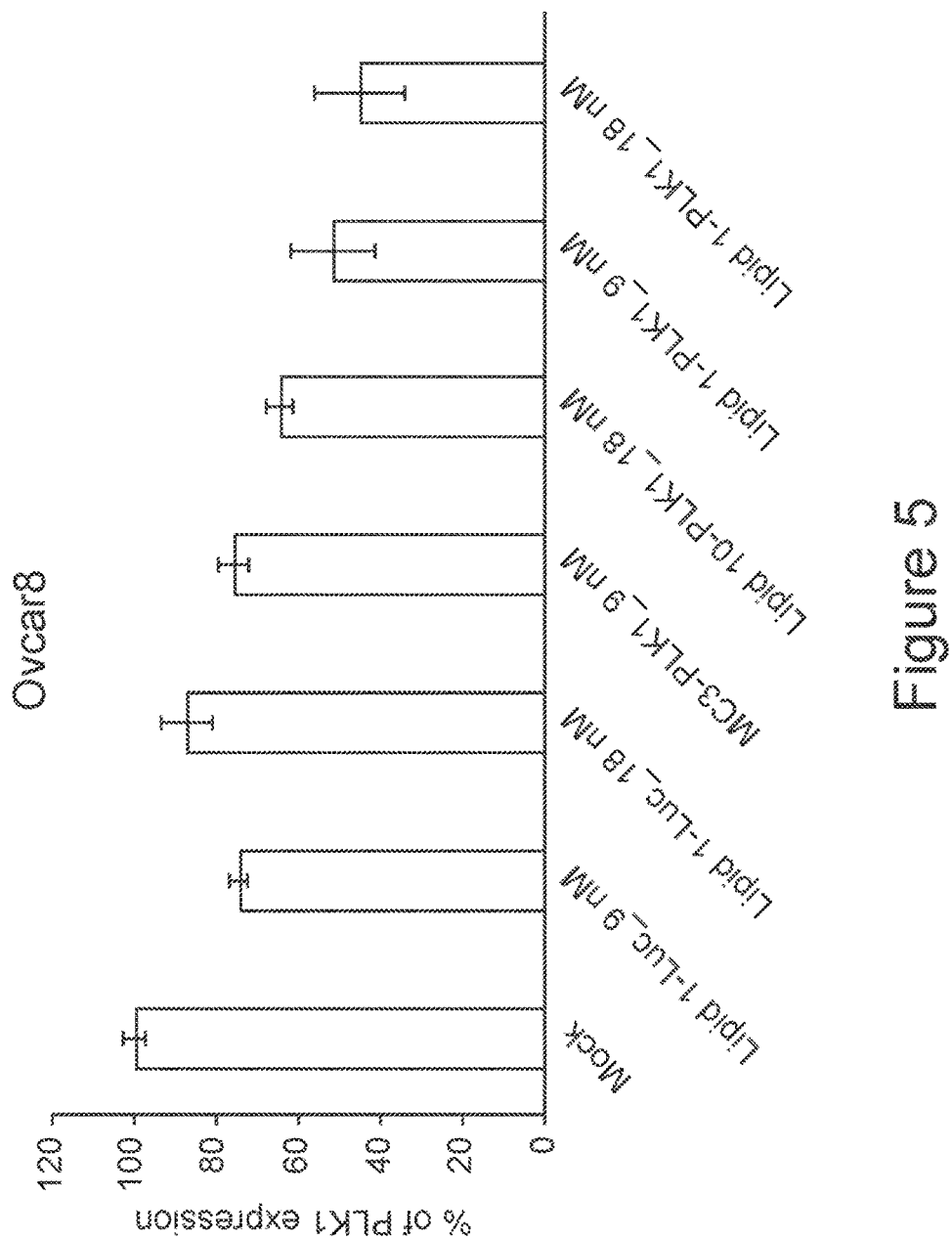
FIG. 5: Human ovarian carcinoma cells (OVCAR 8) were treated with either LNP-siPLK-1 or LNP-siLuc nanoparticles for 72 hr and PLK-1 expression was measured by qPCR.

Human ovarian carcinoma cells (OVCAR 8) were treated with lipid 1 containing LNPs with either siPLK1 or siLUC for 72 hr and PLK-1 expression was measured by qPCR. As shown in FIG. 5, lipid 1 containing siPLK1-LNPs efficiently downregulating PLK1 gene compared to dlin-mc3-dma containing LNPs.

Figure 6:
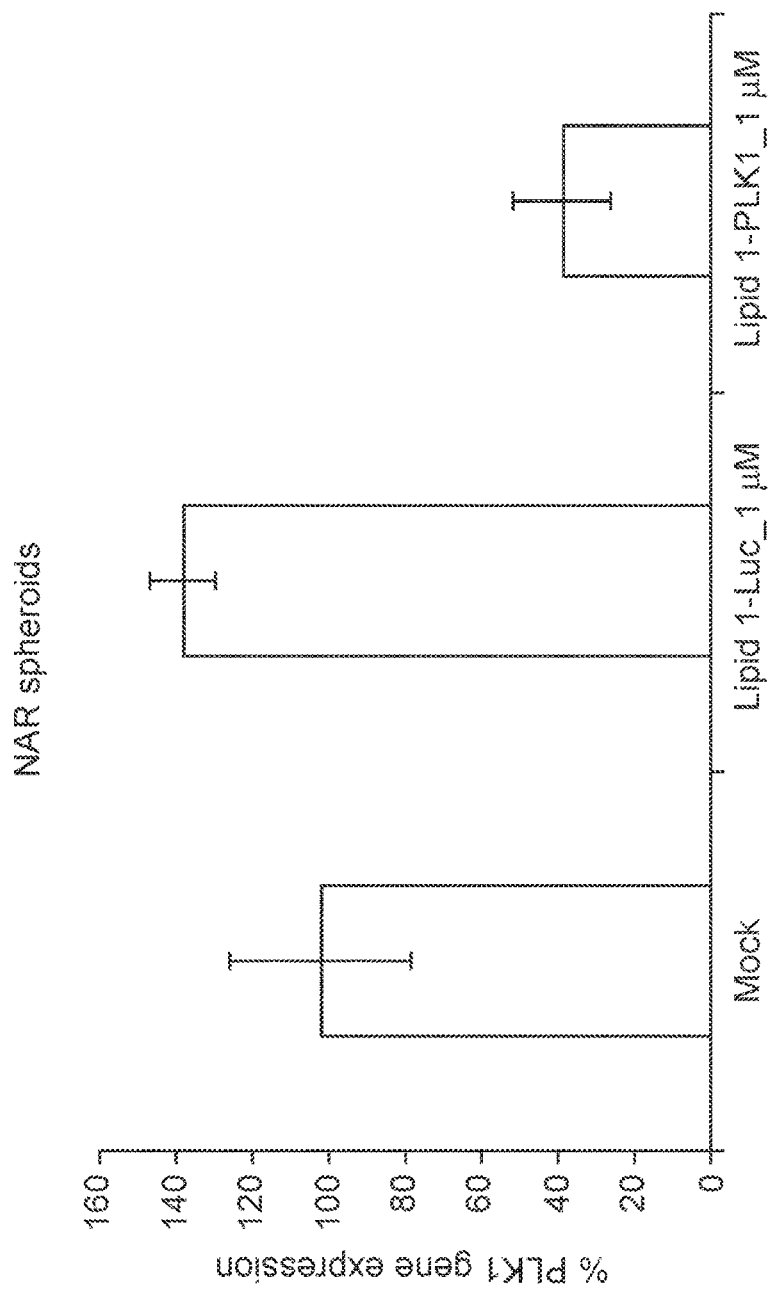
FIG. 6: Spheroids of drug resistant human ovarian carcinoma cells (NAR) were treated with either LNP-siPLK-1 or LNP-siLuc nanoparticles for 72 hr and PLK-1 expression was measured by qPCR.

Spheroids of drug resistant human ovarian carcinoma cells (NAR) were treated with LNPs composed of lipid1 and with either siPLK-1 or siLuc s for 72 hr and PLK-1 expression was measured by qPCR. Spheroids are 3D cultures of tumor cells mimicking in vivo tumors. As shown in FIG. 6, lipid1 containing siPLK1-LNPs significantly downregulating PLK1 gene compared to siLUC-LNPs indicating the efficiency of lipid1 to deliver siRNA in to NAR spheroids.

Figure 7:
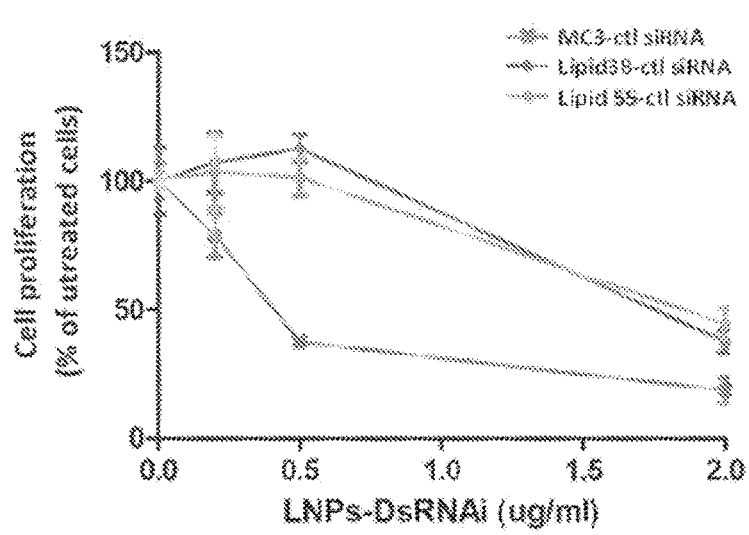
FIG. 7: Human colon carcinoma cells (HCT116) were incubated with LNPs (comprising MC3, Lipids 38 or Lipid 55) with ctl siRNA for 72 hrs. Cell viability was measured by XTT assay.

Human colon carcinoma cells (HCT116) were incubated with LNPs with ctl siRNA (see methods) for 72 hrs. The cell viability was measured by XTT assay. Toxicity of LNPs composed of either lipid 38 or lipid 55 is compared with gold standard LNPs composed of Dlin-MC3-DMA. As shown in FIG. 7, LNPs composed of either lipid 38 or lipid 55 are less toxic than LNPs composed of Dlin-MC3-DMA in a dose dependent manner.

In Vitro Gene Silencing Effects of Lipids 38&55.

Figure 8:
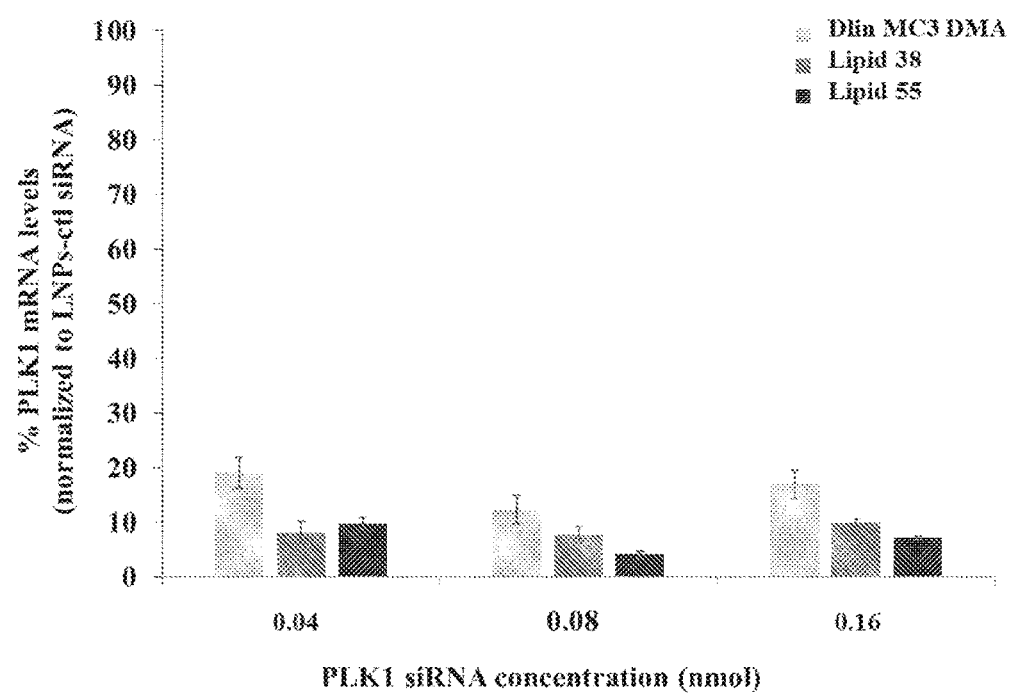
FIG. 8: In vitro gene silencing effects of Lipids 38 or 55. Human multiple myeloma suspension cells (U266) were incubated with LNPs containing siPLK1 at different concentrations for 48 hrs. PLK1 expression was measured by qPCR. PLK1-mRNA levels were normalized to LNPs-ctl siRNA treated cells.

Human multiple myeloma suspension cells (U266) were incubated with LNPs containing siPLK1 at different concentrations for 48 hrs. PLK1 expression was measured by qPCR. PLK1-mRNA levels were normalized to LNPs-ctl siRNA treated cells. As shown in FIG. 8, PLK1 gene was efficiently down regulate in cells treated with siPLK1-LNPs composed of either lipid38 or lipid 55 and comparable to Dlin-MC3-DMA LNPs.

Figure 9:
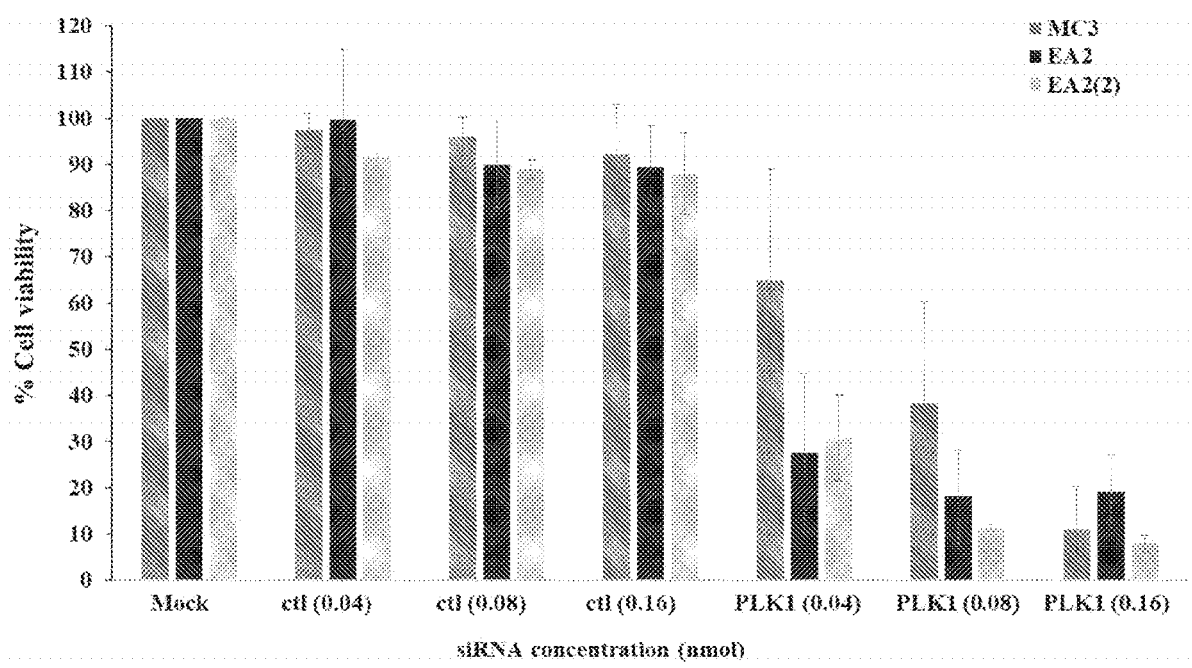
FIG. 9: Effect of PLK1 silencing on cell viability. Human multiple myeloma suspension cells (U266) were incubated with LNPs comprising cationic lipids 38 or 55 and siPLK1 or ctl-siRNA at different concentrations for 48 hrs. Cell viability induced by PLK1 down regulation was measured by XTT assay.

Effect of PLK1 Downregulation on Multiple Myeloma Cell Survival:

Human multiple myeloma suspension cells (U266) were incubated with siPLK1-LNPs or siCtl-LNPs composed of either lipid 38 or 55 at different concentrations for 48 hrs. Cell viability affected by PLK1 down regulation was measured by XTT assay. As shown in FIG. 9, siPLK1-LNPs composed of either lipid 38 or lipid 55 has more effect on cell viability compared to Dlin-MC3-DMA LNPs due to efficient downregulation of PLK1 gene, whereas siCtl-LNPs has no effect on the cell viability indicating the safe use of new lipids.

Figure 10:
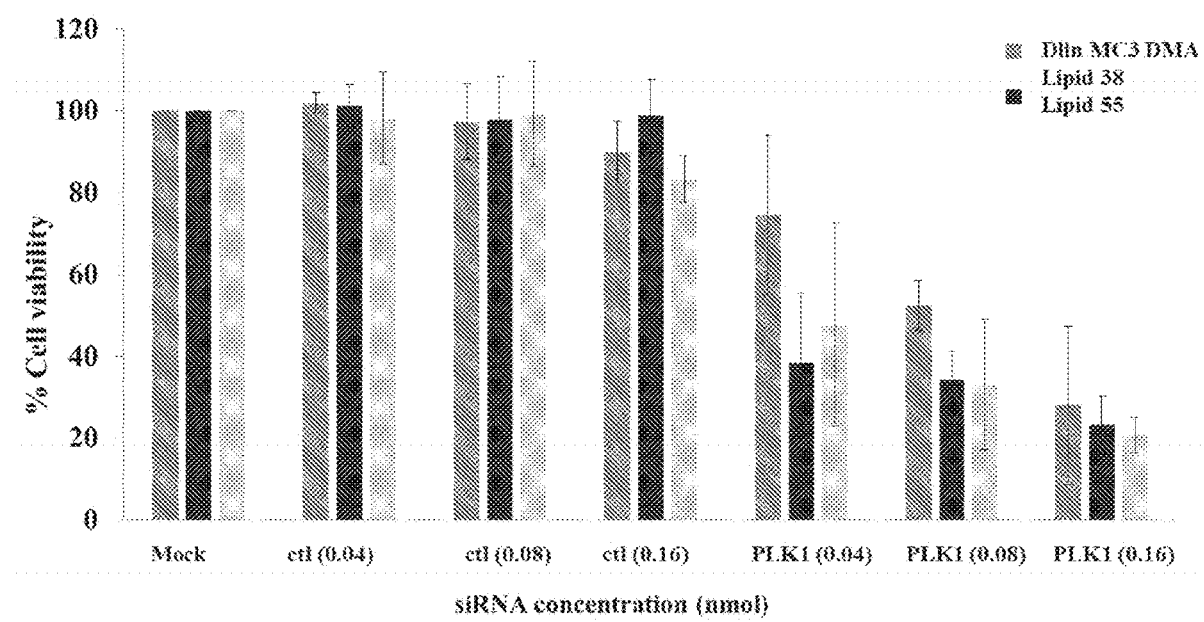
FIG. 10 shows cell proliferation (% of untreated cells) vs. concentration of siPLK1.

Effect of PLK1 Silencing on B-Cell Lymphoma Viability:

Human B-cell lymphoma suspension cells (RPMI-8226) were incubated with siPLK1-LNPs or siCtl-LNPs composed of either lipid 38 or 55 at different concentrations for 48 hrs. Cell viability affected by PLK1 down regulation was measured by XTT assay. As shown in FIG. 10, siPLK1-LNPs composed of either lipid 38 or lipid 55 exhibiting a dose dependent effect on B-cell lymphoma cancer cell viability due to efficient downregulation of PLK1 gene, whereas siCtl-LNPs has no effect on the cell viability.

Figure 11:
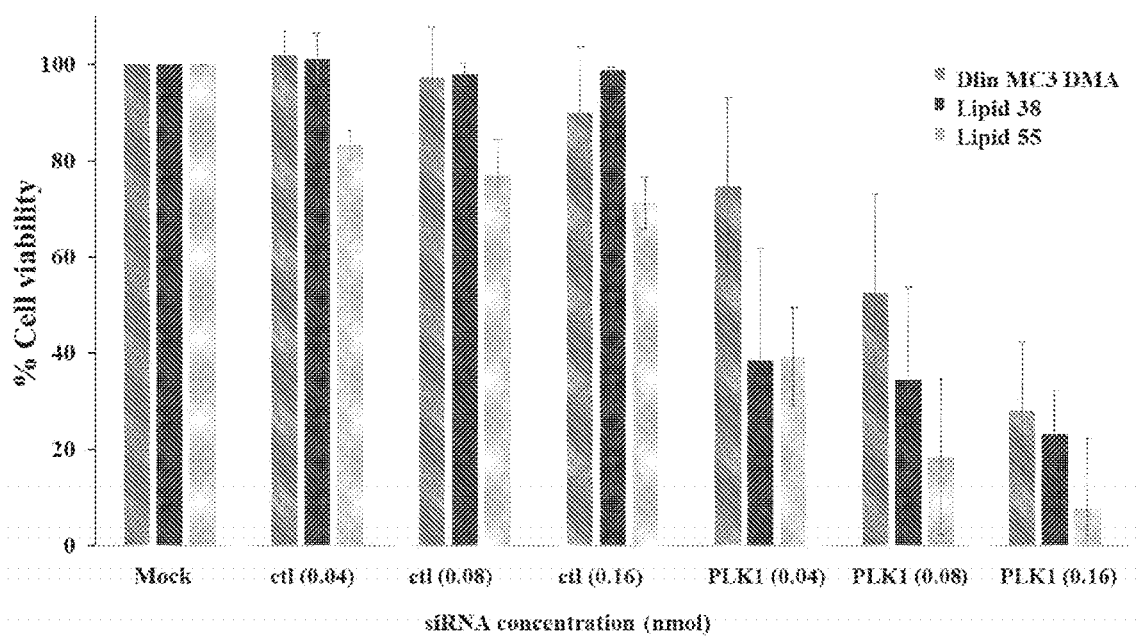
FIG. 11: Effect of PLK1 silencing on cell viability. Human multiple myeloma suspension cells (MM1) were incubated with LNPs comprising cationic lipids 38 or 55 and siPLK1 or ctl-siRNA at different concentrations for 48 hrs. Cell viability induced by PLK1 down regulation was measured by XTT assay.

Effect of PLK1 Silencing on Cell Viability:

Human multiple myeloma suspension cells (MM1) were incubated with siPLK1-LNPs or siCtl-LNPs composed of either lipid 38 or 55 at different concentrations for 48 hrs. Cell viability affected by PLK1 down regulation was measured by XTT assay. As shown in FIG. 11, siPLK1-LNPs composed of either lipid 38 or lipid 55 exhibiting a dose dependent effect on multiple myeloma cancer cell viability due to PLK1 downregulation, whereas siCtl-LNPs has no effect on the cell viability.

Figure 12:
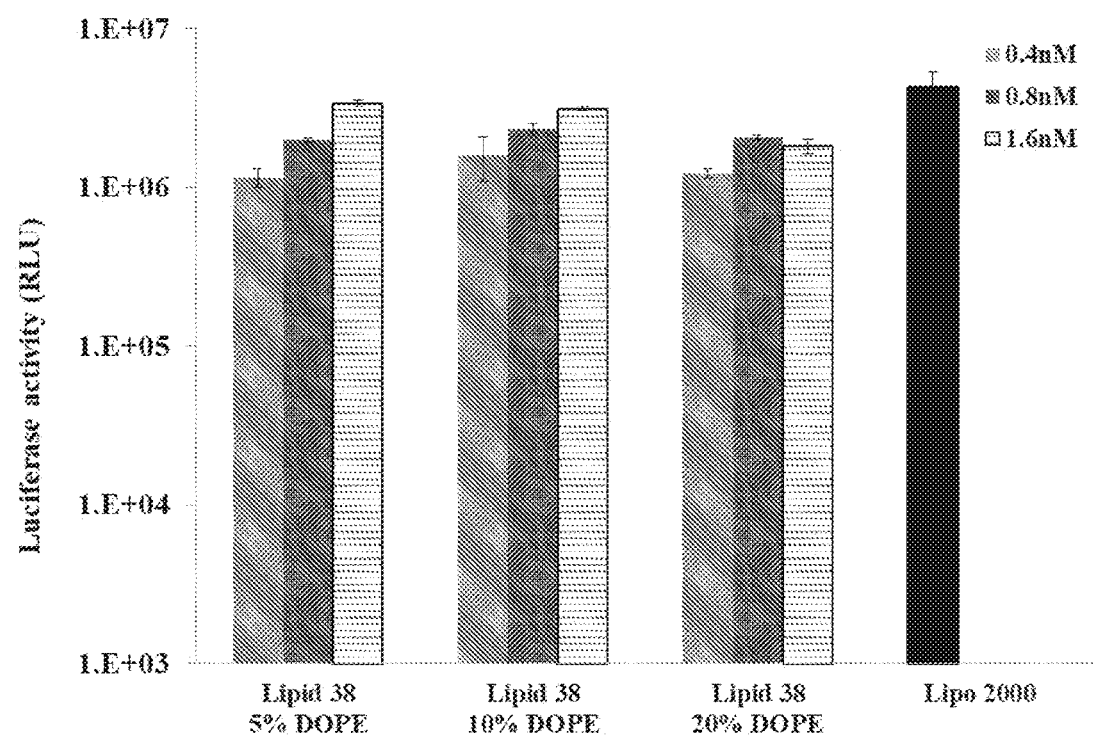
FIG. 12: In vitro expression of pDNA. Human colon carcinoma cells (HCT 116) were incubated with LNPs-LUC pDNA at different concentrations for 48 hrs. Luciferase expression was measured by luminometer. Lipofectamine 2000 (Lipo 2000) was used as positive control. LNPs were formulated with lipid 38 and different amounts of DOPE, along with other co-lipids Chol, and PEG-DMG.

In Vitro Expression of pDNA:

Human colon carcinoma cells (HCT 116) were incubated with LNPs-LUC pDNA at different concentrations for 48 hrs. Luciferase expression was measured by luminometer. Lipofectamine 2000 (Lipo 2000) was used as positive control. LNPs were composed of lipid 38 and different amounts of co-lipid DOPE, along with other co-lipids such as Chol, PEG-DMG. As shown in FIG. 12, LNPs-pDNA composed of lipid 38 efficiently delivering pDNA to the nucleus. The amount of luciferase expression was similar to positive control lipo 2000.

Figure 13:
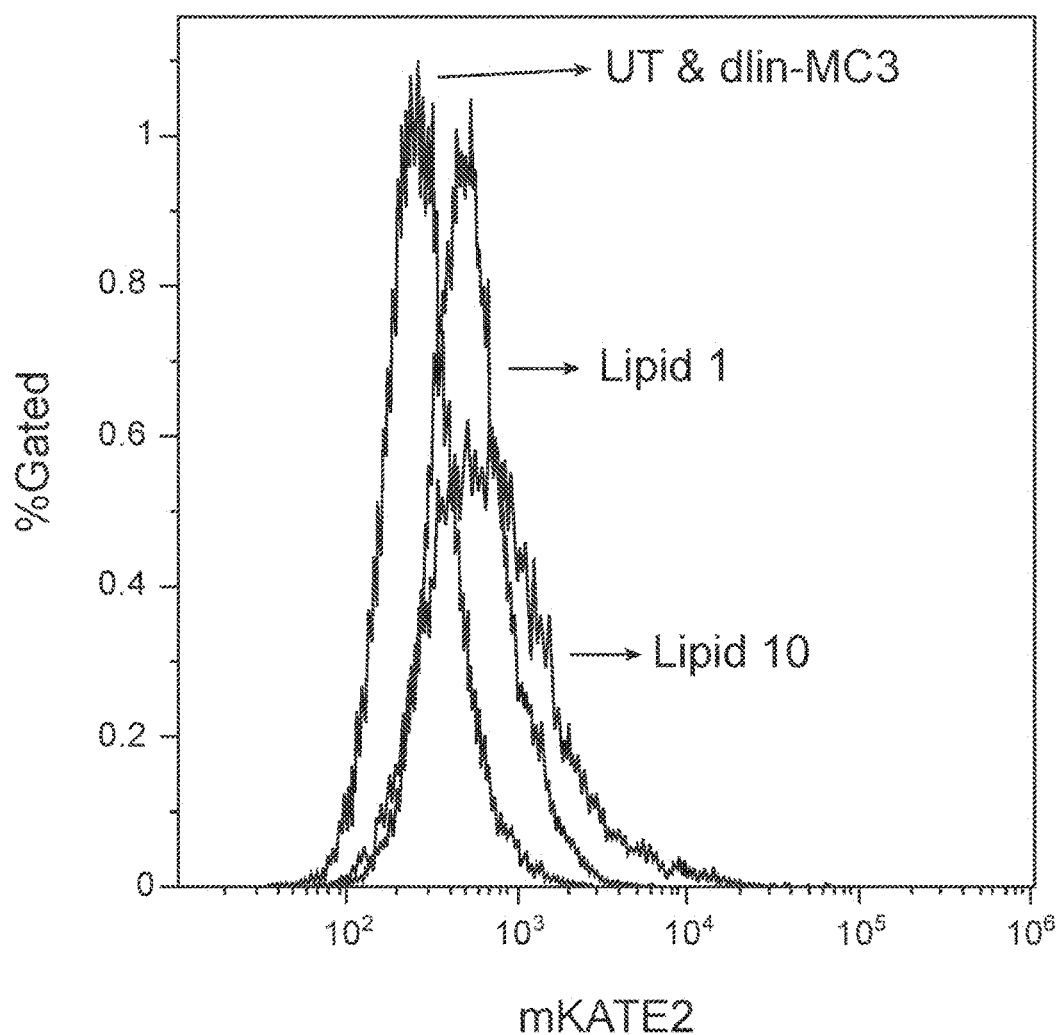
FIG. 13: HEK 293 cells were treated with LNP-DNA nanoparticles (10:1 N/P ratio, 0.6 nM DNA) for 72 hr and mKATE expression was analyzed by flow cytometry.

In vitro expression of pDNA in HEK 293 cells: HEK cells were treated with LNPs composed of either lipid1 or lipid 10 encapsulated with mKATE-pDNA at the concentration of 0.6 nM pDNA. After 72 hr, mKATE expression was analyzed by flow cytometry. As shown in FIG. 13, LNPs composed of either lipid1 or lipid 10 efficiently delivering the pDNA to the nucleus and mKATE expression was observed, whereas Dlin-MC3-DMA LNPs did not show any effect on mKATE expression.

Figure 14:
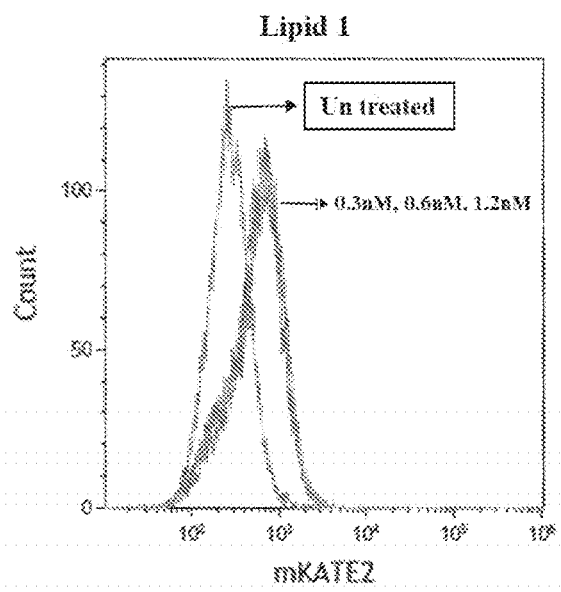
FIG. 14: HEK 293 cells were treated with LNP-DNA nanoparticles (10:1 N/P ratio) at different DNA for 72 hr and mKATE expression was analyzed by flow cytometry.
Figure 14:
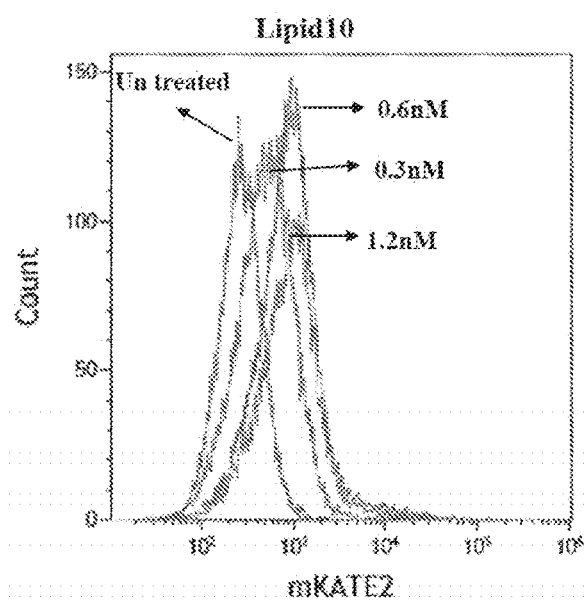

Dose dependent expression of pDNA in HEK 293 cells: HEK cells were treated with LNPs composed of either lipid1 or lipid 10 encapsulated with mKATE-pDNA at different amount pDNA. After 72 hr, mKATE expression was analyzed by flow cytometry. As shown in FIG. 14A, LNPs-pDNA composed of lipid 1 did not show any dose dependent expression, but as shown in FIG. 14B, lipid 10 containing LNPs exhibiting a dose dependent expression of mKATE.

Figure 15:
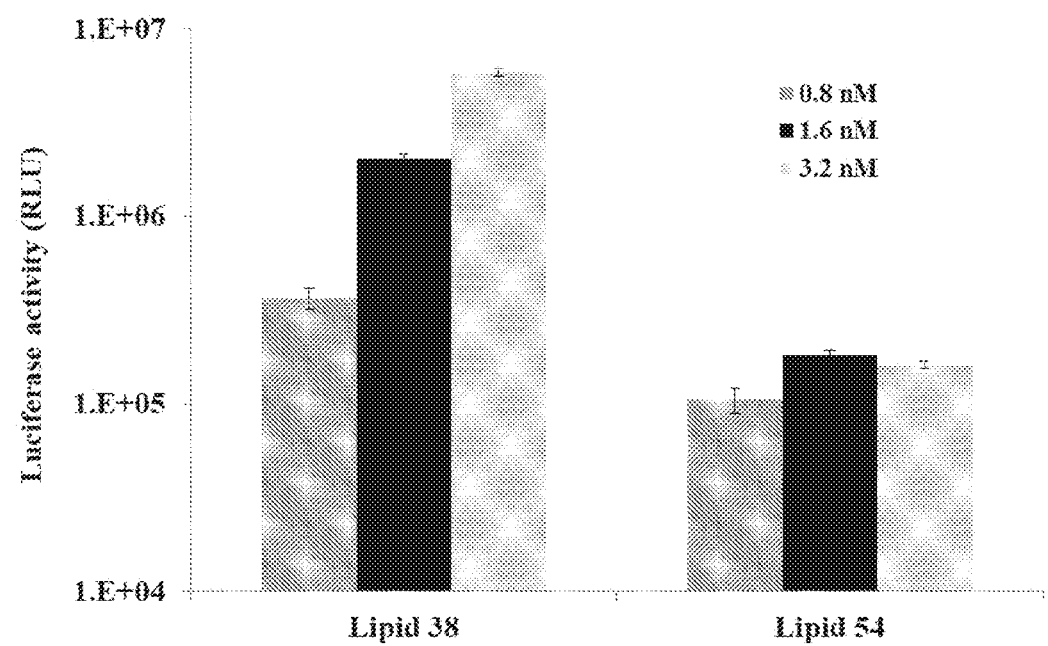
FIG. 15: In vitro delivery of mRNA. Hard to transfect murine macrophage cells (RAW 264.7) were treated with LNPs containing cationic lipids 38 or 54 and luciferase mRNA for 18 hrs at different mRNA concentrations. Luciferase expression was measured by luminometer.

In Vitro Delivery of mRNA:

Hard to transfect murine macrophage cells (RAW 264.7) were treated with LNPs composed of either Lipid38 or Lipid 54 and formulated with luciferase mRNA at different amounts of mRNA. After 18 hrs luciferase expression was measured by luminometer. As shown in FIG. 15, luciferase expression was observed in cells treated with lipid 38-LNPs efficiently compared to lipid 54-LNPs, further a dose dependent expression was observed in lipid 38 containing LNPs.

Figure 16A:
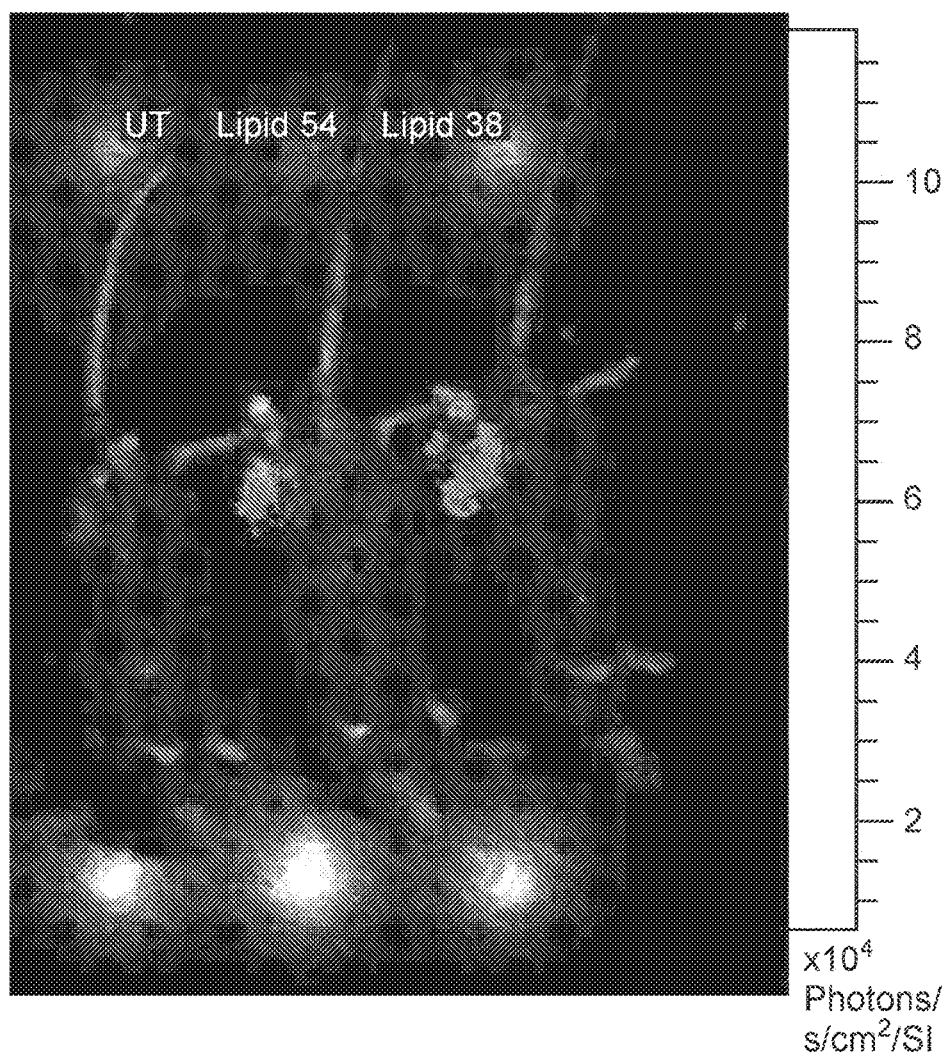
FIG. 16: In vivo delivery of mRNA. LNPs containing cationic lipids 38 or 54 luciferase mRNA was administered intramuscularly to C57BL6/j mice at 1 mg/kg body weight. Luciferase expression was measured by bioluminescence imaging system Biospace: (A) after 8 hrs of i.m. administration; and (B) after 24 hrs.
Figure 16B:
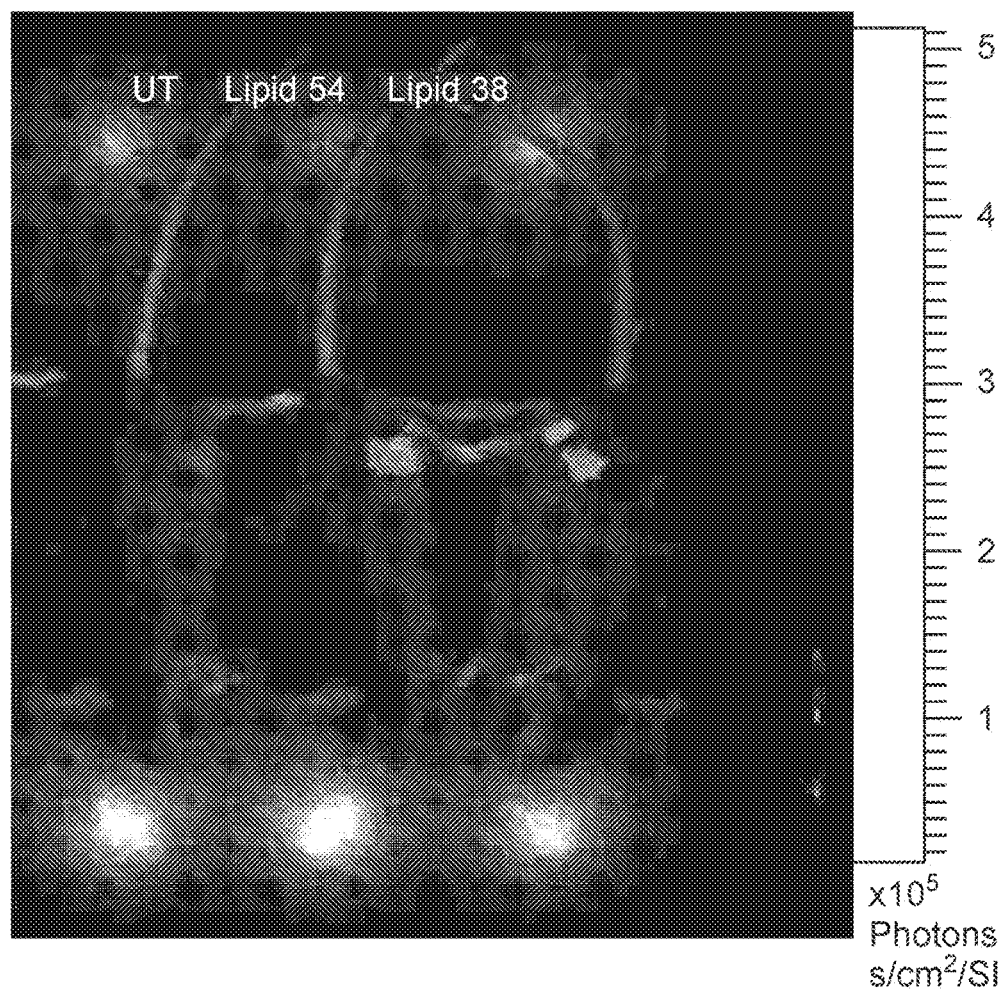

In Vivo Delivery of mRNA to Muscle Cells:

LNPs composed of either lipid 54 or lipid 38 formulated with luciferase mRNA were administered intramuscularly in to C57BL6/j mice at 1 mg/kg body weight. Luciferase expression was measured by bioluminescence imaging system Biospace: (a) after 8 hrs of i.m. administration; and (b) after 24 hrs. As shown in FIG. 16, significant amounts of luciferase were observed after 8 hrs of administration for both LNPs composed of either lipid 38 or lipid 54. The expression was still high 24 hrs after the administration of LNPs indicating the efficiency of these lipids in delivering mRNA in vivo.

Figure 17:
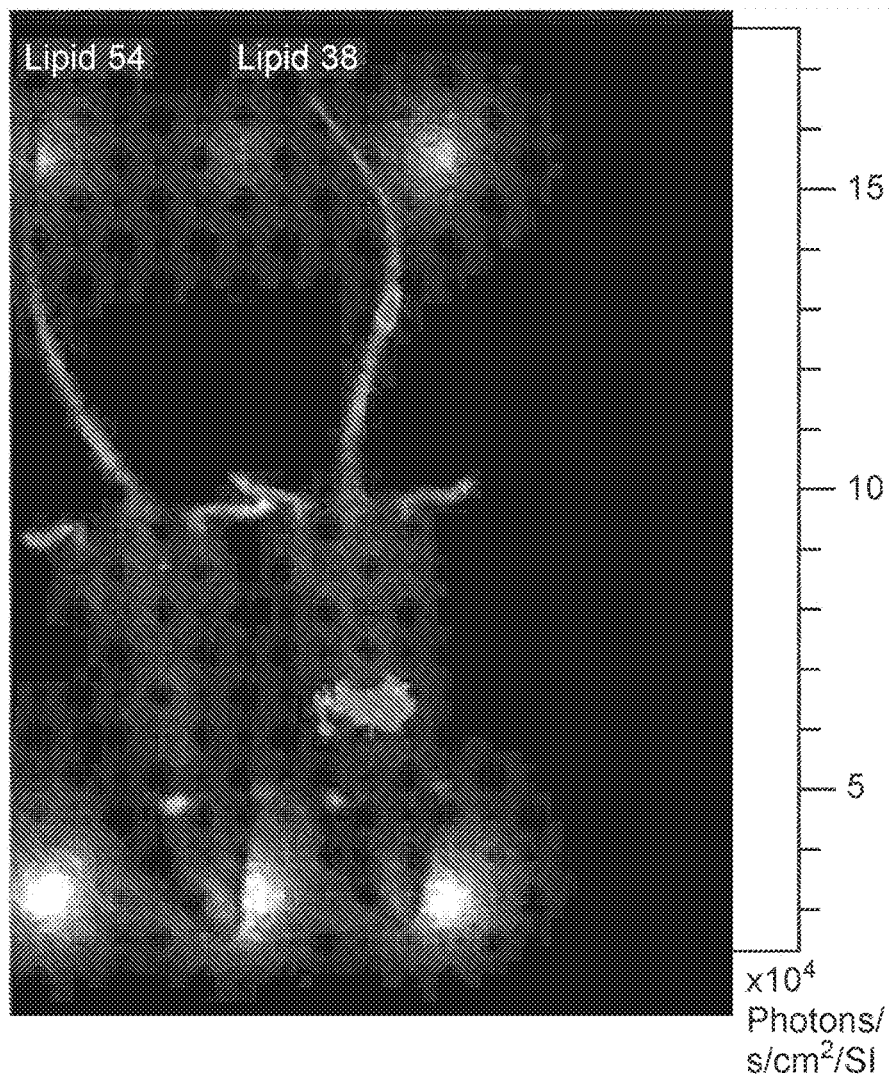
FIG. 17: LNPs composed of either lipid 54 or lipid 38 formulated with luciferase mRNA were administered intravenously into C57BL6/j mice at 1 mg/kg body weight. After 8 hrs, luciferase expression was measured by bioluminescence imaging system Biospace.

In Vivo Delivery of mRNA to Liver:

LNPs composed of either lipid 54 or lipid 38 formulated with luciferase mRNA were administered intravenously into C57BL6/j mice at 1 mg/kg body weight. After 8 hrs, luciferase expression was measured by bioluminescence imaging system Biospace. As shown in FIG. 17, mice treated with LNPs composed of lipid 38 and mRNA showing significant amount of luciferase in mouse liver compared to LNPs composed of lipid 54.

Figure 18:
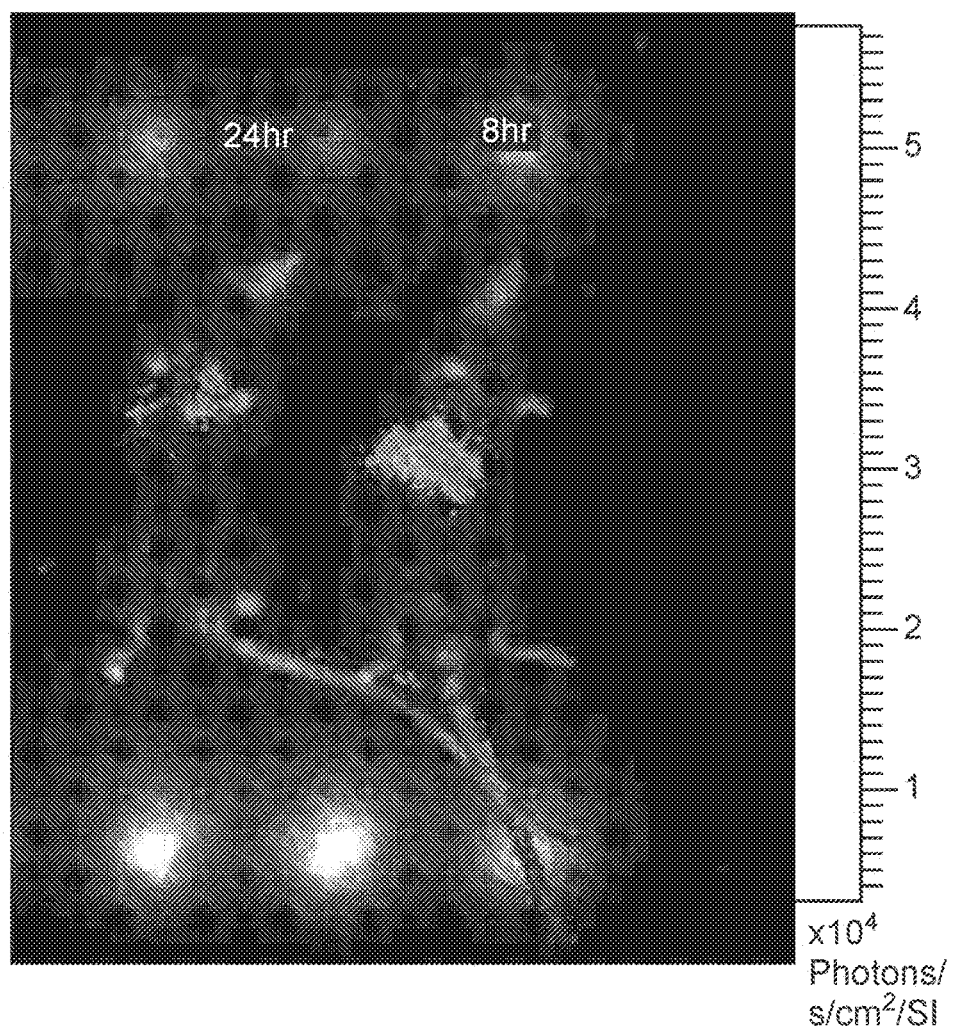
FIG. 18: In vivo delivery of mRNA to liver. LNPs composed of lipid 38 formulated with luciferase mRNA were administered intravenously into C57BL6/j mice at 1 mg/kg body weight. After 8 hrs and 24 hrs of administration, luciferase expression was measured by bioluminescence imaging system Biospace.

In Vivo Delivery of mRNA to Liver:

LNPs composed of lipid 38 formulated with luciferase mRNA were administered intravenously into C57BL6/j mice at 1 mg/kg body weight. After 8 hrs and 24 hrs of administration, luciferase expression was measured by bioluminescence imaging system Biospace. As shown in FIG. 18, significant amount of luciferase expression was observed in liver. Moreover the luciferase expression was high after 8 hrs compared to after 24 hrs.

Figure 19:
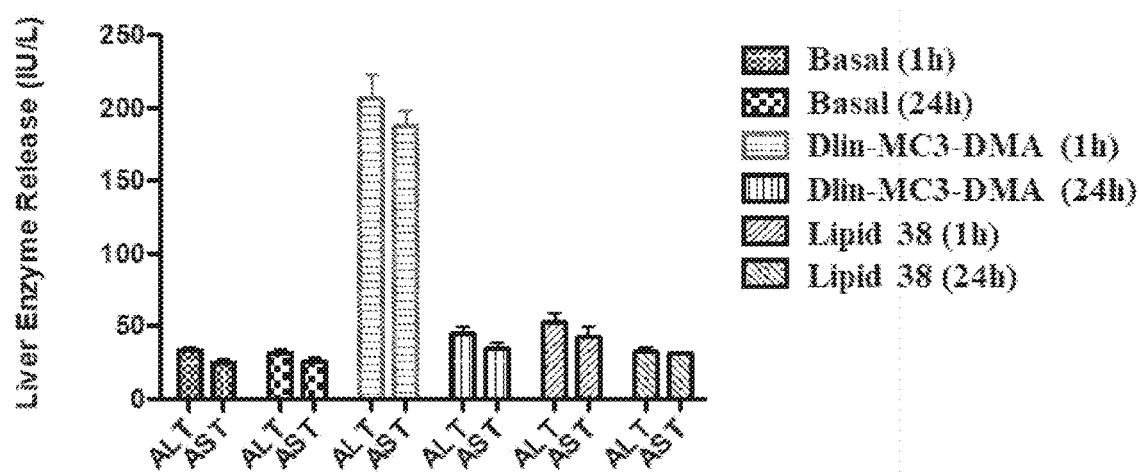
FIG. 19: No liver toxicity in Non-human primate compared with MC3. Cynomolgus monkeys (n=2 per group, males) received a single i.v. administration (1 ml/kg) of (0.5 mg/kg) of MC3 particles with siNC5 and lipid 38-based particles with siNC5 (0.5 mg/Kg). At 1 and 24 h post administration serum was collected at and analyzed for ALT, AST. Each data point is an average of 2 animals±SEM.

FIG. 19: demonstrates that there is no liver toxicity in Non-human primate compared with MC3. Cynomolgus monkeys (n=2 per group, males) received a single I.v. administration (1 ml/kg) of (0.5 mg/kg) of MC3 particles with siNC5 and lipid 38-based particles with siNC5 (0.5 mg/Kg). At 1 and 24 h post administration serum was collected at and analyzed for ALT, AST (by Roch Cobra Auto analyzer). Each data point is an average of 2 animals±SEM.

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

The Sequence Listing in ASCII text file format of 4,031 bytes in size, created on Aug. 3, 2023, with the file name "2023-08-07SequenceListing_PEER12_ST25," filed in the US. Patent and Trademark Office on even date herewith, is hereby incorporated herein by reference.

What is claimed is:

1. A cationic lipid which is represented by the structure of formula (I), formula (II) or formula (IIIA), or salts, hydrates, solvates, polymorphs, optical isomers, geometrical isomers, enantiomers, diastereomers, and mixtures thereof, wherein the structure of formula (I), formula (II) and formula (IIIA) is represented below:

Formula (I):

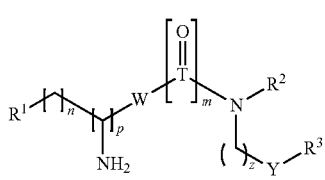

wherein
Y is O or NH;
T is C or S;
W is a bond or NH;
$R^1$ is selected from the group consisting of:
 (a) $NR^4R^5$ wherein $R^4$ and $R^5$ are each independently a $C_1$-$C_4$ alkyl; or $R^4$ and $R^5$ together with the nitrogen to which they are attached form a 5 or 6 membered heterocyclic or heteroaromatic ring, optionally containing one or more additional heteroatoms selected from the group consisting of O, N and S; or $NR^4R^5$ represent a guanidine group (—NHC(=NH)NH$_2$);
 (b) the side chain of histidine or arginine; and
 (c) a 5 or 6 membered heterocyclic or heteroaromatic ring containing one or more heteroatoms selected from the group consisting of O, N and S;

$R^2$ and $R^3$ are selected from the group consisting of:
 (a) $C_{10}$-$C_{22}$ alkyl;
 (b) $C_{10}$-$C_{22}$ alkenyl;
 (c) $C_{10}$-$C_{22}$ alkynyl;
 (d) $C_4$-$C_{10}$ alkylene-Z— $C_4$-$C_{22}$ alkyl; and
 (e) $C_4$-$C_{10}$ alkylene-Z— $C_4$-$C_{22}$ alkenyl;

Z is —O—C(=O)—, —C(=O)—O— or —O—;
n is 0, 1, 2, 3, 4, 5 or 6;
m is 0 or 1;
p is 0 or 1; and
z is 0 or 2;

Formula (II):

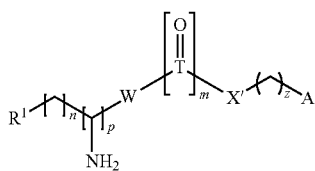

wherein
A is

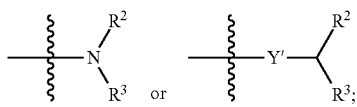

X' is O or NH;
Y' is O or NH;
provided that when A is

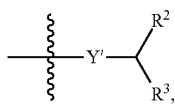

X' and Y' cannot both be O;
T is C or S;
W is a bond, O, NH or S;
$R^1$ is selected from the group consisting of:
(a) $NR^4R^5$ wherein $R^4$ and $R^5$ are each independently a $C_1$-$C_4$ alkyl; or $R^4$ and $R^5$ together with the nitrogen to which they are attached form a 5 or 6 membered heterocyclic or heteroaromatic ring, optionally containing one or more additional heteroatoms selected from the group consisting of O, N and S; or $NR^4R^5$ represent a guanidine group (—NHC(=NH)NH$_2$);
(b) the side chain of histidine or arginine; and
(c) a 5 or 6 membered heterocyclic or heteroaromatic ring containing one or more heteroatoms selected from the group consisting of O, N and S;
$R^2$ and $R^3$ are selected from the group consisting of:
(a) $C_{10}$-$C_{22}$ alkyl;
(b) $C_{12}$-$C_{22}$ alkenyl;
(c) $C_{10}$-$C_{22}$ alkynyl;
(d) $C_4$-$C_{10}$ alkylene-Z—$C_4$-$C_{22}$ alkyl; and
(e) $C_4$-$C_{10}$ alkylene-Z—$C_4$-$C_{22}$ alkenyl;
Z is —O—C(=O)—, —C(=O)—O— or —O—;
n is 0, 1, 2, 3, 4, 5 or 6;
m is 0 or 1;
p is 0 or 1; and
z is 0 or 2;
Formula (IIIA):

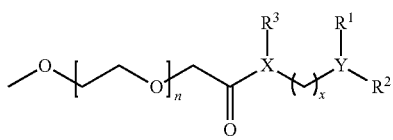

wherein
X and Y are each independently O, N or NH, wherein X and Y cannot both be O;
each of $R^1$, $R^2$ and $R^3$ is independently absent or a $C_{10}$-$C_{22}$ alkyl, a $C_{10}$-$C_{22}$ alkenyl or a $C_{10}$-$C_{22}$ alkynyl, wherein the alkyl group is unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl;
n is an integer between 1 and 30; and
x is 0 or 2.

2. The cationic lipid according to claim 1, which is represented by the structure of formula (I).

3. The cationic lipid according to claim 2, wherein T is C or wherein $R^1$ is $NR^4R^5$.

4. The cationic lipid according to claim 2, wherein p is 0, W is a bond and T is C, and the compound is represented by the structure of formula (Ia):

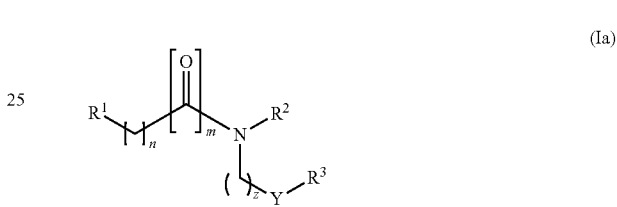

wherein $R^1$, $R^2$, $R^3$, Y, m, n and z are as defined for formula (I).

5. The cationic lipid according to claim 4, wherein $R^1$ is $NR^4R^5$, and the compound is represented by the structure of formula (Ia-1):

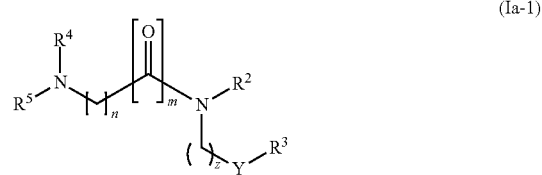

wherein $R^2$, $R^3$, $R^4$, $R^5$, Y, m, n and z are as defined for formula (I).

6. The cationic lipid according to claim 1, which is represented by the structure of formula (II).

7. The cationic lipid according to claim 6, which is represented by the structure of formula (IIa):

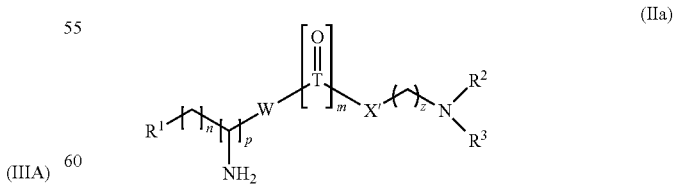

wherein $R^1$, $R^2$, $R^3$, X', T, W, n, m, p and z are as defined for formula (II).

8. The cationic lipid according to claim 7, wherein p is 0, W is a bond and T is C, and the compound is represented by the structure of formula (IIa-1):

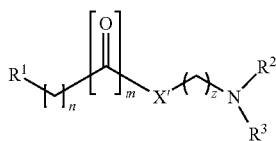
(IIa-1)

wherein $R^1$, $R^2$, $R^3$, X', n, m and z are as defined for formula (II).

9. The cationic lipid according to claim 8, wherein $R^1$ is $NR^4R^5$, and the compound is represented by the structure of formula (IIa-2):

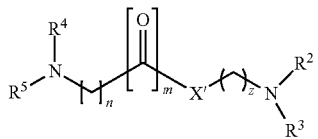
(IIa-2)

wherein $R^2$, $R^3$, $R^4$, $R^5$, X', n, m and z are as defined for formula (II).

10. The cationic lipid according to claim 7, wherein p is 1, m is 1, W is a bond and T is C, and the compound is represented by the structure of formula (IIa-3):

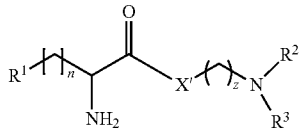
(IIa-3)

wherein $R^1$ is the side chain of histidine or arginine and $R^2$, $R^3$, X', n and z are as defined for formula (II).

11. The cationic lipid according to claim 7, wherein p is 0, $R^1$ is $NR^4R^5$, W is a bond, m is 0 and X' is O, and the compound is represented by the structure of formula (IIa-4):

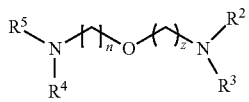
(IIa-4)

wherein $R^2$, $R^3$, $R^4$, $R^5$, n, and z are as defined for formula (II).

12. The cationic lipid according to claim 6, which is represented by the structure of formula (IIb):

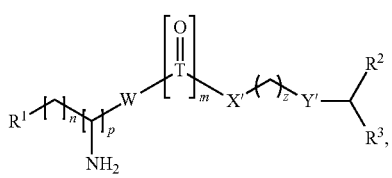
(IIb)

wherein $R^1$, $R^2$, $R^3$, T, W, X', Y' n, m, p and z are as defined for formula (II), provided that when m is 1, Y' is NH.

13. The cationic lipid according to claim 12, wherein p is 0, W is a bond, T is C, and $R^1$ is $NR^4R^5$, and the compound is represented by the structure of formula (IIb-1):

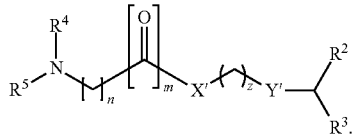
(IIb-1)

14. The cationic lipid according to claim 1, which is selected from the group consisting of:
2-(1,2-di((9Z,12Z)-octadeca-9,12-dien-1-yl)hydrazinyl)-N,N-dimethylethan-1-amine;
4-(1,2-di((9Z,12Z)-octadeca-9,12-dien-1-yl)hydrazinyl)-N,N-dimethylbutan-1-amine;
1-(4-(1,2-di((9Z,12Z)-octadeca-9,12-dien-1-yl)hydrazinyl)butyl)pyrrolidine;
N,N-dimethyl-4-(((9Z,12Z)-octadeca-9,12-dien-1-yl)(((9Z,12Z)-octadeca-9,12-dien-1-yl)oxy)amino)butan-1-amine;
4-(dimethylamino)-N'—((Z)-octadec-9-en-1-yl)-N-((9Z,12Z)-octadeca-9,12-dien-1-yl)butanehydrazide;
4-(dimethylamino)-N-((9Z,12Z)-octadeca-9,12-dien-1-yl)-N-(((9Z,12Z)-octadeca-9,12-dien-1-yl)oxy)butanamide;
N,N-dimethyl-2-(2-((Z)-octadec-9-en-1-yl)-1-((9Z,12Z)-octadeca-9,12-dien-1-yl)hydrazinyl)ethan-1-amine;
N,N-dimethyl-2-(1-((9Z,12Z)-octadeca-9,12-dien-1-yl)-2-octadecylhydrazinyl)ethan-1-amine;
(1-(2-(dimethylamino)ethyl)hydrazine-1,2-diyl)bis(hexane-6,1-diyl) bis(2-hexyldecanoate);
(1-(2-(dimethylamino)ethyl)hydrazine-1,2-diyl)bis(nonane-9,1-diyl) bis(2-hexyl decanoate);
di(tridecan-7-yl) 10,10'-(1-(2-(dimethylamino)ethyl)hydrazine-1,2-diyl)bis(decanoate);
4-(2-(2,2-di((9Z,12Z)-octadeca-9,12-dien-1-yl)hydrazinyl)ethyl)-1H-imidazole;
(1-(2-(dimethylamino)ethyl)hydrazine-1,2-diyl)bis(octane-8,1-diyl) (4Z,4'Z)-bis(2-hexyldec-4-enoate); and
(1-(2-(dimethylamino)ethyl)hydrazine-1,2-diyl)bis(octane-8,1-diyl) (3Z,3'Z)-bis(non-3-enoate).

15. The cationic lipid according to claim 1, which is represented by the structure of formula (IIIA), wherein the each of $R^1$ and $R^2$ is independently absent or a $C_{10}$-$C_{22}$ alkyl, a $C_{10}$-$C_{22}$ alkenyl or a $C_{10}$-$C_{22}$ alkynyl, wherein the alkyl group is unsubstituted or substituted by one or more groups selected from halogen, hydroxy, alkoxy carbonyl, amido, alkylamido, dialkylamido, nitro, amino, alkylamino, dialkylamino, thio and thioalkyl.

16. The cationic lipid according to claim 15, which is selected from the group consisting of:

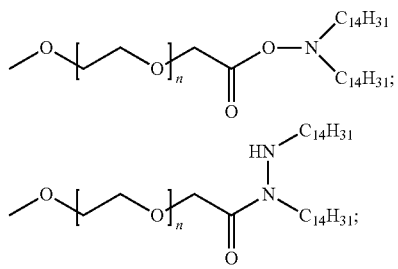

-continued

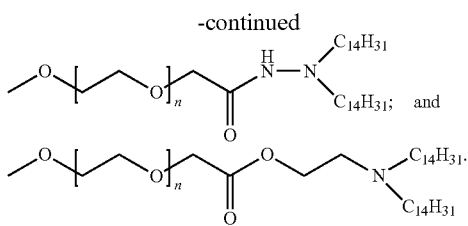

17. A composition comprising a cationic lipid according to claim 1, optionally further comprising at least one additional neutral or PEG-modified lipid.

18. A method of gene silencing, comprising the step of contacting a cell with a composition according to claim 17.

19. A method of treating a leukocyte associated condition, the method comprising the step of administering to a subject in need thereof a composition according claim 17, with the proviso that treating is not for preventing the appearance of clinical symptoms of a leukocyte associated disease or condition or for preventing or barring a subject from acquiring a disorder or disease or condition.

20. A composition according to claim 17, further comprising a nucleic acid selected from the group consisting of small interfering RNA (siRNA), antisense oligo nucleotides, micro RNA (miRNA), ribozymes, pDNA, CRISPR mRNA, gRNA and immune stimulating nucleic acids.

21. A composition according to claim 17, further comprising messenger RNA (mRNA).

22. A method of expressing a protein encoded by mRNA, comprising the step of administering a composition according to claim 21.

23. A cationic lipid which is represented by the structure of formula (IIIA), or salts, hydrates, solvates, polymorphs, optical isomers, geometrical isomers, enantiomers, diastereomers, and mixtures thereof,

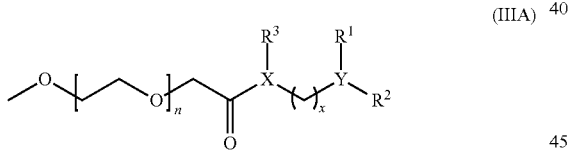

wherein
X and Y are each independently O, N or NH, wherein X and Y cannot both be O;
each of $R^1$, $R^2$ and $R^3$ is independently absent or a $C_{10}$-$C_{22}$ alkyl, a $C_{10}$-$C_{22}$ alkenyl or a $C_{10}$-$C_{22}$ alkynyl, wherein the alkyl group is unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl;
n is an integer between 1 and 30; and
x is 0 or 2.

24. The cationic lipid according to claim 1, which is selected from the group consisting of:
4-((di((9Z,12Z)-octadeca-9,12-dien-1-yl)amino)oxy)-N,N-dimethylbutan-1-amine;
1-(4-(2,2-di((9Z,12Z)-octadeca-9,12-dien-1-yl)hydrazinyl)butyl)pyrrolidine;
4-(((((6Z,9Z,28Z,31Z)-heptatriaconta-6,9,28,31-tetraen-19-yl)amino)oxy)-N,N-dimethylbutan-1-amine;
2-((di((9Z,12Z)-octadeca-9,12-dien-1-yl)amino)oxy)-N,N-dimethyl-2-oxoethan-1-amine;
4-(dimethylamino)-N',N'-di((9Z,12Z)-octadeca-9,12-dien-1-yl)butanehydrazide;
(S)-2-amino-6-(dimethylamino)-N',N'-di((9Z,12Z)-octadeca-9,12-dien-1-yl)hexanehydrazide;
4-(2,2-di((9Z,12Z)-octadeca-9,12-dien-1-yl)hydrazinyl)-N,N-dimethylbutan-1-amine;
1-((S)-4-amino-5-(2,2-di((9Z,12Z)-octadeca-9,12-dien-1-yl)hydrazinyl)-5-oxopentyl)guanidine;
4-((di((9Z,12Z)-octadeca-9,12-dien-1-yl)amino)oxy)-N,N-dimethyl-4-oxobutan-1-amine;
2-(2,2-di((9Z,12Z)-octadeca-9,12-dien-1-yl)hydrazinyl)-N,N-dimethylethan-1-amine;
N',N'-di((9Z,12Z)-octadeca-9,12-dien-1-yl)-4-(pyrrolidin-1-yl)butanehydrazide;
(S)-2-amino-3-(1H-imidazol-4-yl)-N',N'-di((9Z,12Z)-octadeca-9,12-dien-1-yl)propanehydrazide;
4-(4-methylpiperazin-1-yl)-N',N'-di((9Z,12Z)-octadeca-9,12-dien-1-yl)butanehydrazide;
O-(4-(4-methylpiperazin-1-yl)butanoyl)-N,N-di((9Z,12Z)-octadeca-9,12-dien-1-yl)hydroxylamine;
(2-(4-(dimethylamino)butanoyl)hydrazine-1,1-diyl)bis(hexane-6,1-diyl) bis(2-hexyldecanoate);
(2-(4-(dimethylamino)butyl)hydrazine-1,1-diyl)bis(hexane-6,1-diyl) bis(2-hexyl decanoate);
(2-(4-(dimethylamino)butyl)hydrazine-1,1-diyl)bis(nonane-9,1-diyl) bis(2-hexyl decanoate);
((4-(dimethylamino)butoxy)azanediyl)bis(hexane-6,1-diyl) bis(2-hexyldecanoate);
((4-(dimethylamino)butoxy)azanediyl)bis(nonane-9,1-diyl) bis(2-hexyldecanoate);
1-(2-(2,2-di((9Z,12Z)-octadeca-9,12-dien-1-yl)hydrazinyl)ethyl)guanidine;
O-(2-(1H-imidazol-4-yl)acetyl)-N,N-di((9Z,12Z)-octadeca-9,12-dien-1-yl) hydroxylamine;
1-(2-((di((9Z,12Z)-octadeca-9,12-dien-1-yl)amino)oxy)-2-oxoethyl)guanidine;
2-(di((9Z,12Z)-octadeca-9,12-dien-1-yl)amino)ethyl 2-(1H-imidazol-4-yl)acetate;
2-(di((9Z,12Z)-octadeca-9,12-dien-1-yl)amino)ethyl carbamimidoylglycinate;
2-(di((9Z,12Z)-octadeca-9,12-dien-1-yl)amino)ethyl dimethylglycinate;
2-(di((9Z,12Z)-octadeca-9,12-dien-1-yl)amino)ethyl 4-(dimethylamino)butanoate;
2-(di((9Z,12Z)-octadeca-9,12-dien-1-yl)amino)ethyl L-histidinate;
di((Z)-non-3-en-1-yl) 8,8'-(2-(2-(dimethylamino)ethyl)hydrazine-1,1-diyl)dioctanoate;
di((Z)-pentadec-9-en-7-yl) 8,8'-(2-(2-(dimethylamino)ethyl)hydrazine-1,1-diyl) dioctanoate;
di((Z)-pentadec-9-en-7-yl) 8,8'-(((4-(dimethylamino)butanoyl)oxy)azanediyl)dioctanoate;
di((Z)-non-3-en-1-yl) 8,8'-(((4-(dimethylamino)butanoyl)oxy)azanediyl)dioctanoate;
di((Z)-pentadec-9-en-7-yl) 8,8'-(2-(((2-(dimethylamino)ethyl)thio)carbonyl)hydrazine-1,1-diyl)dioctanoate;
di(tridecan-7-yl) 8,8'-(2-(((2-(dimethylamino)ethyl)thio)carbonyl)hydrazine-1,1-diyl) dioctanoate;
di((Z)-pentadec-9-en-7-yl) 8,8'((2-((dimethylglycyl)oxy)ethyl)azanediyl)dioctanoate;
di((Z)-non-3-en-1-yl) 8,8'-((2-((4-(dimethylamino)butanoyl)oxy) ethyl)azanediyl) dioctanoate;
di((Z)-non-3-en-1-yl) 8,8'((2-((carbamimidoylglycyl)oxy)ethyl)azanediyl)dioctanoate;

di(tridecan-7-yl) 8,8'-((2-((4-(dimethylamino)butanoyl)oxy)ethyl)azanediyl)dioctanoate;

((2-((4-(dimethylamino)butanoyl)oxy)ethyl)azanediyl) bis(octane-8,1-diyl) (3Z,3'Z)-bis(non-3-enoate);

((2-((4-(dimethylamino)butanoyl)oxy)ethyl)azanediyl) bis(heptane-7,1-diyl) bis(decanoate);

2-(di((9Z,12Z)-octadeca-9,12-dien-1-yl)amino)ethyl 4-(4-methylpiperazin-1-yl)butanoate;

di((Z)-non-3-en-1-yl) 6,6'-(2-(4-(dimethylamino)butanoyl)hydrazine-1,1-diyl)dihexanoate;

(2-(2-(dimethylamino)ethyl)hydrazine-1,1-diyl)bis(heptane-7,1-diyl) bis(decanoate);

(9Z,12Z)—N-(2-(4-(dimethylamino)butoxy)ethyl)-N-((9Z,12Z)-octadeca-9,12-dien-1-yl)octadeca-9,12-dien-1-amine;

4-(dimethylamino)-N',N'-bis(6-(((Z)-non-3-en-1-yl)oxy)hexyl)butanehydrazide;

2-(di((9Z,12Z)-octadeca-9,12-dien-1-yl)amino)ethyl 4-(pyrrolidin-1-yl)butanoate;

N-(2-(4-(dimethylamino)butoxy)ethyl)-6-(((Z)-non-3-en-1-yl)oxy)-N-(6-(((Z)-non-3-en-1-yl)oxy)hexyl)hexan-1-amine;

((2-(4-(dimethylamino)butoxy)ethyl)azanediyl)bis(heptane-7,1-diyl) bis(decanoate); and di((Z)-non-3-en-1-yl) 6,6'-((2-(4-(dimethylamino)butoxy)ethyl)azanediyl)dihexanoate.

\* \* \* \* \*